(12) United States Patent
Rosier-Montus et al.

(10) Patent No.: US 7,378,274 B2
(45) Date of Patent: May 27, 2008

(54) REGULATORY NUCLEIC ACID FOR THE ABC1 GENE, MOLECULES MODIFYING ITS ACTIVITY AND THERAPEUTIC USES

(75) Inventors: Marie-Françoise Rosier-Montus, Antony (FR); Catherine Prades, Thais (FR); Cendrine Lemoine, Massy (FR); Laurent Naudin, Etampes (FR); Patrice Denefle, Saint Maur (FR); Nicolas Duverger, Paris (FR); Bryan Brewer, Potomac, MD (US); Alan Remaley, Bethesda, MD (US); Sylvia Santamarina-Fojo, Potomac, MD (US)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/846,456

(22) Filed: May 2, 2001

(65) Prior Publication Data

US 2002/0146792 A1    Oct. 10, 2002

Related U.S. Application Data

(60) Provisional application No. 60/201,280, filed on May 2, 2000.

(51) Int. Cl.
*C07H 21/04* (2006.01)
*C12N 15/00* (2006.01)
*C12N 5/00* (2006.01)
*C12N 1/00* (2006.01)

(52) U.S. Cl. .................. 435/325; 536/24.1; 435/320.1; 435/252.3

(58) Field of Classification Search ............... 536/23.1; 435/6, 69.1, 320.1, 440, 325
See application file for complete search history.

(56) References Cited

U.S. PATENT DOCUMENTS 5,872,237 A * 2/1999 Feder et al. ............... 536/23.5
6,617,122 B1 * 9/2003 Hayden et al. ............. 435/19
6,773,893 B1 * 8/2004 Tall ........................... 435/7.2

FOREIGN PATENT DOCUMENTS

WO    WO 00/78971 A2    12/2000
WO    WO 01/15676 A2    3/2001

OTHER PUBLICATIONS

Langmann, et al. Biochemical and Biophysical Research Communications 257: 29-33, Feb. 9, 1999.*
Pullinger, et al. Biochemical and Biophysical Research Communications. May 10, 2000. vol. 271, pp. 451-455.*
Santamarina, et al. PNAS USA. Jul. 5, 2000. vol. 97, No. 14, pp. 7987-7992.*
NCBI Entrez Nucleotide Database entry AC012230.2 (Nov. 19, 1999), http://www.ncbi.nlm.nih.gov/entrez/viewer.fcgi?val=645033, downloaded Jul. 25, 2007.*
Osoegawa et al. (2001) Genome Res. 11:483-496.*
Bodzioch, M., et al., "The Gene Encoding ATP-Binding Cassette Transporter 1 is Mutated in Tangier Disease," *Nature Genetics* 22:347-351 (1999).
Langmann, T., et al., "Molecular Cloning of the Human ATP-Binding Cassette Transporter 1 (hABC1): Evidence for Sterol-Dependent Regulation in Macrophages," *Biochemical and Biophysical Research Communications* 257:29-33 (1999).
Luciani, M.F., et al., "Cloning to Two Novel ABC Transporters Mapping on Human Chromosome 9," *Genomics* 21:150-159 (1994).
Marcil, M., et al., "Mutations in the ABC1 Gene in Familial HDL Deficiency with Defective Cholesterol Efflux," *The Lancet* 354:1341-1346 (1999).
Remaley, A.T., et al., "Human ATP-Binding Cassette Transporter 1 (ABC1): Genomic Organization and Identification of the Genetic Defect in the Original Tangier Disease Kindred," *Proc. Natl. Acad. Sci. USA* 96:12685-12690 (1999).
Rust, S., et al., "Assignment of Tangier Disease to Chromosome 9q31 By a Graphical Linkage Exclusion Strategy," *Nature Genetics* 20:96-98 (1998).
Rust, S., et al., "Tangier Disease is Caused by Mutations in the Gene Encoding ATP-Binding Cassette Transporter 1," *Nature Genetics* 22:352-355 (1999).
Database EM_HTG 'Online! EBI, Hinxton, U K; AC/ID AC012230, (Oct. 22, 1999) Birren B et al.: "*Homo sapiens* clone RP11-1M10" XP002192928 See nucleotides 1100-1680, 3660-390-. 120320-120490 and 151260-151510 abstract.

* cited by examiner

Primary Examiner—Daniel M Sullivan

(57) ABSTRACT

The present invention concerns a nucleic acid which is capable of regulating the transcription of the ABC1 gene, which is a causal gene for pathologies linked to a dysfunctioning of cholesterol metabolism, inducing diseases such as atherosclerosis. The invention also relates to nucleotide constructs comprising a polynucleotide which encodes a polypeptide or a nucleic acid of interest, placed under the control a regulatory nucleic acid for the ABC1 gene. The invention also relates to recombinant vectors, transformed host cells and nonhuman transgenic mammals comprising a nucleic acid which regulates the transcription of the ABC1 gene or an abovementioned nucleotide construct, as well as methods for screening molecules or substances which are capable of modifying the activity of the regulatory nucleic acid for the ABC1 gene.

11 Claims, 8 Drawing Sheets

-2901      LMO2COM/MYOD
ACAGGGCATGG TGGCAGGTGCCT GTAATCTCAGTTACTCGGGAGGTGGAGGTTGCAATGA

-2841                                          AEF1            S8/
GCCCAGATCGCACCATTGCACTCCAGCCTGGGCAAC AAAAGGTGAAA CT CCATCTCAATT
-2781
NKX2.5
AAAAA AAAAAGAATGATTTTGGTGGTCGACTTCAAATAGGTAGGAGAAGAAGGAGAGAGG

-2721                S8                             GATA
AGATGGAGGGTCAGG GAGATCTAATTACTCT CTAAAATCATGCTAGG AAAGATAACA CCT

-2661
TTTAATAACACTCTCTGCTTTTATAACATCATTCTGCCAAGGAGCTCAAAGGTTTCAACA

-2601
AAGTTCACTTTCAGAAAACCCCTTTGAGGAAGACAGAATATACATCTTCTCTCCATTTTA

-2541                                        IK2              LYF1
AAGATGAAGAAACAGGCCGGGCACAATGGCTAATGCCT GTAATCCCAGCA CTTTGGGAGG

-2481
CTGAGGCCAGAGGATCGCTTGAGCTCCAGAGTTTGAGACCAGCCTGGATAACATGGCAAA

-2421                                         LMO2COM/MYOD/ AEF1
ACCCTGTCTCTACAAAAAAAATACAAAAATTAGATGGGTGTGGTGGC ATGCACCTGTGG T

-2361        LYF1      AEF1                               NKX2.5
CCCAGCTA CTTGGGAG G CTAAGGTGGGA GGATCGCTTGAGCCCAGGGAG TCAAGTC TACA

-2301         NFY/CAAT
CTGAGCC ATGATTGGATCAC TGCACTCCAGCCTGGGTAGACAGAGCAAGACCCTGTCTCAA

-2241                                                         MZF1
AAAAAAGAAATGAAAGAGAAAGAAAGAAAGAGGAGAGGAGAGGAGA TGAGGGGA GGAGG

-2181 MZF1                                             HFH2/SRY/
GA GGGGGGGA GGAAGGAAGGAAGGAAGGAAGGAAAAAAAGATGAAAAAAG AAAAAAACA

-2121 EVI1              CREBP1/VBP                     NKX2.5
AGATGA AACAGAGGCAGAAAGAC TTTACGTAAA TTGCTCATCATGTGGTTG TCAAGTT TGA

-2061
CCCCAAAACCCAATTTATTGACCAAGGTTATTCTTTGACTGAGGCAAGGGGGTCCGCTCT

-2001
CCTGGGCCTTGGGCTTTAGAAAGCTCATCTCTGGCCTTTCTGAGATCCATCCCTTTCTTT

Figure 1

-1941
TTATTTTTCTTGACACGGAGTCTTGCTCTGTCACTCAGGCTGGAGTGCAGTGGCATGATC

-1881
TCGACTCACTGTAACCTCTGCCTCCCGGGTTCAAGCGATTCTCCTGCCTCAGCCT[CCTGA]

-1821 GATA
[GATAACAGG]CGCCCGCCACCACATCTGGCTAATTTTTGTATTTTTAGTAAAGACTGGGTT

-1761                               LXRα/ΔEF1            ΔEF1/
TCATCATGTTGGCCAGGTTGGTTTCGAACTCC[TGACCTGAGGTGAGCT][GCCCACCTTGGC]

-1701 LYF1/IK2
[CTCCCAAAG]TGCTGGGATTACAGGCATGAGCCACTGCGCCCAGCTCAGATCCATCCCTTT

-1641
CTAAGGGCAAACAGTCCATGGTGCAAAGGGGCCATGCCACCCAGAGTTATGAGTACCTGG

-1581
GACTCCAGAATTCCTTGCCTGGTGGCCTCCACATGCACTTCCAGGGCCTGCTTGGGCCTC

-1521
TTCTATGCGTCTGTCCTGAGTGTTGATAGAACCACTGATGTGAGTACCTGGGCTTGAGCC

-1461                                             AP4         LMO2-
GTGGCCTGGAGATCCTGTTGACTGTAGCATGGAGGGGGCTTG[TGCAGCTGAA]TGTCT[GCA]

-1401 COM/MYOD/ ΔEF1/E47        ZID/ΔEF1
[TGCAGGTGGTGGGA]GTTCTGGAA[TATGATGGAGCTGGAGGTGGGA]AGAGAAGTAGGCTTG

-1341                                    ΔEF1
GGGCAGCTCTCTCATGCCACCTCATTCTGGCCAAAA[CTCAGGTCAAA]CTGTGAAGAGTCT

-1281 PPAR      PPAR
A[AATGTG]AATC[TGCCCT]TCAAGGTGGCTACAAAGGTATCTTTGTCAAGGTAGGAGACCTT

-1221 USF/NMYC/MYCMAX
GTGG[CCTCCACGTGCACT]TCCAGGGCCTGCTTGGGCCTCTTCTACGGGTCTGTCCTGAGT

-1161                                              ΔEF1
CTTCTATGAATCCTTCAGGGCAGATTCATATTTAGACTCTTCACAG[TTTGACCTG]

-1101           ΔEF1           SRY              AP1
[AG]TTTTGGCCAGA[ATAAGGTGACA]TT[TAGTTTGTTGGC]TTGATG[GATGACTTAAA]TATTT

-1041
AGACATGGTGTGTAGGCCTGCATTCCTACTCTTGCCTTTTTTTTGCCCCTCCAGTGTTT

-981                        HNF3β
TGGGTAGTTTTGCTCCCCTACAGCCA[AAGGCAAACAGAGAA]GTTGGAGGTCTGGAGTGG

Figure 1 (Suite 1)

```
-921    NKX2.5                              PPAR/NKX2.5/PPAR
CTA[CATAATTT]TACACGACTGCAATTCTCTGGC[TGCACT][TCA]CA[AATGTA]TACAAACTAA

-861                    GATA
ATACAAGTCCTGTGTT[TTTATCACA]GGGAGGCTGATCAATATAATGAAATTAAAAGGGGG

-801            SOX5            SRY/HFH/HNF3β    SRY/HFH/HNF3β
CTGGTCCAT[ATTGTTCT]GT[GTTTTTGTTTGTTTGTTTTGTTTGTTTCTTTTTTTGTTT]T

-741
TGTGGCCTCCTTCCTCTCAATTTATGAAGAGAAGCAGTAAGATGTTCCTCTCGGGTCCTC

-681        MZF1            IK2/NFκB/CREL                LMO2COM/GATA
TGAGGGA[CCTGGGGA]GCTCA[GGCTGGGAATCTCCAA]GGCAGTAGG[TCGCCTATCAAAAA]T

-621                MZF1/SRY            PPAR        PPAR
CAAAGTCCAGGTTTG[TGGGGGGAAAACAAAAGC]AGCCCA[TTACCC]AG[AGGACT]GTCCGCC

-561 MZF1                    HNF3β/SRY/EVI1
T[TCCCCTCA]CCCCAGCCTAGGCCTTTG[AAAGGAAACAAAAGACAAGACAAA]ATGATTGGC

-501                            MZF1            AP4
GTCCTGAGGGAGATTCAGCCTAGAGCTCTCT[CTCCCCCAA]TCCCTCCC[TCCGGCTGAG]GA

-441    SRY                            STAT
A[ACTAACAAAGGA]AAAAAAAATTGCGGAAAGCAGGAT[TTAGAGGA]AGCAAATTCCACTGG

-381        STAT/PPAR    PPAR
TGCCCTTGGC[TGCCG][GGAACG][TGGACTA]GAGAGTCTGCGGCGCAGCCCCGAGCCCAGCGC

-321            AP2                MZF1
TTCCCGCGCGTCTTA[GGCCGGCGGGCC]CGGGCGGGG[GAAGGGGA]CGCAGACCGCGGACCC

-261 LMO2COM/MYOD/E47        RREB1                        MZF1/
[TAAGACACCTGCTGT]ACCCTCCA[CCCCCACCCCACCCCA]CCCACCT[CCCCCCAACTCCCT]

-201 CMYB                        SP1/GC            USF/NMYC/
[AGATG]TGTCGTGGGCGGCTGAACGTCGCCCGTTT[AAGGGGCGGGCCC]CG[GCTCCACGTGC]

-141 ARNT    NFE2/AP1    XFD1/HFH                GC/SP1/MZF1
[TTTC][TGCTGAGTGACTGAAC][TACATAAACAGAGG]CCGGGA[AGGGGCGGGGAG]GAGGGAG

-81                                                    TATA
AGCACAGGCTTTG[ACCGATAGTAACCTC]TGCGCTCGGTGCAGCCGAA[TCTATAAAAG]GAA

-21         +1
CTAGTCCCGGCAAAAACCCC[G]TAATTGCGAGCGAGAG
```

Figure 1 (suite 2)

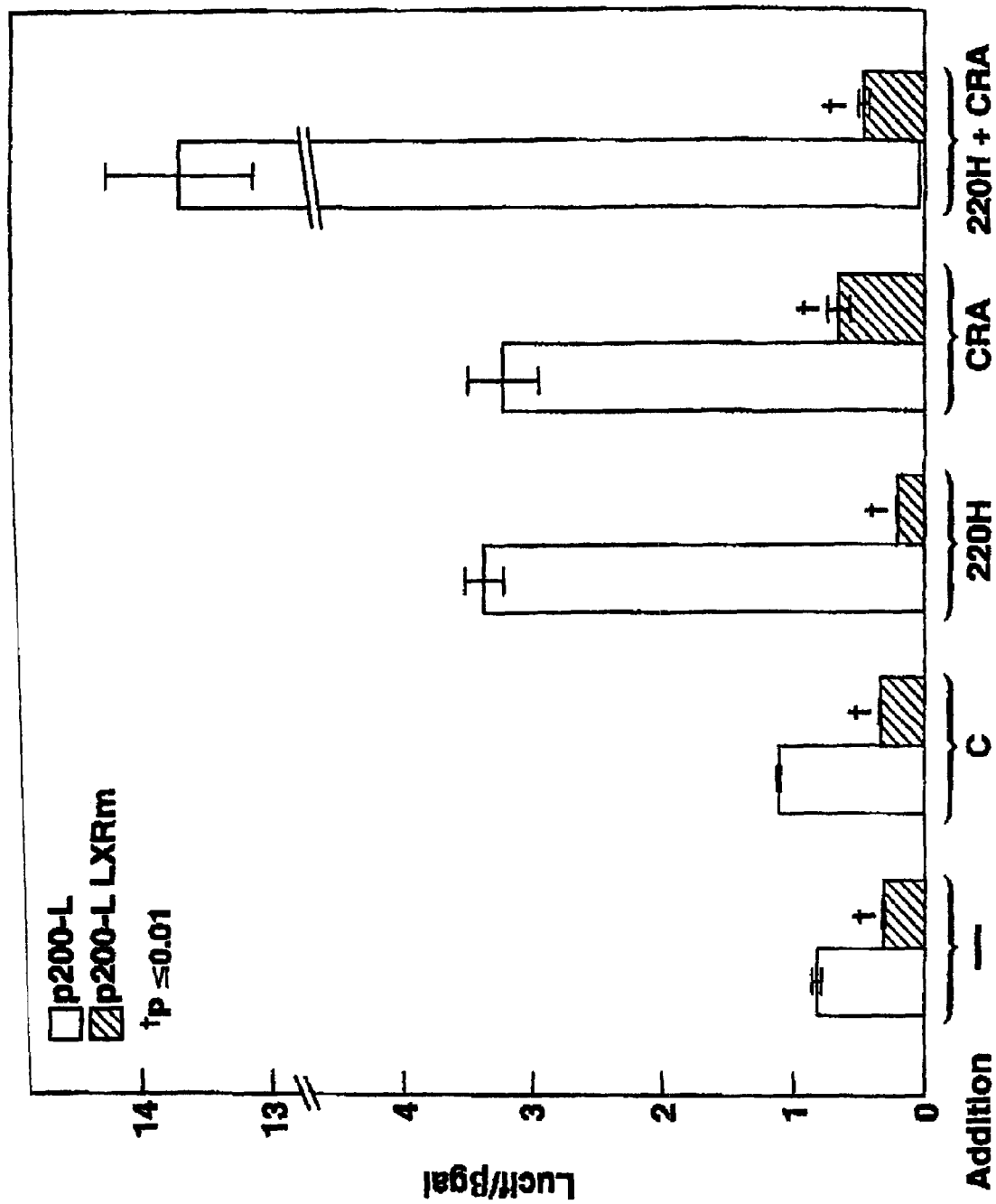

FIGURE 6A
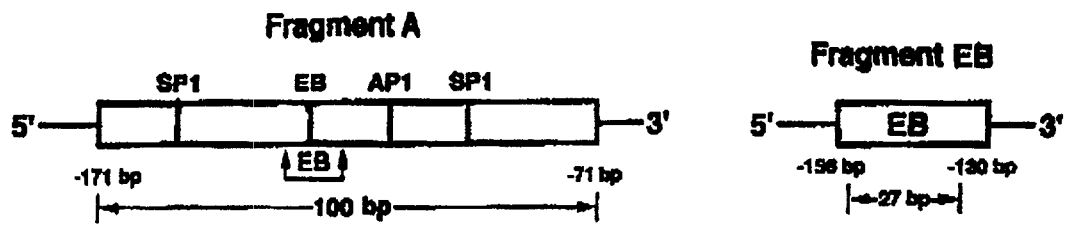
FIGURE 6B
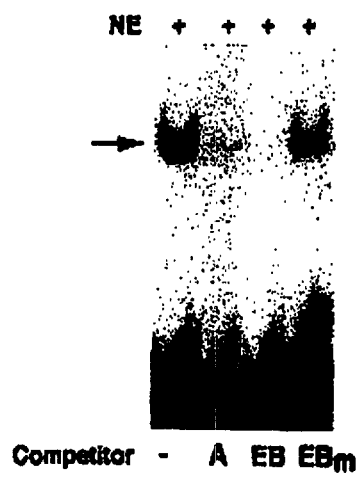  
FIGURE 6C
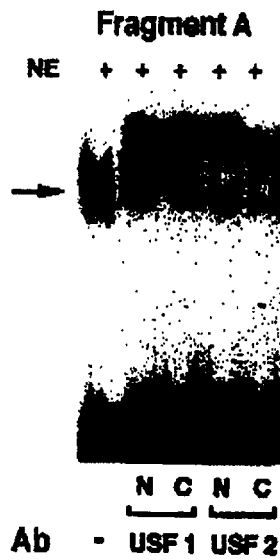 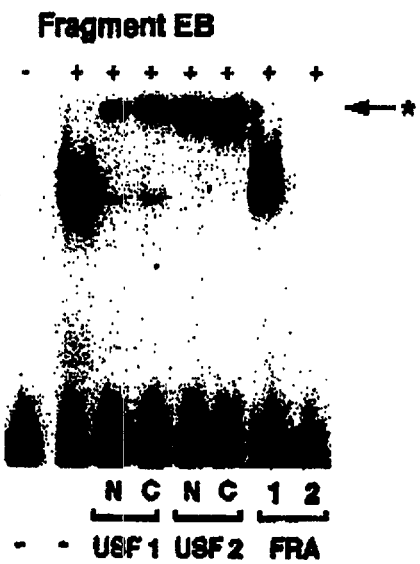

SEQUENCE LISTING

<160> NUMBER OF SEQ ID NOS: 20

<210> SEQ ID NO 1
<211> LENGTH: 3231

<212> TYPE: DNA
<213> ORGANISM: Homo sapiens

<400> SEQUENCE: 1

```
acagggcatg gtggcaggtg cctgtaatct cagttactcg ggaggtggag gttgcaatga      60
gcccagatcg caccattgca ctccagcctg gcaacaaaa ggtgaaactc catctcaatt     120
aaaaaaaaaa gaatgatttt ggtggtcgac ttcaaatagg taggagaaga aggagagagg     180
agatggaggg tcagggagat ctaattactc tctaaaatca tgctaggaaa gataacacct     240
tttaataaca ctctctgctt ttataacatc attctgccaa ggagctcaaa ggtttcaaca     300
aagttcactt tcagaaaacc cctttgagga agacagaata tacatcttct ctccatttta     360
aagatgaaga aacaggccgg gcacaatggc taatgcctgt aatcccagca ctttgggagg     420
ctgaggccag aggatcgctt gagctccaga gtttgagacc agcctggata acatggcaaa     480
accctgtctc tacaaaaaaa atacaaaaat tagatgggtg tggtggcatg cacctgtggt     540
cccagctact tgggaggcta aggtgggagg atcgcttgag cccagggagt caagtctaca     600
ctgagccatg attggatcac tgcactccag cctgggtaga cagagcaaga ccctgtctca     660
aaaaaagaa atgaaagaga aagaaagaaa gaggagagga gaggagatga ggggaggagg     720
gagggggga ggaaggaagg aaggaaggaa ggaaaaaaag atgaaaaaag aaaaaaacaa     780
gatgaaacag aggcagaaag actttacgta aattgctcat catgtggttg tcaagtttga     840
ccccaaaacc caatttattg accaaggtta ttctttgact gaggcaaggg ggtccgctct     900
cctgggcctt gggctttaga aagctcatct ctggcctttc tgagatccat ccctttcttt     960
ttatttttct tgacacggag tcttgctctg tcactcaggc tggagtgcag tggcatgatc    1020
tcgactcact gtaacctctg cctcccgggt tcaagcgatt ctcctgcctc agcctcctga    1080
gataacaggc gcccgccacc acatctggct aattttgta ttttagtaa agactgggtt    1140
tcatcatgtt ggccaggttg gtttcgaact cctgacctga ggtgagctgc ccaccttggc    1200
ctcccaaagt gctgggatta caggcatgag ccactgcgcc cagctcagat ccatcccttt    1260
ctaagggcaa acagtccatg gtgcaaaggg gccatgccac ccagagttat gagtacctgg    1320
gactccagaa ttccttgcct ggtggcctcc acatgcactt ccagggcctg cttgggcctc    1380
ttctatgcgt ctgtcctgag tgttgataga accactgatg tgagtacctg gcttgagcc    1440
gtggcctgga gatcctgttg actgtagcat ggaggggct tgtgcagctg aatgtctgca    1500
tgcaggtggt gggagttctg gaatatgatg gagctgagg tgggaagaga agtaggcttg    1560
gggcagctct ctcatgccac ctcattctgg ccaaaactca ggtcaaactg tgaagagtct    1620
aaatgtgaat ctgccccttca aggtggctac aaaggtatct ttgtcaaggt aggagacctt    1680
gtggcctcca cgtgcacttc cagggcctgc ttgggcctct tctacgggtc tgtcctgagt    1740
cttctatgaa tccttcaggg cagattcata tttagactct tcacagtttg acctgagttt    1800
tggccagaat aaggtgacat ttagtttgtt ggcttgatgg atgacttaaa tatttagaca    1860
tggtgtgtag gcctgcattc ctactcttgc cttttttttt gccctccag tgttttgggt    1920
agttttgctc ccctacagcc aaaggcaaac agagaagttg gaggtctgga gtggctacat    1980
aattttacac gactgcaatt ctctggctgc acttcacaaa tgtatacaaa ctaaatacaa    2040
gtcctgtgtt tttatcacag ggaggctgat caatataatg aaattaaaag ggggctggtc    2100
catattgttc tgtgttttg tttgtttgtt ttgtttgttt cttttttttgt ttttgtggcc    2160
tccttcctct caatttatga agagaagcag taagatgttc ctctcgggtc ctctgaggga    2220
```

-continued

```
cctggggagc tcaggctggg aatctccaag gcagtaggtc gcctatcaaa aatcaaagtc    2280
caggtttgtg gggggaaaac aaaagcagcc cattacccag aggactgtcc gccttcccct    2340
caccccagcc taggcctttg aaaggaaaca aaagacaaga caaatgatt ggcgtcctga     2400 gggagattca gcctagagct ctctctcccc caatccctcc ctccggctga ggaaactaac    2460
aaaggaaaaa aaaattgcgg aaagcaggat ttagaggaag caaattccac tggtgccctt    2520
ggctgccggg aacgtggact agagagtctg cggcgcagcc ccgagcccag cgcttcccgc    2580
gcgtcttagg ccggcgggcc cgggcggggg aaggggacgc agaccgcgga ccctaagaca    2640
cctgctgtac cctccacccc cacccccaccc cacccacctc cccccaactc cctagatgtg    2700
tcgtgggcgg ctgaacgtcg cccgtttaag gggcgggccc cggctccacg tgctttctgc    2760
tgagtgactg aactacataa acagaggccg gaagggggc ggggaggagg gagagcacag     2820
gctttgaccg atagtaacct ctgcgctcgg tgcagccgaa tctataaaag gaactagtcc    2880
cggcaaaaac cccgtaattg cgagcgagag tgagtggggc cggacccgc agagccgagc     2940 cgacccttct ctcccgggct gcggcagggc agggcgggga gctccgcgca ccaacagagc    3000
cggttctcag ggcgctttgc tccttgtttt tccccggtt ctgttttctc ccttctccg      3060 gaaggcttgt caaggggtag gagaaagaga cgcaaacaca aaagtggaaa acaggtaaga    3120
ggctctccag tgacttactt gggcgttatt gttttgtttc gaggcaagg aggcttcggg     3180 aagtgctcgg tttcggggac tttgatccgg agccccacat ccccaccact t             3231

<210> SEQ ID NO 2
<211> LENGTH: 357
<212> TYPE: DNA
<213> ORGANISM: Homo sapiens

<400> SEQUENCE: 2
tggaggtctc agctgagagg gctggattag cagtcctcat tggtgtatgg ctttgcagca     60
ataactgatg gctgtttccc ctcctgcttt atctttcagt taatgaccag ccacgggcgt    120
ccctgctgtc agctctggcc gctgccttcc agggctcccg agccacacgc tgggcgtgct    180
ggctgaggga acatggcatg ttggcctcag ctgaggttgc tgctgtggaa gaacctcact    240
ttcagaagaa gacaaacagt aagcttgggt ttttcagcag cggggggttc tctcatttt     300 tctttgtggt tttgagttgg ggattggagg agggagggag ggaaggaagc tgtgttg       357

<210> SEQ ID NO 3
<211> LENGTH: 2893
<212> TYPE: DNA
<213> ORGANISM: Homo sapiens

<400> SEQUENCE: 3
acagggcatg gtggcaggtg cctgtaatct cagttactcg ggaggtggag gttgcaatga     60
gcccagatcg caccattgca ctccagcctg gcaacaaaa ggtgaaactc catctcaatt     120
aaaaaaaaaa gaatgatttt ggtggtcgac ttcaaatagg taggagaaga aggagagagg    180
agatggaggg tcaggagat ctaattactc tctaaaatca tgctaggaaa gataacacct     240
tttaataaca ctctctgctt ttataacatc attctgccaa ggagctcaaa ggtttcaaca    300
aagttcactt tcagaaaacc cctttgagga agacagaata tacatcttct ctccatttta    360
aagatgaaga aacaggccgg gcacaatggc taatgcctgt aatcccagca ctttgggagg    420
ctgaggccag aggatcgctt gagctccaga gtttgagacc agcctggata acatggcaaa    480
accctgtctc tacaaaaaaa atacaaaaat tagatgggtg tggtggcatg cacctgtggt    540
```

```
cccagctact tgggaggcta aggtgggagg atcgcttgag cccagggagt caagtctaca    600
ctgagccatg attggatcac tgcactccag cctgggtaga cagagcaaga ccctgtctca    660
aaaaaaagaa atgaaagaga aagaaagaaa gaggagagga gaggagatga ggggaggagg    720
gaggggggga ggaaggaagg aaggaaggaa ggaaaaaaag atgaaaaaag aaaaaaacaa    780
gatgaaacag aggcagaaag actttacgta aattgctcat catgtggttg tcaagtttga    840
ccccaaaacc caatttattg accaaggtta ttctttgact gaggcaaggg ggtccgctct    900
cctgggcctt gggctttaga aagctcatct ctggcctttc tgagatccat ccctttcttt    960
ttatttttct tgacacggag tcttgctctg tcactcaggc tggagtgcag tggcatgatc   1020
tcgactcact gtaacctctg cctcccgggt tcaagcgatt ctcctgcctc agcctcctga   1080
gataacaggc gcccgccacc acatctggct aattttttgta tttttagtaa agactgggtt   1140
tcatcatgtt ggccaggttg gtttcgaact cctgacctga ggtgagctgc ccaccttggc   1200
ctcccaaagt gctgggatta caggcatgag ccactgcgcc cagctcagat ccatcccttt   1260
ctaagggcaa acagtccatg gtgcaaaggg gccatgccac ccagagttat gagtacctgg   1320
gactccagaa ttccttgcct ggtggcctcc acatgcactt ccagggcctg cttgggcctc   1380
ttctatgcgt ctgtcctgag tgttgataga accactgatg tgagtacctg gcttgagcc   1440
gtggcctgga gatcctgttg actgtagcat ggagggggct tgtgcagctg aatgtctgca   1500
tgcaggtggt gggagttctg gaatatgatg gagctggagg tgggaagaga agtaggcttg   1560
gggcagctct ctcatgccac ctcattctgg ccaaaactca ggtcaaactg tgaagagtct   1620
aaatgtgaat ctgcccttca aggtggctac aaaggtatct ttgtcaaggt aggagacctt   1680
gtggcctcca cgtgcacttc cagggcctgc ttgggcctct tctacgggtc tgtcctgagt   1740
cttctatgaa tccttcaggg cagattcata tttagactct tcacagtttg acctgagttt   1800
tggccagaat aaggtgacat ttagtttgtt ggcttgatgg atgacttaaa tatttagaca   1860
tggtgtgtag gcctgcattc ctactcttgc ctttttttttt gcccctccag tgttttgggt   1920
agttttgctc ccctacagcc aaaggcaaac agagaagttg gaggtctgga gtggctacat   1980
aattttacac gactgcaatt ctctggctgc acttcacaaa tgtatacaaa ctaaatacaa   2040
gtcctgtgtt tttatcacag ggaggctgat caatataatg aaattaaaag ggggctggtc   2100
catattgttc tgtgtttttg tttgtttgtt ttgtttgttt cttttttttgt ttttgtggcc   2160
tccttcctct caatttatga agagaagcag taagatgttc ctctcgggtc ctctgaggga   2220
cctggggagc tcaggctggg aatctccaag gcagtaggtc gcctatcaaa aatcaaagtc   2280
caggtttgtg gggggaaaac aaaagcagcc cattacccag aggactgtcc gccttcccct   2340
cacccccagcc taggccttttg aaaggaaaca aaagacaaga caaaatgatt ggcgtcctga   2400
gggagattca gcctagagct ctctctcccc caatccctcc ctccggctga ggaaactaac   2460
aaaggaaaaa aaaattgcgg aaagcaggat ttagaggaag caaattccac tggtgccctt   2520
ggctgccggg aacgtggact agagagtctg cggcgcagcc ccgagcccag cgcttcccgc   2580
gcgtcttagg ccggcgggcc cgggcggggg aaggggacgc agaccgcgga ccctaagaca   2640
cctgctgtac cctccacccc caccccaccc cacccacctc ccccaactc cctagatgtg   2700
tcgtgggcgg ctgaacgtcg cccgtttaag gggcgggccc cggctccacg tgctttctgc   2760
tgagtgactg aactacataa acagaggccg gaaggggggc ggggaggagg gagagcacag   2820
gctttgaccg atagtaacct ctgcgctcgg tgcagccgaa tctataaaag gaactagtcc   2880
```
cggcaaaaac ccc                                                         2893

<210> SEQ ID NO 4
<211> LENGTH: 221
<212> TYPE: DNA
<213> ORGANISM: Homo sapiens

<400> SEQUENCE: 4
gtaattgcga gcgagagtga gtggggccgg gacccgcaga gccgagccga cccttctctc        60
ccgggctgcg gcagggcagg gcggggagct ccgcgcacca acagagccgg ttctcagggc       120
gctttgctcc ttgttttttc cccggttctg ttttctcccc ttctccggaa ggcttgtcaa       180
ggggtaggag aaagagacgc aaacacaaaa gtggaaaaca g                           221

<210> SEQ ID NO 5
<211> LENGTH: 159
<212> TYPE: DNA
<213> ORGANISM: Homo sapiens

<400> SEQUENCE: 5
ttaatgacca gccacgggcg tccctgctgt cagctctggc cgctgccttc cagggctccc        60
gagccacacg ctgggcgtgc tggctgaggg aacatggcat gttggcctca gctgaggttg       120
ctgctgtgga agaacctcac tttcagaaga agacaaaca                              159

<210> SEQ ID NO 6
<211> LENGTH: 117
<212> TYPE: DNA
<213> ORGANISM: Homo sapiens

<400> SEQUENCE: 6
gtaagaggct ctccagtgac ttacttgggc gttattgttt tgtttcgagg ccaaggaggc        60
ttcgggaagt gctcggtttc ggggactttg atccggagcc ccacatcccc accactt         117

<210> SEQ ID NO 7
<211> LENGTH: 99
<212> TYPE: DNA
<213> ORGANISM: Homo sapiens

<400> SEQUENCE: 7
tggaggtctc agctgagagg gctggattag cagtcctcat tggtgtatgg ctttgcagca        60
ataactgatg gctgtttccc ctcctgcttt atctttcag                               99

<210> SEQ ID NO 8
<211> LENGTH: 99
<212> TYPE: DNA
<213> ORGANISM: Homo sapiens

<400> SEQUENCE: 8
gtaagcttgg ttttttcagc agcgggggt tctctcattt tttctttgtg gttttgagtt         60
ggggattgga ggagggaggg agggaaggaa gctgtgttg                               99

<210> SEQ ID NO 9
<211> LENGTH: 22
<212> TYPE: PRT
<213> ORGANISM: Homo sapiens

<400> SEQUENCE: 9

Met Ala Cys Trp Pro Gln Leu Arg Leu Leu Leu Trp Lys Asn Leu Thr
1               5                   10                  15

Phe Arg Arg Arg Gln Thr
              20

<210> SEQ ID NO 10
<211> LENGTH: 9741
<212> TYPE: DNA
<213> ORGANISM: Homo sapiens
<220> FEATURE:
<221> NAME/KEY: misc_feature
<223> OTHER INFORMATION: "n" is chosen from g, a, t and c

<400> SEQUENCE: 10

| | | | | | |
|---|---|---|---|---|---|
| cttgtttttt | ccccggttct | gttttctccc | cttctccgga | aggcttgtca | agggggtagga | 60 |
| gaaagagacg | caaacacaaa | agtggaaaac | agttaatgac | cagccacggc | gtccctgctg | 120 |
| tgagctctgg | ccgctgcctt | ccagggctcc | cgagccacac | gctggggggtg | ctggctgagg | 180 |
| gaacatggct | tgttggcctc | agctgaggtt | gctgctgtgg | aagaacctca | ctttcagaag | 240 |
| aagacaaaca | tgtcagctgc | tgctggaagt | ggcctggcct | ctatttatct | tcctgatcct | 300 |
| gatctctgtt | cggctgagct | acccacccta | tgaacaacat | gaatgccatt | ttccaaataa | 360 |
| agccatgccc | tctgcaggaa | cacttccttg | ggttcagggg | attatctgta | atgccaacaa | 420 |
| cccctgtttc | cgttacccga | ctcctgggga | ggctcccgga | gttgttggaa | actttaacaa | 480 |
| atccattgtg | gctcgcctgt | tctcagatgc | tcggaggctt | cttttataca | gccagaaaga | 540 |
| caccagcatg | aaggacatgc | gcaaagttct | gagaacatta | cagcagatca | agaaatccag | 600 |
| ctcaaacttg | aagcttcaag | atttcctggt | ggacaatgaa | accttctctg | ggttcctgta | 660 |
| tcacaacctc | tctctcccaa | agtctactgt | ggacaagatg | ctgagggctg | atgtcattct | 720 |
| ccacaaggta | tttttgcaag | gctaccagtt | acatttgaca | agtctgtgca | atggatcaaa | 780 |
| atcagaagag | atgattcaac | ttggtgacca | agaagtttct | gagctttgtg | gcctaccaag | 840 |
| ggagaaactg | gctgcagcag | agcgagtact | tcgttccaac | atggacatcc | tgaagccaat | 900 |
| cctgagaaca | ctaaactcta | catctccctt | cccgagcaag | gagctggccg | aagccacaaa | 960 |
| aacattgctg | catagtcttg | ggactctggc | ccaggagctg | ttcagcatga | aagctggag | 1020 |
| tgacatgcga | caggaggtga | tgtttctgac | caatgtgaac | agctccagct | cctccacca | 1080 |
| aatctaccag | gctgtgtctc | gtattgtctg | cgggcatccc | gagggaggg | ggctgaagat | 1140 |
| caagtctctc | aactggtatg | aggacaacaa | ctacaaagcc | ctctttggag | gcaatggcac | 1200 |
| tgaggaagat | gctgaaacct | tctatgacaa | ctctacaact | ccttactgca | atgatttgat | 1260 |
| gaagaatttg | gagtctagtc | ctctttcccg | cattatctgg | aaagctctga | gccgctgct | 1320 |
| cgttgggaag | atcctgtata | cacctgacac | tccagccaca | aggcaggtca | tggctgaggt | 1380 |
| gaacaagacc | ttccaggaac | tggctgtgtt | ccatgatctg | gaaggcatgt | gggaggaact | 1440 |
| cagccccaag | atctggacct | tcatggagaa | cagccaagaa | atggaccttg | tccggatgct | 1500 |
| gttggacagc | agggacaatg | accactttg | ggaacagcag | ttggatgct | tagattggac | 1560 |
| agcccaagac | atcgtggcgt | ttttggccaa | gcacccagag | gatgtccagt | ccagtaatgg | 1620 |
| ttctgtgtac | acctggagag | aagctttcaa | cgagactaac | caggcaatcc | ggaccatatc | 1680 |
| tcgcttcatg | gagtgtgtca | acctgaacaa | gctagaaccc | atagcaacag | aagtctggct | 1740 |
| catcaacaag | tccatggagc | tgctggatga | gaggaagttc | tgggctggta | ttgtgttcac | 1800 |
| tggaattact | ccaggcagca | ttgagctgcc | ccatcatgtc | aagtacaaga | tccgaatgga | 1860 |
| cattgacaat | gtggagagga | caaataaaat | caaggatggg | tactgggacc | ctggtcctcg | 1920 |
| agctgacccc | tttgaggaca | tgcggtacgt | ctgggggggc | ttcgcctact | gcaggatgt | 1980 |

```
ggtggagcag gcaatcatca gggtgctgac gggcaccgag aagaaaactg gtgtctatat    2040
gcaacagatg ccctatccct gttacgttga tgacatcttt ctgcgggtga tgagccggtc    2100
aatgcccctc ttcatgacgc tggcctggat ttactcagtg gctgtgatca tcaagggcat    2160
cgtgtatgag aaggaggcac ggctgaaaga gaccatgcgg atcatgggcc tggacaacag    2220
catcctctgg tttagctggt tcattagtag cctcattcct cttcttgtga gcgctggcct    2280
gctagtggtc atcctgaagt taggaaacct gctgccctac agtgatccca gcgtggtgtt    2340
tgtcttcctg tccgtgtttg ctgtggtgac aatcctgcag tgcttcctga ttagcacact    2400
cttctccaga gccaacctgg cagcagcctg tgggggcatc atctacttca cgctgtacct    2460
gccctacgtc ctgtgtgtgg catggcagga ctacgtgggc ttcacactca agatcttcgc    2520
tagcctgctg tctcctgtgg ctttgggtt tggctgtgag tactttgccc tttttgagga    2580
gcagggcatt ggagtgcagt gggacaacct gtttgagagt cctgtggagg aagatggctt    2640
caatctcacc acttcggtct ccatgatgct gtttgacacc ttcctctatg gggtgatgac    2700
ctggtacatt gaggctgtct ttccaggcca gtacggaatt cccaggccct ggtattttcc    2760
ttgcaccaag tcctactggt ttggcgagga aagtgatgag aagagccacc ctggttccaa    2820
ccagaagaga atatcagaaa tctgcatgga ggaggaaccc acccacttga agctgggcgt    2880
gtccattcag aacctggtaa aagtctaccg agatgggatg aaggtggctg tcgatggcct    2940
ggcactgaat tttatgaggg ccagatcac ctccttcctg gccacaatg agcggggaa     3000
gacgaccacc atgtcaatcc tgaccggttt gttcccccccg acctcgggca ccgcctacat    3060
cctgggaaaa gacattcgct ctgagatgag caccatccgg cagaacctgg ggtctgtcc     3120
ccagcataac gtgctgtttg acatgctgac tgtcgaagaa cacatctggt tctatgcccg    3180
cttgaaaggg ctctctgaga agcacgtgaa ggcggagatg gagcagatgg ccctggatgt    3240
tggtttgcca tcaagcaagc tgaaaagcaa acaagccag ctgtcaggtg gaatgcagag     3300
aaagctatct gtggccttgg cctttgtcgg gggatctaag gttgtcattc tggatgaacc    3360
cacagctggt gtggacccctt actcccgcag gggaatatgg gagctgctgc tgaaataccg    3420
acaaggccgc accattattc tctctacaca ccacatggat gaagcggacg tcctggggga    3480
caggattgcc atcatctccc atgggaagct gtgctgtgtg ggctcctccc tgtttctgaa    3540
gaaccagctg ggaacaggct actacctgac cttggtcaag aaagatgtgg aatcctccct    3600
cagttcctgc agaaacagta gtagcactgt gtcatacctg aaaaaggagg acagtgtttc    3660
tcagagcagt tctgatgctg gcctgggcag cgaccatgag agtgacacgc tgaccatcga    3720
tgtctctgct atctccaacc tcatcaggaa gcatgtgtct gaagcccggc tggtggaaga    3780
cataggggcat gagctgacct atgtgctgcc atatgaagct gctaaggagg gagcctttgt    3840
ggaactcttt catgagattg atgaccggct ctcagacctg gcatttctta gttatggcat    3900
ctcagagacg accctggaag aaatattcct caaggtggcc gaagagagtg gggtggatgc    3960
tgagacctca gatggtacct tgccagcaag acgaaacagg cgggccttcg gggacaagca    4020
gagctgtctt cgcccgttca ctgaagatga tgctgctgat ccaaatgatt ctgacataga    4080
cccagaatcc agagagacag acttgctcag tgggatggat ggcaaagggt cctaccaggt    4140
gaaaggctgg aaacttacac agcaacagtt tgtggccctt ttgtggaaga gactgctaat    4200
tgccagacgg agtcggaaag gattttttgc tcagattgtc ttgccagctg tgttgtctg     4260
cattgccctt gtgttcagcc tgatcgtgcc accctttggc aagtacccca gcctggaact    4320
```

```
tcagccctgg atgtacaacg aacagtacac atttgtcagc aatgatgctc ctgaggacac    4380
gggaaccctg gaactcttaa acgccctcac caaagaccct ggcttcggga cccgctgtat    4440
ggaaggaaac ccaatcccag acacgccctg ccaggcaggg gaggaagagt ggaccactgc    4500
cccagttccc cagaccatca tggacctctt ccagaatggg aactggacaa tgcagaaccc    4560
ttcacctgca tgccagtgta gcagcgacaa aatcaagaag atgctgcctg tgtgtccccc    4620
aggggcaggg gggctgcctc ctccacaaag aaaacaaaac actgcagata tccttcagga    4680
cctgacagga agaaacattt cggattatct ggtgaagacg tatgtgcaga tcatagccaa    4740
aagcttaaag aacaagatct gggtgaatga gtttaggtat ggcggctttt ccctgggtgt    4800
cagtaatact caagcacttc ctccgagtca agaagttaat gatgccacca acaaatgaa     4860
gaaacaccta aagctggcca aggacagttc tgcagatcga tttctcaaca gcttgggaag    4920
atttatgaca ggactggaca ccagaaataa tgtcaaggtg tggttcaata caagggctg     4980
gcatgcaatc agctctttcc tgaatgtcat caacaatgcc attctccggg ccaacctgca    5040
aaagggagag aaccctagcc attatggaat tactgctttc aatcatcccc tgaatctcac    5100
caagcagcag ctctcagagg tggctccgat gaccacatca gtggatgtcc ttgtgtccat    5160
ctgtgtcatc tttgcaatgt ccttcgtccc agccagcttt gtcgtattcc tgatccagga    5220
gcgggtcagc aaagcaaaac acctgcagtt catcagtgga gtgaagcctg tcatctactg    5280
gctctctaat tttgtctggg atatgtgcaa ttacgttgtc cctgccacac tggtcattat    5340
catcttcatc tgcttccagc agaagtccta tgtgtcctcc accaatctgc ctgtgctagc    5400
ccttctactt ttgctgtatg ggtggtcaat cacacctctc atgtacccag cctcctttgt    5460
gttcaagatc cccagcacag cctatgtggt gctcaccagc gtgaacctct tcattggcat    5520
taatggcagc gtggccacct tgtgctgga  gctgttcacc gacaataagc tgaataatat    5580
caatgatatc ctgaagtccg tgttcttgat cttcccacat ttttgcctgg gacgagggct    5640
catcgacatg gtgaaaaacc aggcaatggc tgatgccctg aaaggtttg  gggagaatcg    5700
ctttgtgtca ccattatctt gggacttggt gggacgaaac ctcttcgcca tggccgtgga    5760
aggggtggtg ttcttcctca ttactgttct gatccagtac agattcttca tcaggcccag    5820
acctgtaaat gcaaagctat ctcctctgaa tgatgaagat gaagatgtga ggcgggaaag    5880
acagagaatt cttgatggtg gaggccagaa tgacatctta gaaatcaagg agttgacgaa    5940
gatatataga aggaagcgga agcctgctgt tgacaggatt tgcgtgggca ttcctcctgg    6000
tgagtgcttt gggctcctgg gagttaatgg ggctggaaaa tcatcaactt tcaagatgtt    6060
aacaggagat accactgtta ccagaggaga tgctttcctt aacagaaata gtatcttatc    6120
aaacatccat gaagtacatc agaacatggg ctactgccct cagtttgatg ccatcacaga    6180
gctgttgact gggagagaac acgtggagtt ctttgccctt ttgagaggag tcccagagaa    6240
agaagttgc  aaggttggtg agtgggcgat tcggaaactg ggcctcgtga agtatgagga    6300
aaaatatgct ggtaactata gtggaggcaa caaacgcaag ctctctacag ccatggcttt    6360
gatcggcggg cctcctgtgg tgtttctgga tgaacccacc acaggcatgg atcccaaagc    6420
ccggcggttc ttgtggaatt gtgccctaag tgttgtcaag gaggggagat cagtagtgct    6480
tacatctcat agtatggaag aatgtgaagc tctttgcact aggatggcaa tcatggtcaa    6540
tggaaggttc aggtgccttg gcagtgtcca gcatctaaaa aataggtttg gagatggtta    6600
tacaatagtt gtacgaatag cagggtccaa cccggacctg aagcctgtcc aggatttctt    6660
tggacttgca tttcctggaa gtgttccaaa agagaaacac cggaacatgc tacaatacca    6720
```

```
gcttccatct tcattatctt ctctggccag gatattcagc atcctctccc agagcaaaaa    6780
gcgactccac atagaagact actctgtttc tcagacaaca cttgaccaag tatttgtgaa    6840
ctttgccaag gaccaaagtg atgatgacca cttaaaagac ctctcattac acaaaaacca    6900
gacagtagtg gacgttgcag ttctcacatc ttttctacag gatgagaaag tgaaagaaag    6960
ctatgtatga agaatcctgt tcatacgggg tggctgaaag taaagaggna ctagactttc    7020
ctttgcacca tgtgaagtgt tgtggagaaa agagccagaa gttgatgtgg aagaagtaa     7080 actggatact gtactgatac tattcaatgc aatgcaattc aatgcaatga aaacaaaatt    7140
ccattacagg ggcagtgcct ttgtagccta tgtcttgtat ggctctcaag tgaaagactt    7200
gaatttagtt ttttacctat acctatgtga aactctatta tggaacccaa tggacatatg    7260
ggtttgaact cacactttt tttttttttt gttcctgtgt attctcattg gggttgcaac     7320
aataattcat caagtaatca tggccagcga ttattgatca aaatcaaaag gtaatgcaca    7380
tcctcattca ctaagccatg ccatgcccag gagactggtt cccggtgac acatccattg     7440 ctggcaatga gtgtgccaga gttattagtg ccaagttttt cagaaagttt gaagcaccat    7500
ggtgtgtcat gctcactttt gtgaaagctg ctctgctcag agtctatcaa cattgaatat    7560
cagttgacag aatggtgcca tgcgtggcta acatcctgct ttgattccct ctgataagct    7620
gttctggtgg cagtaacatg caacaaaaat gtgggtgtct ctaggcacgg gaaacttggt    7680
tccattgtta tattgtccta tgcttcgagc catgggtcta cagggtcatc cttatgagac    7740
tcttaaatat acttagatcc tggtaagagg caaagaatca acagccaaac tgctggggct    7800
gcaagctgct gaagccaggg catgggatta agagattgt gcgttcaaac ctagggaagc     7860
ctgtgcccat ttgtcctgac tgtctgctaa catggtacac tgcatctcaa gatgtttatc    7920
tgacacaagt gtattatttc tggcttttg aattaatcta gaaaatgaaa agatggagtt     7980 gtatttgac aaaaatgttt gtactttta atgttatttg gaattttaag ttctatcagt      8040
gacttctgaa tccttagaat ggcctctttg tagaaccctg tggtatagag gagtatggcc    8100
actgccccac tatttttatt ttcttatgta agtttgcata tcagtcatga ctagtgccta    8160
gaaagcaatg tgatggtcag gatctcatga cattatattt gagtttcttt cagatcattt    8220
aggatactct taatctcact tcatcaatca aatatttttt gagtgtatgc tgtagctgaa    8280
agagtatgta cgtacgtata agactagaga gatattaagt ctcagtacac ttcctgtgcc    8340
atgttattca gctcactggt ttacaaatat aggttgtctt gtggttgtag gagcccactg    8400
taacaatact gggcagccct tttttttttt tttaattgca acaatgcaaa agccaagaaa    8460
gtataagggt cacaagtcta aacaatgaat tcttcaacag ggaaaacagc tagcttgaaa    8520
acttgctgaa aaacacaact tgtgtttatg gcatttagta ccttcaaata attggctttg    8580
cagatattgg atacccatt aaatctgaca gtctcaaatt tttcatctct tcaatcacta     8640
gtcaagaaaa atataaaaac aacaaatact tccatatgga gcattttca gagttttcta    8700 acccagtctt attttctag tcagtaaaca tttgtaaaaa tactgtttca ctaatactta     8760
ctgttaactg tcttgagaga aagaaaaat atgagagaac tattgtttgg ggaagttcaa     8820
gtgatctttc aatatcatta ctaacttctt ccactttttc caaatttga atattaacgc     8880 taaaggtgta agacttcaga tttcaaatta atctttctat atttttttaaa tttacagaat    8940 attatataac ccactgctga aaagaaaaa aatgattgtt ttagaagtta aagtcaatat     9000
tgattttaaa tataagtaat gaaggcatat ttccaataac tagtgatatg gcatcgttgc    9060
```

-continued

```
attttacagt atcttcaaaa atacagaatt tatagaataa tttctcctca tttaatattt    9120
ttcaaaatca aagttatggt ttcctcattt tactaaaatc gtattctaat tcttcattat    9180
agtaaatcta tgagcaactc cttacttcgg ttcctctgat ttcaaggcca tattttaaaa    9240
aatcaaaagg cactgtgaac tattttgaag aaaacacaac attttaatac agattgaaag    9300
gacctcttct gaagctagaa acaatctata gttatacatc ttcattaata ctgtgttacc    9360
ttttaaaata gtaattttt acattttcct gtgtaaacct aattgtggta gaaattttta    9420
ccaactctat actcaatcaa gcaaaatttc tgtatattcc ctgtggaatg tacctatgtg    9480
agtttcagaa attctcaaaa tacgtgttca aaaattctg cttttgcatc tttgggacac     9540
ctcagaaaac ttattaacaa ctgtgaatat gagaaataca gaagaaaata ataagccctc    9600
tatacataaa tgcccagcac aattcattgt taaaaaacaa ccaaacctca cactactgta    9660
tttcattatc tgtactgaaa gcaaatgctt tgtgactatt aaatgttgca catcattcat    9720
tcaaaaaaaa aaaaaaaaaa a                                              9741
```

<210> SEQ ID NO 11
<211> LENGTH: 2261
<212> TYPE: PRT
<213> ORGANISM: Homo sapiens

<400> SEQUENCE: 11

```
Met Ala Cys Trp Pro Gln Leu Arg Leu Leu Trp Lys Asn Leu Thr
 1               5                  10                  15
Phe Arg Arg Arg Gln Thr Cys Gln Leu Leu Glu Val Ala Trp Pro
                20                  25                  30
Leu Phe Ile Phe Leu Ile Leu Ile Ser Val Arg Leu Ser Tyr Pro Pro
                35                  40                  45
Tyr Glu Gln His Glu Cys His Phe Pro Asn Lys Ala Met Pro Ser Ala
        50                  55                  60
Gly Thr Leu Pro Trp Val Gln Gly Ile Ile Cys Asn Ala Asn Asn Pro
65                  70                  75                  80
Cys Phe Arg Tyr Pro Thr Pro Gly Glu Ala Pro Gly Val Val Gly Asn
                85                  90                  95
Phe Asn Lys Ser Ile Val Ala Arg Leu Phe Ser Asp Ala Arg Arg Leu
                100                 105                 110
Leu Leu Tyr Ser Gln Lys Asp Thr Ser Met Lys Asp Met Arg Lys Val
            115                 120                 125
Leu Arg Thr Leu Gln Gln Ile Lys Lys Ser Ser Asn Leu Lys Leu
        130                 135                 140
Gln Asp Phe Leu Val Asp Asn Glu Thr Phe Ser Gly Phe Leu Tyr His
145                 150                 155                 160
Asn Leu Ser Leu Pro Lys Ser Thr Val Asp Lys Met Leu Arg Ala Asp
                165                 170                 175
Val Ile Leu His Lys Val Phe Leu Gln Gly Tyr Gln Leu His Leu Thr
            180                 185                 190
Ser Leu Cys Asn Gly Ser Lys Ser Glu Glu Met Ile Gln Leu Gly Asp
        195                 200                 205
Gln Glu Val Ser Glu Leu Cys Gly Leu Pro Arg Glu Lys Leu Ala Ala
    210                 215                 220
Ala Glu Arg Val Leu Arg Ser Asn Met Asp Ile Leu Lys Pro Ile Leu
225                 230                 235                 240
Arg Thr Leu Asn Ser Thr Ser Pro Phe Pro Ser Lys Glu Leu Ala Glu
                245                 250                 255
```

```
Ala Thr Lys Thr Leu Leu His Ser Leu Gly Thr Leu Ala Gln Glu Leu
            260                 265                 270
Phe Ser Met Arg Ser Trp Ser Asp Met Arg Gln Glu Val Met Phe Leu
        275                 280                 285
Thr Asn Val Asn Ser Ser Ser Ser Thr Gln Ile Tyr Gln Ala Val
    290                 295                 300
Ser Arg Ile Val Cys Gly His Pro Glu Gly Gly Leu Lys Ile Lys
305                 310                 315                 320
Ser Leu Asn Trp Tyr Glu Asp Asn Asn Tyr Lys Ala Leu Phe Gly Gly
                325                 330                 335
Asn Gly Thr Glu Glu Asp Ala Glu Thr Phe Tyr Asp Asn Ser Thr Thr
            340                 345                 350
Pro Tyr Cys Asn Asp Leu Met Lys Asn Leu Glu Ser Ser Pro Leu Ser
        355                 360                 365
Arg Ile Ile Trp Lys Ala Leu Lys Pro Leu Leu Val Gly Lys Ile Leu
    370                 375                 380
Tyr Thr Pro Asp Thr Pro Ala Thr Arg Gln Val Met Ala Glu Val Asn
385                 390                 395                 400
Lys Thr Phe Gln Glu Leu Ala Val Phe His Asp Leu Glu Gly Met Trp
                405                 410                 415
Glu Glu Leu Ser Pro Lys Ile Trp Thr Phe Met Glu Asn Ser Gln Glu
            420                 425                 430
Met Asp Leu Val Arg Met Leu Leu Asp Ser Arg Asp Asn Asp His Phe
        435                 440                 445
Trp Glu Gln Gln Leu Asp Gly Leu Asp Trp Thr Ala Gln Asp Ile Val
    450                 455                 460
Ala Phe Leu Ala Lys His Pro Glu Asp Val Gln Ser Ser Asn Gly Ser
465                 470                 475                 480
Val Tyr Thr Trp Arg Glu Ala Phe Asn Glu Thr Asn Gln Ala Ile Arg
                485                 490                 495
Thr Ile Ser Arg Phe Met Glu Cys Val Asn Leu Asn Lys Leu Glu Pro
            500                 505                 510
Ile Ala Thr Glu Val Trp Leu Ile Asn Lys Ser Met Glu Leu Leu Asp
        515                 520                 525
Glu Arg Lys Phe Trp Ala Gly Ile Val Phe Thr Gly Ile Thr Pro Gly
    530                 535                 540
Ser Ile Glu Leu Pro His His Val Lys Tyr Lys Ile Arg Met Asp Ile
545                 550                 555                 560
Asp Asn Val Glu Arg Thr Asn Lys Ile Lys Asp Gly Tyr Trp Asp Pro
                565                 570                 575
Gly Pro Arg Ala Asp Pro Phe Glu Asp Met Arg Tyr Val Trp Gly Gly
            580                 585                 590
Phe Ala Tyr Leu Gln Asp Val Val Glu Gln Ala Ile Ile Arg Val Leu
        595                 600                 605
Thr Gly Thr Glu Lys Lys Thr Gly Val Tyr Met Gln Gln Met Pro Tyr
    610                 615                 620
Pro Cys Tyr Val Asp Asp Ile Phe Leu Arg Val Met Ser Arg Ser Met
625                 630                 635                 640
Pro Leu Phe Met Thr Leu Ala Trp Ile Tyr Ser Val Ala Val Ile Ile
                645                 650                 655
Lys Gly Ile Val Tyr Glu Lys Glu Ala Arg Leu Lys Glu Thr Met Arg
            660                 665                 670
```

-continued

```
Ile Met Gly Leu Asp Asn Ser Ile Leu Trp Phe Ser Trp Phe Ile Ser
            675                 680                 685
Ser Leu Ile Pro Leu Val Ser Ala Gly Leu Leu Val Val Ile Leu
        690                 695                 700
Lys Leu Gly Asn Leu Leu Pro Tyr Ser Asp Pro Ser Val Phe Val
705                 710                 715                 720
Phe Leu Ser Val Phe Ala Val Val Thr Ile Leu Gln Cys Phe Leu Ile
                725                 730                 735
Ser Thr Leu Phe Ser Arg Ala Asn Leu Ala Ala Ala Cys Gly Gly Ile
            740                 745                 750
Ile Tyr Phe Thr Leu Tyr Leu Pro Tyr Val Leu Cys Val Ala Trp Gln
            755                 760                 765
Asp Tyr Val Gly Phe Thr Leu Lys Ile Phe Ala Ser Leu Leu Ser Pro
770                 775                 780
Val Ala Phe Gly Phe Gly Cys Glu Tyr Phe Ala Leu Phe Glu Glu Gln
785                 790                 795                 800
Gly Ile Gly Val Gln Trp Asp Asn Leu Phe Glu Ser Pro Val Glu Glu
                805                 810                 815
Asp Gly Phe Asn Leu Thr Thr Ser Val Ser Met Met Leu Phe Asp Thr
            820                 825                 830
Phe Leu Tyr Gly Val Met Thr Trp Tyr Ile Glu Ala Val Phe Pro Gly
        835                 840                 845
Gln Tyr Gly Ile Pro Arg Pro Trp Tyr Phe Pro Cys Thr Lys Ser Tyr
850                 855                 860
Trp Phe Gly Glu Glu Ser Asp Glu Lys Ser His Pro Gly Ser Asn Gln
865                 870                 875                 880
Lys Arg Ile Ser Glu Ile Cys Met Glu Glu Pro Thr His Leu Lys
                885                 890                 895
Leu Gly Val Ser Ile Gln Asn Leu Val Lys Val Tyr Arg Asp Gly Met
            900                 905                 910
Lys Val Ala Val Asp Gly Leu Ala Leu Asn Phe Tyr Glu Gly Gln Ile
        915                 920                 925
Thr Ser Phe Leu Gly His Asn Gly Ala Gly Lys Thr Thr Thr Met Ser
930                 935                 940
Ile Leu Thr Gly Leu Phe Pro Pro Thr Ser Gly Thr Ala Tyr Ile Leu
945                 950                 955                 960
Gly Lys Asp Ile Arg Ser Glu Met Ser Thr Ile Arg Gln Asn Leu Gly
                965                 970                 975
Val Cys Pro Gln His Asn Val Leu Phe Asp Met Leu Thr Val Glu Glu
            980                 985                 990
His Ile Trp Phe Tyr Ala Arg Leu  Lys Gly Leu Ser Glu  Lys His Val
        995                 1000                1005
Lys Ala  Glu Met  Glu Gln Met  Ala Leu Asp Val Gly  Leu Pro Ser
    1010            1015                1020
Ser Lys  Leu Lys Ser Lys Thr  Ser Gln Leu Ser Gly  Gly Met Gln
    1025            1030                1035
Arg Lys  Leu Ser Val Ala Leu  Ala Phe Val Gly Gly  Ser Lys Val
    1040            1045                1050
Val Ile  Leu Asp Glu Pro Thr  Ala Gly Val Asp Pro  Tyr Ser Arg
    1055            1060                1065
Arg Gly  Ile Trp Glu Leu Leu  Leu Lys Tyr Arg Gln  Gly Arg Thr
    1070            1075                1080
Ile Ile  Leu Ser Thr His His  Met Asp Glu Ala Asp  Val Leu Gly
```

```
           1085                1090                1095

Asp Arg Ile Ala Ile Ile Ser His Gly Lys Leu Cys Cys Val Gly
        1100                1105                1110

Ser Ser Leu Phe Leu Lys Asn Gln Leu Gly Thr Gly Tyr Tyr Leu
        1115                1120                1125

Thr Leu Val Lys Lys Asp Val Glu Ser Ser Leu Ser Ser Cys Arg
        1130                1135                1140

Asn Ser Ser Ser Thr Val Ser Tyr Leu Lys Lys Glu Asp Ser Val
        1145                1150                1155

Ser Gln Ser Ser Ser Asp Ala Gly Leu Gly Ser Asp His Glu Ser
        1160                1165                1170

Asp Thr Leu Thr Ile Asp Val Ser Ala Ile Ser Asn Leu Ile Arg
        1175                1180                1185

Lys His Val Ser Glu Ala Arg Leu Val Glu Asp Ile Gly His Glu
        1190                1195                1200

Leu Thr Tyr Val Leu Pro Tyr Glu Ala Ala Lys Glu Gly Ala Phe
        1205                1210                1215

Val Glu Leu Phe His Glu Ile Asp Asp Arg Leu Ser Asp Leu Gly
        1220                1225                1230

Ile Ser Ser Tyr Gly Ile Ser Glu Thr Thr Leu Glu Glu Ile Phe
        1235                1240                1245

Leu Lys Val Ala Glu Glu Ser Gly Val Asp Ala Glu Thr Ser Asp
        1250                1255                1260

Gly Thr Leu Pro Ala Arg Arg Asn Arg Arg Ala Phe Gly Asp Lys
        1265                1270                1275

Gln Ser Cys Leu Arg Pro Phe Thr Glu Asp Asp Ala Ala Asp Pro
        1280                1285                1290

Asn Asp Ser Asp Ile Asp Pro Glu Ser Arg Glu Thr Asp Leu Leu
        1295                1300                1305

Ser Gly Met Asp Gly Lys Gly Ser Tyr Gln Val Lys Gly Trp Lys
        1310                1315                1320

Leu Thr Gln Gln Gln Phe Val Ala Leu Leu Trp Lys Arg Leu Leu
        1325                1330                1335

Ile Ala Arg Arg Ser Arg Lys Gly Phe Phe Ala Gln Ile Val Leu
        1340                1345                1350

Pro Ala Val Phe Val Cys Ile Ala Leu Val Phe Ser Leu Ile Val
        1355                1360                1365

Pro Pro Phe Gly Lys Tyr Pro Ser Leu Glu Leu Gln Pro Trp Met
        1370                1375                1380

Tyr Asn Glu Gln Tyr Thr Phe Val Ser Asn Asp Ala Pro Glu Asp
        1385                1390                1395

Thr Gly Thr Leu Glu Leu Leu Asn Ala Leu Thr Lys Asp Pro Gly
        1400                1405                1410

Phe Gly Thr Arg Cys Met Glu Gly Asn Pro Ile Pro Asp Thr Pro
        1415                1420                1425

Cys Gln Ala Gly Glu Glu Glu Trp Thr Thr Ala Pro Val Pro Gln
        1430                1435                1440

Thr Ile Met Asp Leu Phe Gln Asn Gly Asn Trp Thr Met Gln Asn
        1445                1450                1455

Pro Ser Pro Ala Cys Gln Cys Ser Ser Asp Lys Ile Lys Lys Met
        1460                1465                1470

Leu Pro Val Cys Pro Pro Gly Ala Gly Gly Leu Pro Pro Pro Gln
        1475                1480                1485
```

-continued

```
Arg Lys Gln Asn Thr Ala Asp Ile Leu Gln Asp Leu Thr Gly Arg
1490                1495                1500

Asn Ile Ser Asp Tyr Leu Val Lys Thr Tyr Val Gln Ile Ile Ala
1505                1510                1515

Lys Ser Leu Lys Asn Lys Ile Trp Val Asn Glu Phe Arg Tyr Gly
1520                1525                1530

Gly Phe Ser Leu Gly Val Ser Asn Thr Gln Ala Leu Pro Pro Ser
1535                1540                1545

Gln Glu Val Asn Asp Ala Thr Lys Gln Met Lys Lys His Leu Lys
1550                1555                1560

Leu Ala Lys Asp Ser Ser Ala Asp Arg Phe Leu Asn Ser Leu Gly
1565                1570                1575

Arg Phe Met Thr Gly Leu Asp Thr Arg Asn Asn Val Lys Val Trp
1580                1585                1590

Phe Asn Asn Lys Gly Trp His Ala Ile Ser Ser Phe Leu Asn Val
1595                1600                1605

Ile Asn Asn Ala Ile Leu Arg Ala Asn Leu Gln Lys Gly Glu Asn
1610                1615                1620

Pro Ser His Tyr Gly Ile Thr Ala Phe Asn His Pro Leu Asn Leu
1625                1630                1635

Thr Lys Gln Gln Leu Ser Glu Val Ala Pro Met Thr Thr Ser Val
1640                1645                1650

Asp Val Leu Val Ser Ile Cys Val Ile Phe Ala Met Ser Phe Val
1655                1660                1665

Pro Ala Ser Phe Val Val Phe Leu Ile Gln Glu Arg Val Ser Lys
1670                1675                1680

Ala Lys His Leu Gln Phe Ile Ser Gly Val Lys Pro Val Ile Tyr
1685                1690                1695

Trp Leu Ser Asn Phe Val Trp Asp Met Cys Asn Tyr Val Val Pro
1700                1705                1710

Ala Thr Leu Val Ile Ile Ile Phe Ile Cys Phe Gln Gln Lys Ser
1715                1720                1725

Tyr Val Ser Ser Thr Asn Leu Pro Val Leu Ala Leu Leu Leu Leu
1730                1735                1740

Leu Tyr Gly Trp Ser Ile Thr Pro Leu Met Tyr Pro Ala Ser Phe
1745                1750                1755

Val Phe Lys Ile Pro Ser Thr Ala Tyr Val Val Leu Thr Ser Val
1760                1765                1770

Asn Leu Phe Ile Gly Ile Asn Gly Ser Val Ala Thr Phe Val Leu
1775                1780                1785

Glu Leu Phe Thr Asp Asn Lys Leu Asn Asn Ile Asn Asp Ile Leu
1790                1795                1800

Lys Ser Val Phe Leu Ile Phe Pro His Phe Cys Leu Gly Arg Gly
1805                1810                1815

Leu Ile Asp Met Val Lys Asn Gln Ala Met Ala Asp Ala Leu Glu
1820                1825                1830

Arg Phe Gly Glu Asn Arg Phe Val Ser Pro Leu Ser Trp Asp Leu
1835                1840                1845

Val Gly Arg Asn Leu Phe Ala Met Ala Val Glu Gly Val Val Phe
1850                1855                1860

Phe Leu Ile Thr Val Leu Ile Gln Tyr Arg Phe Phe Ile Arg Pro
1865                1870                1875
```

```
Arg Pro Val Asn Ala Lys Leu Ser Pro Leu Asn Asp Glu Asp Glu
    1880             1885             1890

Asp Val Arg Arg Glu Arg Gln Arg Ile Leu Asp Gly Gly Gly Gln
    1895             1900             1905

Asn Asp Ile Leu Glu Ile Lys Glu Leu Thr Lys Ile Tyr Arg Arg
    1910             1915             1920

Lys Arg Lys Pro Ala Val Asp Arg Ile Cys Val Gly Ile Pro Pro
    1925             1930             1935

Gly Glu Cys Phe Gly Leu Leu Gly Val Asn Gly Ala Gly Lys Ser
    1940             1945             1950

Ser Thr Phe Lys Met Leu Thr Gly Asp Thr Thr Val Thr Arg Gly
    1955             1960             1965

Asp Ala Phe Leu Asn Arg Asn Ser Ile Leu Ser Asn Ile His Glu
    1970             1975             1980

Val His Gln Asn Met Gly Tyr Cys Pro Gln Phe Asp Ala Ile Thr
    1985             1990             1995

Glu Leu Leu Thr Gly Arg Glu His Val Glu Phe Phe Ala Leu Leu
    2000             2005             2010

Arg Gly Val Pro Glu Lys Glu Val Gly Lys Val Gly Glu Trp Ala
    2015             2020             2025

Ile Arg Lys Leu Gly Leu Val Lys Tyr Gly Glu Lys Tyr Ala Gly
    2030             2035             2040

Asn Tyr Ser Gly Gly Asn Lys Arg Lys Leu Ser Thr Ala Met Ala
    2045             2050             2055

Leu Ile Gly Gly Pro Pro Val Val Phe Leu Asp Glu Pro Thr Thr
    2060             2065             2070

Gly Met Asp Pro Lys Ala Arg Arg Phe Leu Trp Asn Cys Ala Leu
    2075             2080             2085

Ser Val Val Lys Glu Gly Arg Ser Val Val Leu Thr Ser His Ser
    2090             2095             2100

Met Glu Glu Cys Glu Ala Leu Cys Thr Arg Met Ala Ile Met Val
    2105             2110             2115

Asn Gly Arg Phe Arg Cys Leu Gly Ser Val Gln His Leu Lys Asn
    2120             2125             2130

Arg Phe Gly Asp Gly Tyr Thr Ile Val Val Arg Ile Ala Gly Ser
    2135             2140             2145

Asn Pro Asp Leu Lys Pro Val Gln Asp Phe Phe Gly Leu Ala Phe
    2150             2155             2160

Pro Gly Ser Val Pro Lys Glu Lys His Arg Asn Met Leu Gln Tyr
    2165             2170             2175

Gln Leu Pro Ser Ser Leu Ser Ser Leu Ala Arg Ile Phe Ser Ile
    2180             2185             2190

Leu Ser Gln Ser Lys Lys Arg Leu His Ile Glu Asp Tyr Ser Val
    2195             2200             2205

Ser Gln Thr Thr Leu Asp Gln Val Phe Val Asn Phe Ala Lys Asp
    2210             2215             2220

Gln Ser Asp Asp Asp His Leu Lys Asp Leu Ser Leu His Lys Asn
    2225             2230             2235

Gln Thr Val Val Asp Val Ala Val Leu Thr Ser Phe Leu Gln Asp
    2240             2245             2250

Glu Lys Val Lys Glu Ser Tyr Val
    2255             2260
```

```
<210> SEQ ID NO 12
<211> LENGTH: 26
<212> TYPE: DNA
<213> ORGANISM: Homo sapiens

<400> SEQUENCE: 12
ttgccgtcga ctgttttggg tagttt                                          26

<210> SEQ ID NO 13
<211> LENGTH: 25
<212> TYPE: DNA
<213> ORGANISM: Homo sapiens

<400> SEQUENCE: 13
gccctgtcga ccggctctgt tggtg                                           25

<210> SEQ ID NO 14
<211> LENGTH: 29
<212> TYPE: DNA
<213> ORGANISM: Homo sapiens

<400> SEQUENCE: 14
tcgcccgttt aggcttgggc gcccggctc                                       29

<210> SEQ ID NO 15
<211> LENGTH: 29
<212> TYPE: DNA
<213> ORGANISM: Homo sapiens

<400> SEQUENCE: 15
cagaggccgg gaggcttggg cgggaggga                                       29

<210> SEQ ID NO 16
<211> LENGTH: 28
<212> TYPE: DNA
<213> ORGANISM: Homo sapiens

<400> SEQUENCE: 16
cgtgctttct gctgaggatg cgaactac                                        28

<210> SEQ ID NO 17
<211> LENGTH: 26
<212> TYPE: DNA
<213> ORGANISM: Homo sapiens

<400> SEQUENCE: 17
cggctcctca cggctttctg ctgagt                                          26

<210> SEQ ID NO 18
<211> LENGTH: 24
<212> TYPE: DNA
<213> ORGANISM: Homo sapiens

<400> SEQUENCE: 18
gcctcctttc tgctgagtga ctga                                            24

<210> SEQ ID NO 19
<211> LENGTH: 34
<212> TYPE: DNA
<213> ORGANISM: Homo sapiens

<400> SEQUENCE: 19
ctttgtgtga tagtaaacta ctgcgctcgg tgca                                 34
```

```
<210> SEQ ID NO 20
<211> LENGTH: 20
<212> TYPE: DNA
<213> ORGANISM: Homo sapiens

<400> SEQUENCE: 20
actcccaagc tttgtcgtgg                                                      20
```

REGULATORY NUCLEIC ACID FOR THE ABC1 GENE, MOLECULES MODIFYING ITS ACTIVITY AND THERAPEUTIC USES

The instant application claims benefit of U.S. provisional application 60/201,280 filed 2 May 2000.

BACKGROUND

The present invention concerns a nucleic acid which is capable of regulating the transcription of the ABC1 gene, which is a causal gene for pathologies linked to a dysfunctioning of cholesterol metabolism, inducing diseases such as atherosclerosis.

The invention also relates to nucleotide constructs comprising a polynucleotide which encodes a polypeptide or a nucleic acid of interest, placed under the control of a regulatory nucleic acid for the ABC1 gene.

The invention also relates to recombinant vectors, transformed host cells and non-human transgenic mammals comprising a nucleic acid which regulates the transcription of the ABC1 gene or an above-mentioned nucleotide construct, as well as to methods for screening molecules or substances which are capable of modifying the activity of the regulatory nucleic acid for the ABC1 gene.

The invention also relates to methods for detecting an impairment in the transcription of the ABC1 gene in an at-risk individual.

A subject of the invention is also substances or molecules which modify the activity of the nucleic acid which regulates the transcription of the ABC1 gene, as well as pharmaceutical compositions containing such substances or such molecules.

High density lipoproteins (HDLs) are one of the four major classes of lipoprotein which circulate in the blood plasma.

These lipoproteins are involved in various metabolic pathways, such as lipid transport, bile acid formation, steroidogenesis or cell proliferation, and also interfere with plasmatic proteinase systems.

HDLs are perfect free cholesterol acceptors, and in combination with cholesterol ester transfer proteins (CETP), lipoprotein lipase (LPL), hepatic lipase (HL) and lecithin-cholesterol acyltransferase (LCAT), play a major role in the reverse transport of cholesterol, i.e. the transport of excess cholesterol in the peripheral cells to the liver, for its removal from the body in the form of bile acid.

It has been demonstrated that the HDLs generally play a central role in the transport of cholesterol from the peripheral tissues to the liver.

Various diseases linked to an HDL deficiency have been described, including Tangier disease, HDL deficiency and LCAT deficiency.

The deficiency involved in Tangier disease is linked to a cellular defect in the translocation of cellular cholesterol, which leads to a degradation of the HDLs.

In Tangier disease, this cellular defect leads to a disruption of lipoprotein metabolism. The HDL particles in Tangier disease, which do not incorporate cholesterol from the peripheral cells, and which are not able to be correctly metabolized, are rapidly eliminated from the body. The plasma HDL concentration in these patients is thus extremely reduced, and the HDLs no longer contribute to the return of cholesterol to the liver. This cholesterol accumulates in these peripheral cells and causes characteristic clinical manifestations such as the formation of orange-colored tonsils. Furthermore, other lipoprotein disruptions such as an overproduction of triglycerides and an increased synthesis and intracellular catabolism of phospholipids are generally observed.

Tangier disease, the symptoms of which have been described above, is classified among the familial conditions linked to metabolism of the HDLs which are commonly detected in patients affected by coronary diseases.

Numerous studies have shown that a reduced level of HDL cholesterol is a risk factor which is useful for detecting a coronary condition.

In this context, syndromes linked to HDL deficiencies have been of increasing interest for the past decade, since they make it possible to increase the understanding of the role of HDLs in atherogenesis.

Several mutations in the apo A-1 gene have been characterized. These mutations are rare and can lead to an absence of production of apo A-1.

Mutation in the genes encoding lipoprotein lipase (LPL) or its activator apoC-II are associated with severe hypertriglyceridemias and substantially reduced levels of HDL-c.

Mutations in the gene encoding the enzyme lecithin-cholesterol acyltransferase (LCAT) are also associated with severe HDL deficiency.

Furthermore, dysfunctions in the reverse transport of cholesterol might be induced by physiological deficiencies affecting at least one of the steps for transporting stored cholesterol from the intracellular vesicles toward the membrane surface, where it is accepted by the HDLs.

Recently, a study was carried out on the segregation of various allelic forms of 343 microsatellite markers distributed over the entire genome and distant from each other by 10.3 cM on average.

The linkage study was carried out on a family which had been well characterized over eleven generations, in which many members are affected by Tangier disease, the family comprising five consanguineous lines.

This study made it possible to identify a region located in the 9q31 locus of human chromosome 9 which is statistically linked to the condition (Rust S. et al., Nature Genetics Vol. 20, September 1998, pages 96-98).

However, the study by Rust et al. only characterizes a wide region of the genome in which impairments are likely to be associated with Tangier disease. The study simply stated that the relevant 9q31-34 region contains ESTs, but no known gene.

It has been shown that a region spanning 1 cM, situated in the 9q31 locus in humans, is generally associated with familial HDL deficiencies (Rust et al., 1999).

Furthermore, it has been shown that a gene encoding a protein of the family of ABC transporters, which is located precisely in the 1 cM region of the 9q31 locus, is involved in pathologies linked to a deficiency in the reverse transport of cholesterol.

For example, it has been shown that the gene encoding the ABC-1 transporter is mutated in patients with affected reverse transport of cholesterol, such as in patients suffering from Tangier disease.

The ABC ("ATP-binding cassette") transporter proteins constitute a family of proteins which are extremely conserved in evolution, from bacteria to humans.

The ABC transporter proteins are involved in the membrane transport of various substrates, for example, ions, amino acids, peptides, sugars, vitamins or steroid hormones.

The characterization of the complete amino acid sequence of some ABC transporters has made it possible to determine that these proteins have a common general structure, for example, two nucleotide-binding folds (Nucleotide Binding Fold or NBF) with moieties of Walker A type and Walker B type, as well as two transmembrane domains, each of the transmembrane domains consisting of six helices. The specificity of the ABC transporters for the various transported molecules appears to be determined by the structure of the transmembrane domains, whereas the energy required for the transport activity is provided by degrading ATP at the NBF fold.

Several of the ABC transporter proteins which have been identified in humans have been associated with various diseases.

For example, cystic fibrosis is caused by mutations in the CFTLR (cystic fibrosis transmembrane conductance regulator) gene.

Moreover, some multi-drug resistance phenotypes in tumor cells have been associated with mutations in the gene encoding the MDR (multi-drug resistance) protein which also has an ABC transporter structure.

Other ABC transporters have been associated with neuronal and tumor conditions (U.S. Pat. No. 5,858,719), or potentially implicated in diseases caused by an impairment of the homeostasis of metals, for example, the ABC-3 protein.

Similarly, another ABC transporter, referred to as PFIC2, seems to be involved in a form of progressive familial intrahepatic cholestasis, this protein being potentially responsible, in humans, for the export of bile salts.

In 1994, a cDNA encoding a novel mouse ABC transporter was identified and referred to as ABC1 (Luciani et al., 1994). This protein is characteristic of the ABC transporters in that it has a symmetrical structure comprising two transmembrane domains linked to a highly hydrophobic segment and to two NBF moieties.

In humans, a partial cDNA comprising the entire open reading frame of the human ABC1 transporter has been identified (Lanigmann et al., 1999).

It has also been shown that the gene encoding the human ABC1 protein is expressed in various tissues, and more particularly at high levels in the placenta, the liver, the lungs, the adrenal glands and the fetal tissues.

These authors have also shown that the expression of the gene encoding the human ABC1 protein is induced during the differentiation of monocytes into macrophages in vitro. Furthermore, the expression of the gene encoding the ABC1 protein is increased when human macrophages are incubated in the presence of acetylated low-density lipoproteins (AcLDLs).

The work of Rust S. et al., 1999, Brooks-Wilson A. et al., 1999, Bodzioch M. et al., 1999, Remaley A. et al., 1999 and of Marcil M. et al., 1999 has shown that patients suffering from Tangier disease and from HDL deficiencies (FHD; familial HDL deficiency) have a mutated ABC1 gene. Several mutations, which are distributed in various regions of the ABC1 gene, have been identified in the genome of various patients, for example, of patients with a severe form of the disease associated with coronary disorders. Moreover, diverse polymorphisms have been found, both in the exons and in the introns of the ABC1 gene, in patients suffering from milder forms of the disease, indicating that these patients carry specific alleles of the gene, which are distinct from the "wild-type" allele(s).

Although the expression of the human ABC1 gene seems to be regulated according to the type of cell or to the metabolic situation of a given cell type, the sequence(s) which make(s) it possible to regulate this gene were not known.

Thus, there exists a need in the state of the art to identify these regulatory sequences, for the two principal reasons below:

a) These sequences are likely to be mutated in patients suffering from a pathology linked to a deficiency in cholesterol transport, for example, in patients suffering from Tangier disease, or likely to develop such pathologies.

The characterization of the regulatory sequences of the human ABC1 gene would make it possible, firstly, to detect mutations in patients, and, for example, also to diagnose the individuals who belong to at-risk familial groups. In addition, the isolation of these regulatory sequences would make it possible to complement the mutated sequence with a functional sequence capable of overcoming the metabolic dysfunctions induced by the mutation(s) diagnosed, through the construction of targeted therapeutic means, such as means intended for gene therapy.

b) The characterization of the regulatory sequences of the ABC1 gene would place at the disposal of persons skilled in the art means capable of allowing the construction, by genetic engineering, and then the expression, of given genes in the cell types in which the ABC1 gene is expressed.

c) Moreover, some portions of the regulatory sequences of the ABC1 gene might constitute high expression-level constitutive promoter sequences, which are liable to enable the construction of novel means for expressing given sequences in cells, completing an already existing set of means.

To date, despite the efforts undertaken, the regulatory sequences of the ABC1 gene have remained totally unknown.

The inventors have henceforth isolated and then sequenced a genomic DNA comprising the first two exons of the ABC1 gene (respectively exon 1A and exon 1B), as well as a non-transcribed region of approximately 2.9 kb, which is located on the 5' side of exon 1A, and which comprises regulation signals for the ABC1 gene.

BRIEF DESCRIPTION OF THE DRAWINGS

FIG. 1: illustrates a portion of the sequence SEQ ID No. 3, which starts with the nucleotide at position 1 of the sequence SEQ ID No. 3. The position of each of the characteristic binding moieties for various transcription factors is represented by boxes, the designation of the transcription vector specific for the corresponding sequence being indicated above the nucleotide sequence.

FIG. 3: RAW 264.7 cells were transfected with wild type construct (p200-L) or mutant LXR construct (p200-LXRm) along with a β-galactosidase expression plasmid. Three hours after transfection, cells were refed with fresh media containing 10% FCS. Sixteen hours later, cells were washed with PBS and replaced with DMEM media containing 0.1% BSA and added 50 µg/ml cholesterol, 2 µg/ml 22(R)-HOch, 10 µM 9CRA or, 2 µg/ml 22(R)-HOch plus 10 µM 9CRA for 24 hours. Cell lysates were analyzed for luciferase and β-galactosidase activity. Luciferase values were normalized to β-galactosidase and expressed as mean±SEM.

FIG. 6A: illustrates the probes used for the gel shift analysis. Fragment A (100 bp) includes binding motifs for Sp1 and AP1 and the E-box. Fragment EB (27 bp) contains the E-box and fragment EBm (not shown) contains a mutated E-box. In panels B and C, the labeled fragments (fragments A, EB or EBm) used for the gel shift study are shown on top of each gel. Incubation of the radiolabelled probe with RAW cell nuclear extract (NE) is indicated (+);

FIG. 6B: shows the gel-shift analysis performed by incubating RAW cell nuclear extracts with radiolabelled Fragment A (left), EB (middle) or EBm (right) in the presence or absence of specific competitors (unlabelled fragment A, EB or EBm);

FIG. 6C: shows supershift analysis of Fragments A or EB with antibodies specific to the amino (N) or carboxyl (C) ends of USF1 and USF2. Arrows indicate the position of probe complexed with protein and arrows with an asterisk indicates the position of antibody-supershifted complex.

DETAILED DESCRIPTION OF THE INVENTION

General Definitions

Figure 2A:
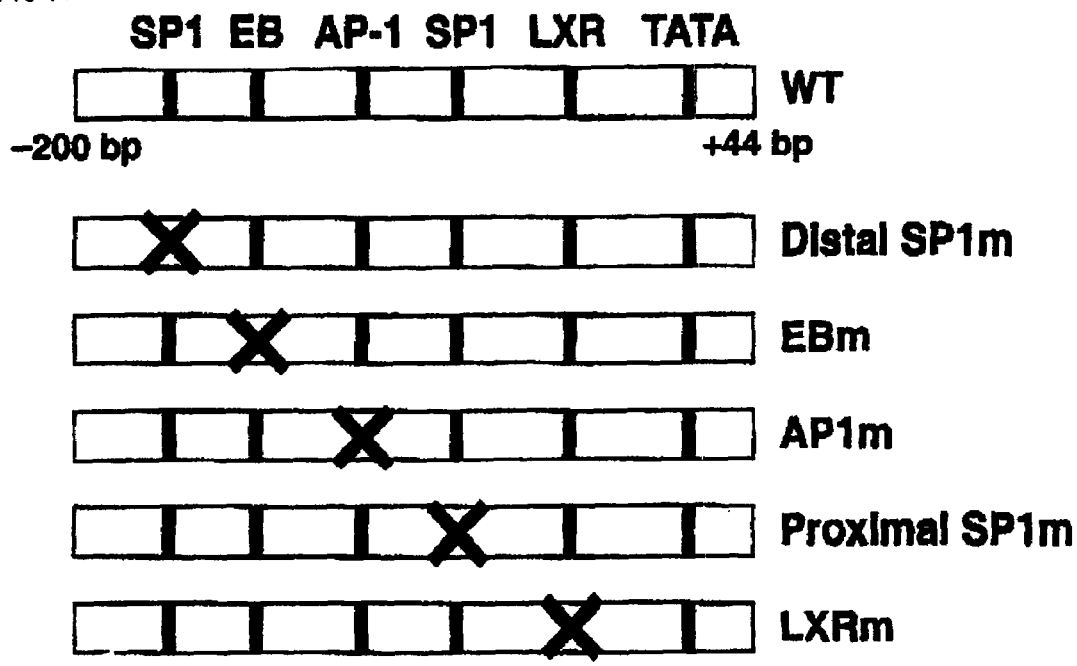
FIG. 2A: is a schematic illustration that shows the location of the point mutations introduced into the −200 bp promoter region of the human ABC1 gene.

For the purpose of the present invention, the term "isolated" refers to a biological material (nucleic acid or protein) which has been abstracted from its environment of origin (the environment in which it is naturally located).

For example, a polynucleotide present in the natural state in a plant or an animal is not isolated. The same polynucleotide separated from the adjacent nucleic acids among which it is naturally inserted in the genome of the plant or the animal is considered to be "isolated".

Such a polynucleotide can be included in a vector and/or such a polynucleotide can be included in a composition, and can remain, however, in the isolated state, because the vector or the composition does not constitute its natural environment.

The term "purified" does not require the material to be present in a form of absolute purity, excluding the presence of other compounds. It is, rather, a relative definition.

A polynucleotide is in the "purified" state after purification of the starting material, or after purification of the natural material, wherein impurities are present after the purification in an amount of at least one order of magnitude less than the amount of impurities before the purification. In one embodiment, impurities are present after the purification in an amount of 2 or 3 orders of magnitude less than the amount of impurities before the purification. In another embodiment, impurities are present after the purification in an amount of 4 or 5 orders of magnitude less than the amount of impurities before the purification.

For the purposes of the present description, the expression "nucleotide sequence" can be used to refer indiscriminately to a polynucleotide or a nucleic acid. The expression "nucleotide sequence" encompasses the genetic material itself, and is thus not restricted to the information concerning its sequence.

The terms "nucleic acid", "polynucleotide", "oligonucleotide" and "nucleotide sequence" encompass RNA, DNA or cDNA sequences, or DNA/RNA hybrid sequences of more than one nucleotide, indiscriminately in the single chain form or in the duplex form.

The term "nucleotide" refers to both natural nucleotides (A, T, G, C) and modified nucleotides, which comprise at least one modification such as (1) a purine analog, (2) a pyrimidine analog or (3) a similar sugar, examples of such modified nucleotides being described for example, in PCT application No. WO 95/04 064.

For the purposes of the present invention, a first polynucleotide is considered as being "complementary" to a second polynucleotide when each base of the first nucleotide is paired with the complementary base of the second polynucleotide, the orientation of which is inversed. The complementary bases are A and T (or A and U), or C and G.

"Variant" of a nucleic acid according to the invention will be intended to mean a nucleic acid which differs by one or more bases with respect to the reference polynucleotide. A variant nucleic acid can be of natural origin, such as an allelic variant found naturally, or can also be an unnatural variant obtained for example, by mutagenesis techniques.

In general, the differences between the reference nucleic acid and the variant nucleic acid are small, such that the nucleotide sequences of the reference nucleic acid and of the variant nucleic acid are very close and, in many regions, identical. The nucleotide modifications present in a variant nucleic acid can be silent, which means that they do not alter the amino acid sequences encoded by said variant nucleic acid.

However, the nucleotide changes in a variant nucleic acid can also result in substitutions, additions or deletions in the polypeptide encoded by the variant nucleic acid, with respect to the peptides encoded by the reference nucleic acid. In addition, nucleotide modifications in the coding regions can produce substitutions, which may be conservative or non-conservative in the amino acid sequence.

For example, the variant nucleic acids according to the invention encode polypeptides which conserve more or less the same function or biological activity as the polypeptide of the reference nucleic acid, or the capacity to be recognized by antibodies directed against the polypeptides encoded by the initial nucleic acid.

Some variant nucleic acids will thus encode mutated forms of the polypeptides, the systematic study of which will make it possible to deduce structure-activity relationships for the proteins in question. Knowledge of these variants with respect to the disease studied is fundamental, since it makes it possible to understand the molecular cause of the pathology.

A "fragment" of a reference nucleic acid according to the invention, will be intended to mean a nucleotide sequence which is shorter in length than the nucleotide sequence of the reference nucleic acid and which comprises a nucleotide sequence which is identical to a portion of the nucleotide sequence of the reference nucleic acid. Such a "fragment" of nucleic acid according to the invention can be, if needed, included in the nucleotide sequence of a second polynucleotide different from the reference nucleic acid. The resulting nucleotide which comprises the "fragment" and the second polynucleotide may have a nucleotide sequence that is longer than, the same length as, or shorter than the nucleotide sequence of the reference nucleic acid. Such fragments comprise, or alternatively consist of, oligonucleotides of lengths ranging from 20 to 25, 30, 40, 50, 70, 80, 100, 200, 500, 1000 or 1500 consecutive nucleotides of a nucleic acid according to the invention.

"Biologically active fragment" of an acid which regulates transcription according to the invention is intended to mean a nucleic acid which is capable of modifying the transcription of a sequence of DNA placed under its control. Such a biologically active fragment comprises a basic promoter and/or a regulatory element, as defined in the present description.

"Regulatory nucleic acid" according to the invention is intended to mean a nucleic acid which activates and/or regulates the expression of a DNA sequence which is selected and placed under its control.

"Promoter" is intended to mean a DNA sequence recognized by the proteins of the cell which are involved in initiating the transcription of a gene. The basic promoter is the minimum regulatory nucleic acid which is capable of initiating the transcription of a given DNA sequence which is placed under its control. In general, the basic promoter consists a region of genomic DNA upstream of the transcription start site, where a sequence CAAT (to which one or more protein transcription factors bind), as well as, except in rare cases such as in certain housekeeping genes, the sequence TATA, or "TATA box", or a related box, are very often found. An RNA polymerase, as well as one or more transcription factors, such as "TATA" box binding proteins (or TBPs), bind to this box.

A nucleotide sequence is "placed under the control" of a regulatory nucleic acid when this regulatory nucleic acid is located, with respect to the nucleotide sequence, in such a way as to control the initiation of the transcription of the nucleotide sequence with an RNA polymerase.

For the purpose of the invention, "regulatory element" and "regulatory sequence" are intended to mean a nucleic acid comprising elements capable of modifying the transcription initiated by a basic promoter, such as binding sites for diverse transcription factors, "enhancer" sequences for increasing transcription or "silencer" sequences for inhibiting transcription.

"Enhancer" sequence is intended to mean a DNA sequence included in a regulatory nucleic acid, which is capable of increasing or of stimulating the transcription initiated by a basic promoter.

"Silencer" sequence is intended to mean a DNA sequence included in a regulatory acid, which is capable of decreasing or of inhibiting the transcription initiated by a basic a promoter.

Regulatory elements can be present outside the sequence which is located on the 5' side of the transcription start site, for example, in the introns and the exons, including in the coding sequences.

The terms "basic promoter" and "regulatory element" can be "specific for one or more tissues" if they allow the transcription of a given DNA sequence, placed under their control, such as in certain cells (for example, the cells specific for a tissue), i.e. either exclusively in the cells of certain tissues, or at different levels of transcription according to the tissues.

"Transcription factor" is intended to mean proteins which preferentially interact with regulatory elements of a regulatory nucleic acid according to the invention, and which stimulate or, on the contrary, suppress transcription. Some transcription factors are active in the form of monomers, others being active in the form of homo- or heterodimers.

The term "modification" is directed toward either a positive regulation (increase, stimulation) of transcription, or a negative regulation (decrease, inhibition, blocking) of transcription.

For the purpose of the present invention, the "percentage of identity" between two sequences of nucleotides or amino acids can be determined by comparing two optimally aligned sequences, through a comparison window.

The portion of the nucleotide sequence or polypeptide which is in the comparison window can thus comprise additions or deletions (for example, "gaps"), with respect to the reference sequence (which does not comprises these additions or these deletions), in such a way as to obtain an optimal alignment of the two sequences.

The percentage is calculated by determining the number of positions at which an identical nucleic base or amino acid residue is observed for the two sequences (nucleic or peptide) compared, then by dividing the number of positions at which there is identity between the two bases or amino acid residues by the total number of positions in the comparison window, and then by multiplying the result by 100 to obtain the percentage of sequence identity.

The optimal sequence alignment for the comparison can be carried out using a computer with the aid of known algorithms in the package from the company Wisconsin Genetics Software Package, Genetics Computer Groups (GCG), 575 Science Doctor, Madison, Wis.

By way of illustration, it will be possible to produce the percentage of sequence identity with the aid of the BLAST software (Versions BLAST 1.4.9 of March 1996, BLAST 2.0.4 of February 1998 and BLAST 2.0.6 of September 1998), using exclusively the default parameters (S. F. Altschul et al., J. Mol. Biol. 1990 215: 403-410, S. F. Altschul et al., Nucleic Acids Res. 1997 25: 3389-3402). Blast searches for sequences which are similar/homologous to a "request" sequence of reference, with the aid of the algorithm of Altschul et al. The request sequence and the databases used can be of peptide or nucleic type, any combination being possible.

For the purposes of the present invention, "high stringency hybridization conditions" are intended to mean the following conditions:

1—Membrane Competition and Prehybridization:
   Mixed: 40 µl salmon sperm DNA (10 mg/ml)
      +40 µl human placental DNA (10 mg/ml)
   Denatured for 5 min at 96° C., then immersed the mixture in ice.
   Removed the 2×SSC buffer and poured 4 ml of formamide mix into the hybridization tube containing the membranes.
   Added the mixture of the two denatured DNAs.
   Incubation at 42° C. for 5 to 6 hours, with rotation.

2—Labeled Probe Competition:
   Added 10 to 50 µl Cot I DNA to the labeled and purified probe, according to the amount of nonspecific hybridization.
   Denatured for 7 to 10 min at 95° C.
   Incubated at 65° C. for 2 to 5 hours.

3—Hybridization:
   Removed the prehybridization mix.
   Mixed 40 µl salmon sperm DNA+40 µl human placental DNA; denatured 5 min at 96° C., then immersed in ice.

Added 4 ml of formamide mix, the mixture of the two DNAs and the denatured labeled probe/Cot I DNA to the hybridization tube.

Incubated for 15 to 20 hours at 42° C., with rotation.

4—Washes:

One wash at room temperature in 2×SSC, to rinse.

Twice 5 minutes at room temperature, 2×SSC and 0.1% SDS, at 65° C.

Twice 15 minutes at 65° C., 1×SSC and 0.1% SD)S, at 65° C.

Wrapped the membranes in Saranwrap and exposed

The hybridization conditions described above are adapted to hybridization, under high stringency conditions, of a molecule of nucleic acid of variable length, from 20 nucleotides to several hundred nucleotides.

The hybridization conditions described above can be adapted as a function of the length of the nucleic acid whose hybridization is desired, or of the type of labeling chosen, according to techniques known to persons skilled in the art.

Suitable hybridization conditions may for example, be adapted according to the teaching contained in the work by Hames and Higgins (1985) or in the work by F. Ausubel et al. (1999).

For the purposes of the present invention, "transformation" is intended to mean the introduction of a nucleic acid (or of a recombinant vector) into a host cell. The term "transformation also encompasses a situation in which the genotype of a cell has been modified by an exogenous nucleic acid, and in which this cell thus transformed expresses said exogenous nucleic acid, for example, in the form of a recombinant polypeptide or in the form of a sense or antisense nucleic acid.

For the purposes of the invention, "transgenic animal" is intended to mean a nonhuman animal, such as a mammal, in which one or more cells contain a heterologous nucleic acid which has been introduced through human intervention, such as by transgenesis techniques well known to persons skilled in the art. The heterologous nucleic acid is introduced directly or indirectly into the cell or the precursor of the cell, by genetic manipulation such as microinjection or infection with a recombinant virus. The heterologous nucleic acid can be integrated into the chromosome, or can be in the form of DNA which replicates extrachromosomally.

Regulatory Nucleic Acid for the ABC1 Gene

The inventors have succeeded in isolating a regulatory nucleic acid for the human ABC1 gene from vector libraries of BAC type prepared from human genomic material.

According to the sequence analysis carried out, the inventors have determined that the nucleic acid which regulates the transcription of the ABC1 gene, when it is defined in the broadest way, consists of a polynucleotide comprising, from the 5' end toward the 3' end:

a nontranscribed region of approximately 2.9 kb located upstream of the transcription start site of the ABC1 gene;

the nucleotide sequence of the first exon of the ABC1 gene, also referred to as exon 1A;

the partial nucleotide sequence of the first intron of the ABC1 gene, also referred to under the name intron 1A; and the nucleotide sequence of the second exon of the human ABC1 gene, also referred to as exon 1B.

the partial nucleotide sequence of the second intron of the ABC1 gene, also referred under the name intron 1B;

Under a general definition, the nucleic acid which regulates the transcription of the ABC1 gene comprises all the nucleotide regions as defined above, and is identified as the sequence SEQ ID No. 1 according to the invention.

Preferentially, the nucleic acid which regulates the transcription factor of the ABC1 gene comprises all the nucleotide regions comprising nucleotide −2228 to nucleotide +108 with respect of the transcription start site of the ABC1 gene, i.e., a region comprised in nucleotides 654 to 3001 of sequence SEQ ID NO: 1.

Thus, a first subject of the invention consists of a nucleic acid comprising a polynucleotide which has at least 20 consecutive nucleotides of the nucleotide sequence SEQ ID No. 1, or a nucleic acid of complementary sequence.

The region of approximately 2.9 kb, which is located upstream of the transcription start site of the ABC1 gene, and which comprises the basic promoter and multiple regulatory elements for transcription, is also included in the sequence identified as SEQ ID No. 3 according to the invention.

More precisely, the nucleotide in position 1 of the sequence SEQ ID No. 3 is the nucleotide in position −2893, with respect to the transcription start site of the ABC1 gene.

According to a second aspect, the invention relates to a nucleic acid comprising a polynucleotide which has at least 20 consecutive nucleotides of the nucleotide sequence SEQ ID No. 3, or to a nucleic acid of complementary sequence.

As already specified above, in addition to a 5' non transcribed regulatory region, the nucleic acid which regulates the transcription of the ABC1 gene, of sequence SEQ ID No. 1, also comprises the first exon and the 5' portion of the first intron of the human ABC1 gene.

The first exon of the ABC1 gene, also referred to as exon 1A, is defined as the sequence SEQ ID No. 4.

The sequence of the intron 1a has been partially characterized. The 5' end of intron 1a is defined as the nucleotide sequence SEQ ID No. 6. The 3' end of intron 1a is defined as the sequence SEQ ID No. 7.

The second exon of the human ABC1 gene, also referred to as exon 1B, is defined as the sequence SEQ ID No. 5.

According to a third aspect, the invention relates to a nucleic acid comprising a polynucleotide which has at least 20 consecutive nucleotides of a nucleotide sequence chosen from the sequences SEQ ID No. 3 to 7, or to a nucleic acid of complementary sequence.

In some embodiments of the invention, a nucleic acid according to the invention will be in an isolated and/or purified form.

Any "biologically active" fragment of a nucleic acid as defined above also forms part of the invention.

According to another aspect, the invention concerns a nucleic acid having at least 80% nucleotide identity with a nucleic acid as defined above.

The invention also encompasses a nucleic acid that hybridizes, under high stringency conditions, with any one of the nucleic acids according to the invention.

The invention also concerns a nucleic acid having at least 80%, for example, 90%, 95% or 98%, nucleotide identity with a nucleic acid comprising at least 20 consecutive nucleotides of a polynucleotide chosen from nucleotide sequences SEQ ID No. 1, SEQ ID No. 2, SEQ ID No. 3, SEQ ID No. 4, SEQ ID No. 5, SEQ ID No. 6, SEQ ID No. 7, and SEQ ID No. 8.

Detailed Analysis of the Sequence SEQ ID NO. 3

The nucleic acid of sequence SEQ ID No. 3, included in the regulatory nucleic acid for the ABC1 gene of sequence SEQ ID No. 1, comprises the constituent elements of a basic promoter, respectively a "TATA" box and a homeobox, represented in FIG. 1.

The regulatory sequence SEQ ID No. 3 also comprises many binding sites for diverse transcription factors which are capable of positively or negatively regulating the activity of the basic promoter.

Thus, the various sequences which are characteristic of the binding sites for diverse transcription factors in the sequence SEQ ID No. 3 have been identified by the inventors, in the manner detailed below.

The sequence SEQ ID No. 3 was used as a reference sequence and processed according to the algorithms of the BLAST 2, version 2.10, software, and compared to the data listed in several databases, and the presence, as well as the location, of the various characteristic sites of the sequence SEQ ID No. 3, and, for example, the binding sites for transcription factors, were determined according to methods well known to persons skilled in the art.

Furthermore, a detailed analysis was carried out on the 1.3 kb upstream of the start site, in which a total of 1900 sequences corresponding to binding sites for transcription factors was identified during the first step of the search. After compilation and filtering as described above, only 79 binding sites, specific for 27 different transcription factors, were retained. These sites are presented in Table 1 below.

Table 1 represents the binding sites for the transcription factors identified in the 1318 nt in the 3' portion of the sequence SEQ ID No. 3 according to the invention.

The positions of the start and end nucleotildes of each of the binding sites for transcription factors are referred with reference to the numbering of the nucleotides of the sequence SEQ ID No. 3, as represented in FIG. 1 (+strand) or of the nucleotides on the complementary sequence of the sequence SEQ ID No. 3 (−strand).

TABLE 1

| Transcription factor | Start | End | Strand |
|---|---|---|---|
| RAR | −1299 | −1294 | + |
| TFIID | −1251 | −1246 | + |
| AP2 | −1203 | −1192 | + |
| MYB | −1177 | −1170 | + |
| GR | −1166 | −1153 | + |
| T3R | −1110 | −1095 | − |
| AP1 (C-JUN) | −1052 | −1046 | + |
| CEBP (CEBPA CEBPB) | −1015 | −1008 | + |
| SP1 | −992 | −986 | + |
| HNF (HNF3, HNF5) | −951 | −940 | − |
| MYB | −941 | −934 | + |
| T3R | −933 | −928 | + |
| CP2 | −924 | −918 | − |
| TFIID | −869 | −864 | + |
| HNF (HNF3, HNF5) | −865 | −854 | − |
| GATA1 (NF-E1A) | −844 | −835 | − |
| GATA1 (NF-E1A) | −829 | −820 | +− |
| SP1 | −803 | −794 | + |
| GR | −788 | −775 | + |
| HNF (HNF3, HNF5) | −782 | −750 | + |
| AP1 (C-JUN) | −731 | −725 | +− |
| PEA3 | −731 | −726 | +− |
| PU.1 (NF-JB) | −730 | −725 | − |
| PU.1 (NF-JB) | −696 | −691 | − |
| AP2 | −675 | −665 | − |
| AP2 | −671 | −666 | + |
| H-APF-1 | −658 | −652 | + |
| NE-kappaB | −658 | −647 | + |
| GATA1 (NF-E1A) | −631 | −626 | +− |
| SP1 | −565 | −559 | − |
| CAC-bf (htbeta) | −557 | −547 | + |
| SP1 | −551 | −542 | − |
| TFIID | −537 | −532 | − |

TABLE 1-continued

| Transcription factor | Start | End | Strand |
|---|---|---|---|
| NF-E (NF-E1C) | −509 | −505 | − |
| CCAT-bf (CBF) | −508 | −502 | +− |
| GATA1 (NF-E1A) | −508 | −504 | + |
| CTF/CBP (NF1) | −507 | −502 | + |
| CP2 | −506 | −502 | − |
| NF-Y | −506 | −502 | + |
| CCAAT-bf (CBF) | −464 | −458 | +− |
| CTF/CBP (NF1) | −464 | −459 | − |
| NF-Y | −464 | −460 | − |
| SP1 | −462 | −453 | − |
| SP1 | −459 | −453 | + |
| AP2 | −458 | −447 | + |
| PU.1 (NF-JB) | −445 | −440 | + |
| PEA3 | −444 | −439 | +− |
| SRY | −439 | −428 | + |
| PEA3 | −431 | −426 | +− |
| CEBP (CEBPA CEBPB) | −420 | −412 | − |
| PU.1 (NF-JB) | −400 | −395 | + |
| PEA3 | −399 | −394 | +− |
| AP2 | −305 | −294 | − |
| SP1 | −302 | −287 | + |
| AP2 | −291 | −282 | − |
| CEBP (CEBPA CEBPB) | −272 | −261 | + |
| PEBP2 | −272 | −267 | + |
| MYOD | −257 | −250 | + |
| E2A | −255 | −249 | − |
| SP1 | −244 | −235 | − |
| CAC-bf (htbeta) | −240 | −211 | +− |
| SP1 | −238 | −223 | +− |
| GATA1 (NF-E1A) | −225 | −219 | + |
| SP1 | −225 | −215 | + |
| SP1 | −221 | −209 | − |
| MYB | −211 | −204 | + |
| GR | −197 | −192 | − |
| SP1 | −189 | −183 | +− |
| MYB | −174 | −167 | − |
| SP1 | −166 | −152 | +− |
| MYC/MAX | −151 | −138 | +− |
| USF 1 and 2 (MYOD) (E-box) | −147 | −142 | + |
| AP1 (C-JUN) | −131 | −121 | + |
| SP1 | −100 | −86 | +− |
| CEBP (CEBPA CEBPB) | −90 | −83 | + |
| GR | −80 | −67 | − |
| LXR | −69 | −55 | + |
| TFIID (TBP TATA BOX) | −31 | −26 | + |
| SIF | −3 | 2 | + |
| SP1 | 22 | 31 | + |

FIG. 1 represents a portion of the sequence SEQ ID No. 3. The first nucleotide in the 5' position of the sequence in FIG. 1 is also the first nucleotide in the 5' position of one or the nucleic acid sequences SEQ ID No. 1 and SEQ ID No. 3. In the figure, the binding sites for transcription factors are illustrated with boxes which delimit their respective start and end positions, and their respective designations is indicated above each of the corresponding boxes. The numbering of the nucleotides of the sequence represented in FIG. 1 was carried out with respect to the transcription start site, numbered "+1", the nucleotide 5' to the nucleotide +1 being itself numbered "−1".

The description of the characteristics of the binding sites for each of the transcription factors referred to in FIG. 1 and Table 1 can easily be found by persons skilled in the art. A short description of some of them is produced below.

Factor CAC: The characteristics of a binding site for the factor CAC can be found, for example, in the article by Schuele et al., (1988, Nature, Vol. 332: 87-90), entry No. T00077 of the EMBL database, the article by Mantovani et al., (1988, Nucleic Acids Research Vol. 16: 4299-4313), the article by Catala et al., (1989, Nucleic Acid Research, Vol.

17: 3811-3827) and the article by Wang et al., (1993, Mol. Cell Biol., Vol. 13: 5691-5701). The binding of this factor has been shown on the regulatory regions of several genes, including the promoter for the β-globin gene and the gamma-globin gene. This factor appears to act in cooperation with the glucocorticoid receptor.

Factor C/EBP:

C/EBP-α

The characteristics of a binding site for the factor C/EPB-α can be found, for example, in the articles corresponding to the following entries in the Medline database: 892020040, 94023981, 96194262, 96003748. This factor inhibits cell proliferation by increasing the level of p21 (WAF-1) due to an increased expression of the gene and to a posttranslational stabilization of p21.

C/EBP-β

The binding characteristics for the factor C/EBP β can be found, for example, in the following entries in the Medline database: 93315489, 91248826, 94193722, 93211931, 92390404, 90258863, 94088523, 90269225 and 96133958. It is a transcription activator which is involved in regulating genes involved in immune and inflammatory responses. It binds specifically to an IL-1 response element in the IL-6 gene. It is believed to play a role in regulating the acute phase of inflammation and in hemopoiesis. The consensus recognition site is as follows: "T(T/G) NNGNAA(T/G)".

Factor c-Myb:

The characteristics of a binding site for the factor c-Myb can be found in the following entries in the Medline database: 91122626, 87092302, 93131991, 86261774, 92049347, 90044066, 90265605, 93101590, 94316485 and 90090611. This factor specifically recognizes the sequence "YAAC(G/T)G". It plays a role in controlling the proliferation and differentiation of hematopoietic precursor cells.

Factor CP2:

The characteristics of the binding sites for the factor CP2 can be found, for example, in the articles by Kim et al., (1990), Mol Cell Biol, Vol. 10: 5958-5966 and Lim et al., (1992), J. Biol. Chem. Vol. 268: 18008-18017.

Factor CTF:

The binding characteristics of the factor CTF can be found, for example, in the following entries in the Medline database: 88319941, 91219459, 86140112, 87237877, 90174951, 89282387, 90151633, 892618136, 86274639, 87064414, 89263791. The factor CTF/NF-I recognizes the following palindromic sequence: "TGGCANNNTGCCA" (SEQ ID NO: 21), which is present in viral and cellular promoters and at the origin of replication of type 2 adenoviruses. These proteins are capable of activating transcription and replication. They bind to DNA in the form of a homodimer.

Factor E2A:

The characteristics of a binding site for factor E2A can be found, for example, in the articles corresponding to the following entries in the Medline database: 91160969, 91331308, 91115096, 91117219, 90346284, 89168418, 90150281. This factor binds to a KAPPA-E2 site of the enhancer element of the KAPPA immunoglobulin gene. It forms a heterodimer with the protein ASH1. It belongs to the family of transcription factors of helix-loop-helix type.

Factor GRα:

The characteristics of a binding site for the GRα factor can be found, for example, in the following entries in the Medline database: 88264449, 93024441, 89091080, 90319784, 92020837, 90381775, 86298392, 91131612, 86092211, 86092206. It is a glucocorticoid receptor which is involved in regulating the expression of eukaryotic genes and which affects the proliferation and differentiation of target tissues. This factor binds to the target site of type "GRE". It is composed of three domains and belongs to the NR3 subfamily of hormone nuclear receptors.

Factor LXR:

The characteristics of the binding sites for the factor LXR (Liver X Receptor) have been described by Apfel et al., (Moll. Cell. Biol., 1994), Song et al., (Proc. Natl. Acad. Sci USA, 1994) and Willy et al., (Genes Dev., 1995). Oxysterols are the physiological ligand of LXR elements (Janowski et al., Proc. Natl. Acda. Sci USA, 1999). Like other receptors, LXR heterodimerizes with RXR (Retinoid X Receptor). Our LXR response elements have been identified at positions −1729/−1714 and −69/−55 (FIG. 1).

Factor NF-EIC:

The characteristics of a binding site for the factor NF-EIC can be found, for example, in the following entries in the Medline database: 91266910, 91216113, 91334450, 91203899, 91029498 and 910655813. It is a transcriptional activator which binds to an enhancer element of the α and δ genes of the T cell receptor. It binds to the following consensus sequence: "AGATAG". It belongs to the family of transcription factors of the type GATA.

Factor HNF5:

Persons skilled in the art may, for example, refer to the article by Grange et al. (1991, Nucleic Acids Res. Vol. 19: 131-139) for this transcription factor.

Factor HNF3B:

Persons skilled in the art may advantageously refer to the article by Overdier et al., (1994, Mol. Cell Biol. Vol. 14: 2755-2766).

Factor Nfkappa-B:

Persons skilled in the art may advantageously refer to the articles corresponding to the following entries in the Medline database: 95369245, 91204058, 94280766, 89345587, 93024383, 888248039, 94173892, 91088538, 91239561, 91218850, 92390404, 90156535, 93377072, 92097536, 93309429, 93267517, 92037544, 914266911, 91105848 and 95073993. The factor Nfkappa-B is a heterodimer consisting of a first 50-kDa subunit and a second 65-kDa subunit. Two heterodimers can form a labile tetramer. Its DNA-binding depends on the presence of zinc ($Zn^{++}$). It can be induced by many agents, such as TNF, PKA or PKC. It is generally a regulator of genes involved in responses to infection, inflammation and stress.

Factor NFY:

The factor NFY is described, for example, in entry No. P25.208 of the Swissprot database. It is a factor which recognizes a "CCAAT" moiety in promoter sequences such as those of the gene encoding type 1 collagen, of albumin and of β-actin. It is a transcription stimulator.

Factor PEA3:

Persons skilled in the art may advantageously refer to the articles corresponding to the following entries in the Medline database: 90059931, 90309995, 90291989, 93181246 and 90384794. This transcription factor binds to an "AGGAAG" PEA3 moiety, and can play a regulatory role during embryogenesis.

Factor PEBP2:

Persons skilled in the art may advantageously refer to the articles corresponding to the following entries in the Medline database: 95199266, 94217721, 97188387, 97325753 and 95347606. This factor binds to a "PYGTYGGT" site in many enhancer and promoter elements.

Factor TFIID:

Persons skilled in the art may advantageously refer to the following articles: Fikes et al., (1990, Nature, Vol. 346: 291-294), GILL et al., (1991, Cell, Vol. 65: 333-340), Hoffmann et al., (1990, Genes Dev. Vol. 4: 1141-1148). This factor plays a major role in activating the eukaryotic genes which are transcribed by RNA polymerase II. This factor binds specifically to the TATA promoter element located close to the transcription start site.

Factor T3R:

Persons skilled in the art may advantageously refer to the articles corresponding to the following entries in the Medline database: 92017776, 90242396, 870903752, 91212192. This factor has a strong affinity for triiodothyroine. It is composed of three domains and belongs to the family of hormone nuclear receptors.

Factor SIF:

Persons skilled in the art may advantageously refer to the article by Wagner et al., (1990, EMBO J., Vol. 9: 4477-4784). This factor activates the expression of the c-fos gene.

Factor RAR:

Persons skilled in the art may advantageously refer to the articles corresponding to the following entries in the Medline database: 91216109, 92017791, 92127595, 91219411, 92103690, 93321869, 91092269, 91029504, 90242395, 91029504. This factor is a retinic acid receptor. This factor controls cellular functions by directly regulating gene expression. It belongs to the family of hormone nuclear receptors.

Factor PU:

Persons skilled in the art may advantageously refer to the articles corresponding to the following entries in the Medline database: 92107189, 93165739, 95317607, 92318913, 92275360, 93028372, 93206099, 90199884, 87257848 and 93275657. This factor binds to the PU box, which is a purine-rich DNA sequence, such as the sequence "GAG-GAA", which can act as a lymphoid cell-specific enhancer element.

It is a transcription activation factor which can be specifically involved in the activation or differentiation of macrophages or B cells.

SITE AP1:

The characteristics of a binding site for the transcription factor AP1 can be found in various articles corresponding to the following entries in the Medline database: Numbers 89125693, 89252809, 90318391, 91175677, 911458338, 89313776, 88217909, 911662, 91121514, 89017284, 88070595, 90097934, 88189275, 87301729, 88151062, 90291989, 91330875, 89051877 and 91219459. This factor binds to an enhancer element of the type "TGA(C/G)TCA.

Factor AP2:

The characteristics of a binding site for the transcription factor AP2 can be found, for example, in the articles corresponding to the following entries in the Medline database: 90127451, 90174951 and 91009310.

This factor binds to enhancer-type elements, in order to stimulate the transcription of certain genes. For example, the factor AP2 binds to the following consensus sequence: "CCCCAGGC".

Factor CCAAT:

A characteristic of the binding site for the factor CCAAT can be found in the article by Lum et al., (1990, Mol Cell Biol. Vol. 10: 6709-6717) and in entry No. T 00086 of the EMBL database. This factor has, for example, been shown to be a stimulator of the transcription of the human hsp70 gene promoter.

Factor GATA-1:

The characteristics of the binding site for the factor GATA-1 can be found, for example, in the following entries in the Medline database: 91340773, 91093039, 91266910, 90114418, 89385992, 91268074, 89118131, 91224987, 89218991 and 91081330. It is known to be a "switch" factor in erythroid development. It binds to DNA on the following consensus sequence: "(A/T)GATA(A/G)", in regulatory regions of globin genes and of other genes expressed in erythroid cells.

Factor MyoD-Myf-3:

The characteristics of a binding site for the factor MyoD-Myf-3 can be found, for example, in the article by Rosenthal et al., (1990, Nucleic Acids Res., Vol. 18: 6239). This transcription factor induces differentiation of fibroblasts into myoblasts, activates muscle specific promoters and interacts with, and is inhibited by, the protein twist.

Factor MYC/MAX:

The characteristics of a binding site for the factor Nyc/MAX can be found, for example, in the following entries in the Medline database: 94040733, 93101610, 92229468, 92112037, 93145325, 93026389, 93157390, 92366516, 93145324 and 91173288. This transcription factor binds to DNA nonspecifically, but also binds to DNA specifically by recognizing the sequence CAC[GA]TG. This factor appears to activate the transcription of genes associated with growth.

Factor HNF3:

Persons skilled in the art may advantageously refer to the following entries in the Medline database: 91352065, 91032994, 92345837, 89160814, 91187609, 91160974, 91029477, 94301798 and 94218249. This transcription factor acts as an activator of many genes of the liver, such as AFT, albumin and tyrosine aminotransferase genes, and interacts with regulatory regions which are cis-acting with respect to these genes.

Factor SRY:

Persons skilled in the art may advantageously refer to the articles corresponding to the following entries in the Medline database: 92132550, 95292338, 95112822, 93049201. This factor is responsible, for example, for initiating male sex determination.

Factor Sp1:

Persons skilled in the art may advantageously refer to the articles corresponding to the following entries in the Medline database: 852707437, 89091123, 89039842, 89384647, 85061571, 88111565, 91224491, 91095025, 91357479, 91139695. This factor activates the synthesis of messenger RNA from genes containing functional recognition sites; it can interact with G/C base-rich moieties of the promoter of the serotonin receptor gene.

Factor USF:

USF belongs to the helix-loop-helix family of transcription factors that bind the E-box motif (CACGTG) and include inter alia Myc, Mad1, Max, MyoD (Littlewood et al., Oxford University Press, New York, 1 pp. 1998). Although it has a well-established role as a transcription activator (Ghosh et al., Oncogene, 1997, 14:589-594), it is clear that in some promoter contexts USF does have the capacity to act as a transcription repressor. USF1 has been shown to be important for developmental repression of the LpS1 gene of *Lytechinus pictus* in all cell types except aboral ectoderm cells that do not express USF (Seid et al., *J. Mol Biol*, 1996, 264:7-19). USF1 inhibits autoactivation of the *Xenopus* MyoD gene whose product binds to the E-box (Lun et al., *Cell Growth Differ.*, 1997, 8:275-282) and also represses transcription of the CYP1A1 gene by competing with the stimulatory AhR.Arnt complex for binding to the xenobiotic-responsive element (XRE) that contains an E-box like motif (Takahashi et al., *J Biol Chem,* 1997, 272: 30025-30031). Carter et al. demonstrated that the absence of a strong activation domain in USF1 leads to transcriptional repression of the immunoglobulin heavy-chain (IgH) gene (Carter et al., Mol Cell Biol, 1997, 17:18-23). Truncated and splice variants of USF2 which abrogate E-box activity repress the expression of the major histocompatibility complex class I (Howcroft et al., *Mol Cell Biol* (1999) 19:4788-4797), ATPA (Breen et al., J Biol Chem, 1997, 272:10528-10542) and prostaglandin G/H synthase-2 genes. Harris et al (*J Biol Chem,* 2000, 275:28539-28548) have provided evidence that the close proximity between the AP-1 and E-box elements on the FGF-BP promoter facilitates transcriptional repression via interactions between USF1, USF2 and the AP-1 binding proteins. In addition, overexpression of human USF decreases AP-1 dependent transcription in murine teratocarcinoma F9 cells (Pognonec et al., *Oncogene,* 1997, 14:2091-2098) and USF binding to a complex consisting of AP-1 factors, Fra2 and CREB represses the chicken alphaA-crystallin gene (Cvekl et al., 1994, *Mol Cell Biol,* 147363-7376). USF1 and USF2 homodimers inhibit transcription of the ribosomal RNA gene (Sirito et al, *Gen Expr,* 1992, 2:231-240). USF binding motifs have also been shown to act as negative regulatory elements in the promoters of the Protease Nexin-1 (Erno et al, Mol Cell Neurosci, 1996, 8:28-37) and the HLA-B (Gobin et al., J Immunol, 1999, 163:1428-1434) genes. Interestingly, apolipoprotein CIII, which like ABC1 is involved in lipid metabolism, is also repressed by USF2 (Navantkasattusas et al., Mol Cell biol, 1994, 14: 7331-7339). Finally, USF can both positively and negatively regulate the MLC-2v gene and ribosomal RNA gene transcription. Several studies indicate that USF may also function as a constitutively bound protein that cooperates with basal factors such as $TAF_{II}55$ (Chiang et al., *Science,* 1995, 267:531-536) or inducible factors such as USA (Meisterernst et al., Cell, 1991, 66:981-993), PC5 (Halle et al, J Biol Chem, 1995, 270:21307-21311), c-Myc, Max (Harris et al.), CREB and JunD (Cvekl et al.) to mediate transcriptional induction or repression. Thus, USF can function to either activate or repress gene transcription.

Without wishing to be bound by any theory, the applicant thinks that USF may for example inhibit gene transcription by competing for binding to the E-box with transcriptional activators (Lun et al.; Takahashi et al. above cited). However, the applicant has demonstrated in Example 5 that transfection of EBm (mutated E-box) and EBdel (deleted E-box) constructs in RAW cells led to increased rather than decreased ABC1 promoter activity, consistent with E-box mediated gene repression. Furthermore, gel shift assays using antibodies specific to different E-box binding activators failed to demonstrate binding to the E-box motif. Western blot analysis were also performed to determine truncated and splice variants of USF2 that lack the transactivation domain (Liu et al., Sirito et al., et Howcroft et al.,) and lead to gene repression. Under these conditions, these USF variants were not detected in RAW cell or 293 cell nuclear extracts.

Because USF can also function as a repressor through specific protein-protein interaction with transcriptional activators that bind DNA motifs distinct from the E-box (Harris et al., Pognonec et al., Cvekl et al., above-cited). As previously described, in the human ABC1 promoter, the E-box motif is flanked by two Sp1 sites and an AP1 motif. It is well known in the art that transcription factors which bind to Sp1 and AP1 have been implicated in the transcriptional regulation of other genes involved in lipid metabolism including apoA-II (Ribeiro et al., J Biol Chem, 265:1216-1225), apoC-III (Ogami et al, J. Biol Chem, 1990, 265:9808-9815), chicken vitellogenin II (Seal et al., Mol Cell Biol, 1991, 11:2704-2717), fatty acid synthase (Casado et al., J Biol Chem, 1999, 274:2009-2013) and the LDL receptor (Sanchez et al., J Biol Chem, 1995, 270:1161-1169) and the LDL receptor related protein (LRP) (Gaeta et al., BBA, 1994,1219:307-313.)

An preferred characteristic of the regulatory nucleic acid according to the invention, and characteristic of the sequence located upstream of the transcription start site, included in both the sequence SEQ ID No. 1 and in the sequence SEQ ID No. 3, is the presence of eight moieties which are characteristic of a putative binding site for the proteins PPAR. The PPARs, also referred to as peroxisome proliferator-activated receptors, which can be of type $\alpha, \delta(\beta)$ and $\gamma$, form a subfamily belonging to the family of nuclear receptor genes. All PPARs are activated by fatty acids and derivatives thereof. For example, the PPAR of type $\alpha$ binds to hypolipidemic fibrates, whereas antidiabetic glitazones are ligands for the PPAR of type gamma. Activation of the PPAR of type $\alpha$ induces pleiotropic effects such as the stimulation of lipid oxidation, the impairment of lipoprotein metabolism and the inhibition of vascular inflammation. Activators of PPAR$\alpha$ increase hepatic absorption and esterification of free fatty acids by stimulating the expression of the fatty acid transport protein and of the acyl-CoA synthetase. In the skeletal muscle and the heart, PPAR$\alpha$ increases mitochondrial absorption of free fatty acids, and their oxidation, by stimulating muscle-specific carnitine palmitoyl transferase I. The effect of fibrates on the metabolism of triglyceride-rich lipoproteins is due to the stimulation of lipoprotein lipase, this stimulation being dependent on PPAR$\alpha$, and to the inhibition of apolipoprotein C-III, whereas the increase in plasmatic cholesterol, in the form of HDL, depends on an overexpression of apolipoprotein A-I and apolipoprotein A-II.

PPAR$\alpha$s are also expressed in atherosclerotic adhesions. PPAR$\alpha$ inhibits inducible nitric oxide synthase in macrophages and prevents IL-1-induced cyclooxygenase-2 and IL-6 expression, as well as thrombin-induced endothelin-1 expression, which results from a negative transcriptional regulation of the nuclear factor of the signaling pathways of the nuclear factor NF-KAPPA B and of activating protein-1.

The activation of PPAR$\alpha$ also induces apoptosis in monocyte-derived macrophages, probably by inhibiting the activity of NFKAPPA B. Thus, the pleiotropic effects of the PPAR$\alpha$ activators on the plasmatic lipid profile certainly participate in inhibiting the development of atherosclerosis. PPAR$\alpha$ activators, such as fibrates, inhibit the development of atherosclerosis because of their normolipidemic activities.

The presence of eight potential PPAR binding sites (positions of the start and end nucleotides, with respect to the transcription start site, for each of the sites: −1280-1276/−1270-1264, −889-883/−878-872, −584-578/−575-569 and −366-360/−358-352 [also FIG. 1]) on a regulatory nucleic acid according to the invention is compatible with the observation according to which the expression of the gene encoding the human ABC1 protein is induced during the differentiation of monocytes into macrophages in vitro. It is also compatible with the prior observation of the regulation of the ABC1 gene by fibrates. It is also compatible with experimental results demonstrating that the expression of the ABC1 gene is increased when human macrophages are incubated in the presence of acetylated low density lipoproteins (AcLDLs).

Without wishing to be bound by any theory, the applicant thinks that the PPAR binding sites identified according to the invention on the regulatory nucleic acid of sequence SEQ ID No. 1 are highly involved in the tissue specific regulation, and in the specific regulation of the cellular metabolic situation, of the ABC1 gene, and that as a result, a regulatory sequence which comprises at least 4, for example, at least 5, 6, 7 or all of the 8 PPAR binding sites (FIG. 1)(of the sequence SEQ ID No. 1, and which also comprises a basic promoter element, is useful as a regulatory sequence for a polynucleotide whose expression is desired in the liver, the lungs, the adrenal glands, the monocytes/macrophages, the placenta or the fetal tissues, or for a polynucleotide whose expression is desired in response to a specific stimulation of the cell, in relation with cholesterol metabolism, such as the presence, in the cellular environment, of acetylated low density lipoproteins (Ac LDLs).

In addition, it has been shown according to the invention that a regulatory nucleic acid for the human ABC1 gene, as defined above, which comprises all the abovementioned PPAR sites, is capable of regulating the expression of a coding sequence placed under its control, in a manner which is dependent on the presence of cholesterol in the cellular environment. The results are presented in Example 4 below.

As previously mentioned, the invention concerns a nucleic acid comprising a polynucleotide which has at least 20 consecutive nucleotides of either of the nucleotide sequences SEQ ID No. 1 and SEQ ID No. 2, as well as a nucleic acid of complementary sequence.

The nucleic acids comprising one or more "biologically active" fragments of either of the sequences SEQ ID No. 1 and SEQ ID No. 2 are encompassed in the definition above. Persons skilled in the art can easily obtain biologically active fragments of these sequences by referring, for example, to Table 1 below and to FIG. 1, in which are presented the various moieties which are characteristic of the regulatory sequence for the ABC1 gene. Persons skilled in the art may thus obtain such biologically active fragments by totally or partially chemically synthesizing the corresponding polynucleotides or by using restriction endonucleases to obtain desired DNA fragments, the restriction sites present on the sequences SEQ ID No. 1 and SEQ ID No. 1 being able to be easily found from the sequence information, with the aid of current restriction mapping software such as GCG version 9.1 module map.

The production of nucleic acid fragments determined using restriction endonucleases is described, for example, in the work by Sambrook et al. (1989).

The invention thus also relates to a nucleic acid as defined above, which is capable of modulating the transcription of a polynucleotide placed under its control.

According to one embodiment, a biologically active fragment of a transcription-regulating acid according to the invention comprises the basic promoter (TATA box and homeobox) ranging from the nucleotide at position −1 to the nucleotide at position −300, with respect to the transcription start site, the first nucleotide transcribed being the nucleotide in position 2894 of the nucleotide sequence SEQ ID No. 1.

According to a second embodiment, a biologically active fragment of a transcription-regulating nucleic acid according to the invention comprises both the basic promoter and the proximal regulatory elements, ranging from the nucleotide at position −1 to the nucleotide at position −600, with respect to the transcription start site, the first nucleotide transcribed being the nucleotide in position 2894 of the nucleotide sequence SEQ ID No. 1.

According to a third embodiment, a biologically active fragment of a transcription-regulating nucleic acid according to the invention comprises besides the basic promoter (core promoter) and the proximal 200 bp of the ABC1 gene promoter which is rich in binding sites for transcription factors, i.e., Sp1, AP1, LXR, and E-box, that are likely involved in modulating human ABC1 gene expression.

According to a fourth embodiment, such a biologically active fragment of a transcription-regulating acid according to the invention also comprises, besides the basic promoter (core promoter) and the proximal regulatory elements, other regulatory elements such as the various PPARα sites, and stretches from the nucleotide at position −1 to the nucleotide at position −2894, with respect to the transcription start site, the first nucleotide transcribed being the nucleotide in position 2894 of the nucleotide sequence SEQ ID No. 1.

According to a fifth embodiment, such a biologically active fragment of a transcription-regulating acid according to the invention, which also comprises, besides the basic promoter (core promoter) and the proximal regulatory elements, other regulatory elements such as the various PPARα sites, stretches from the nucleotide at position +120 to the nucleotide at position −995, with respect to the transcription start site, the first nucleotide transcribed being the nucleotide in position 2894 of the nucleotide sequence SEQ ID No. 1.

According to a sixth embodiment, a biologically active fragment of a transcription-regulating nucleic acid according to the invention comprises a region ranging from the nucleotide at position +108 to the nucleotide at position −2228, with respect to the transcription start site as set forth in sequence SEQ ID No. 1.

Exons 1A and 1B and Introns 1A and 1B

The applicant has also identified the nucleotide sequences located downstream of the transcription start site, and corresponding respectively, from the 5' end to the 3' end, to exon 1A, intron 1A, exon 1B and intron 1B of the human gene encoding the ABC1 protein.

More precisely, exon 1A, which is 221 nucleotides long, starts at the nucleotide at position 2894 of the sequence SEQ ID No. 1 and ends at the nucleotide at position 3114 of the sequence SEQ ID No. 1. Exon 1A is identified as the sequence SEQ ID No. 4.

Exon 1B, which is 109 nucleotides long, starts at the nucleotide at position 100 and ends at the nucleotide at position 258 of the sequence SEQ ID No. 2. Exon 1B is identified as the sequence SEQ ID No. 5.

Intron 1A has been partially sequenced. The 5' end of intron 1A starts at the nucleotide at position 3115 and ends at the nucleotide at position 3231 of the nucleotide sequence SEQ ID No. 1, and is also defined as the sequence SEQ ID No. 6. The 3' end of intron 1A starts at the nucleotide at position 1 and ends at the nucleotide at position 99 of the nucleotide sequence SEQ ID No. 2, and is also identified as the sequence SEQ ID No. 7.

Intron 1B has been partially sequenced. The 5' end of intron 1B starts at the nucleotide at position 259 and ends at the nucleotide at position 357 of the sequence SEQ ID No. 2. This sequence is also identified as the sequence SEQ ID No. 8.

Exon 1B contains the start of the open reading frame of the human ABC1 gene, the nucleotide A of the ATG codon being located in start position at position 94 of the sequence SEQ ID No. 5. Exon 1B encodes the polypeptide of sequence SEQ ID No. 9.

Exons 1A and 1B, as well as introns 1A and 1B, can contain elements for regulating the expression of the ABC1 gene, for example, elements of enhancer type and/or elements of silencer type.

Consequently, a transcription-regulating nucleic acid according to the invention can also contain, besides biologically active fragments of the sequence SEQ ID No. 1, nucleotide fragments, or even all, of the sequences SEQ ID No. 2 to SEQ ID No. 8.

The nucleotide sequences SEQ ID No. 1 to SEQ ID No. 8, as well as fragments thereof, can, for example, be used as nucleotide probes or primers for detecting the presence of at least one copy of the ABC1 gene in a sample, or for amplifying a given target sequence in the regulatory sequence for the ABC1 gene.

An individual of the invention is thus a nucleic acid having at least 80% nucleotide identity with a nucleic acid as defined above, for example, originating from one of the sequences SEQ ID No. 1 to SEQ ID No. 8.

The invention also concerns a nucleic acid which hybridizes, under high stringency conditions, with any one of the nucleic acids according to the invention, for example, a nucleic acid originating from a sequence chosen from the sequences SEQ ID No. 1 to SEQ ID No. 8.

The invention also relates to a nucleic acid as defined above and also further characterized in that it is capable of modifying the transcription of a polynucleotide of interest placed under its control.

According to a first aspect, such a nucleic acid is capable of activating the transcription of the polynucleotide of interest placed under its control.

According to a second aspect, a regulatory nucleic acid according to the invention can be characterized in that it is capable of inhibiting the transcription of the polynucleotide of interest placed under its control.

For example, a transcription-regulating nucleic acid according to the invention, when it is suitably located with respect to a polynucleotide of interest whose expression is desired, will allow the transcription of said polynucleotide of interest, either constitutively or inducibly.

The inducible nature of the transcription initiated by a regulatory nucleic acid according to the invention can be conferred by one or more of the regulatory elements that it contains, for example, the presence of one or more PPARα sites, such as at least 4 PPARα sites, or at least 5, 6, 7 PPARα sites or the 8 PPARα sites of the sequence SEQ ID No. 1 or SEQ ID No. 3.

In addition, a tissue specific expression of the polynucleotide of interest can be sought by placing this polynucleotide of interest under the control of a regulatory nucleic acid according to the invention which is capable, for example, of initiating the transcription of this polynucleotide of interest specifically in certain categories of cells, for example, cells from the liver, placenta cells or macrophages.

In general, a regulatory nucleic acid according to the invention can comprise one or more "discrete" regulatory elements, such as enhancer and silencer elements. For example, such a regulatory nucleic acid can comprise one or more potential transcription factor binding sites as defined in FIG. 1.

A regulatory acid according to the invention also encompasses a sequence which does not comprise the basic promoter, i.e. the sequence ranging from the nucleotide at position −1 to the nucleotide at position −300, with respect to the transcription start site.

Such a regulatory nucleic acid will then generally comprise a so-called "heterologous" basic promoter, i.e. a polynucleotide comprising a "TATA" box and a "homeobox", which does not originate from the regulatory nucleic acid for the ABC1 gene.

A transcription-regulating nucleic acid comprising all or part of the sequence SEQ ID No. 1 which has been modified, for example, by addition, deletion or substitution of one or more nucleotides, also forms part of the invention. Such modifications can modify the transcriptional activity by causing an increase, or on the contrary a decrease, in the activity of the promoter or of the regulatory element.

Such a modification can also affect the tissue specificity of the promoter or of the regulatory element. Thus, for example, a regulatory nucleic acid according to the invention can be modified in order to stimulate transcription in only one of the tissues in which it is naturally expressed.

A transcription-regulating acid according to the invention can also be modified and be made inducible by a specific compound, for example, by creating, in the sequence, a site which is inducible by a given therapeutic compound.

The modifications in a sequence which comprises all or part of the sequence SEQ ID No. 1 and which comprises the promoter or a regulatory element can be carried out using methods that are well known to persons skilled in the art, such as mutagenesis. The activity of the modified promoter or regulatory element can then be tested, for example, by cloning the modified promoter upstream of a reporter gene, by transfecting the resulting DNA construct into a host cell and by measuring the level of expression of the reporter gene in the transfected host cell. The activity of the modified promoter can also be analyzed in vivo in transgenic animals. It is also possible to construct libraries of modified fragments, which can be screened using functional tests in which, for example, only the promoters or the regulatory elements having the desired activity will be selected.

Such assays can be based, for example, on the use of reporter genes which confer resistance to given compounds, for example, to antibiotics. The selection of cells which have a regulatory nucleic acid/reporter gene construct, and which contain a promoter or a regulatory element with the desired modification, can then be isolated by culturing the transformed host cells having such a construct, in the presence of the given compound, for example, of the given antibiotic.

The reporter gene can also encode any easily detectable protein, for example, an optically detectable protein such as luciferase.

Consequently, an individual of the invention is also a nucleic acid comprising:

a) a transcription-regulating nucleic acid as defined above; and b) a polynucleotide of interest encoding a polypeptide or a nucleic acid of interest.

According to a first aspect, the polynucleotide of interest whose transcription is desired encodes a protein or a peptide. The protein can be of any nature, for example, a protein of therapeutic interest, including cytokines, structural proteins, receptors or transcription factors. For example, when transcription specifically in certain tissues is desired, such as for example, in liver, macrophage or placenta cells, the transcription-regulating nucleic acid will advantageously comprise a nucleic acid ranging from the nucleotide at position −1 to the nucleotide at position −1318, with respect to the transcription start site of the sequence SEQ ID No. 1 or SEQ ID No. 3.

In this case, the polynucleotide of interest will encode a gene involved in combating inflammation, such as a cytokine receptor, or a superoxide dismutase. If an antitumoral effect is desired, then stimulation of the number and the activation of cytotoxic T lymphocytes specific for a given tumoral antigen will be sought.

Alternatively, the regulatory nucleic acid advantageously comprises a nucleic acid ranging from the nucleotide at position +108 to the nucleotide −2228, with respect to the transcription start site of the sequence SEQ ID NO: 1.

In another embodiment, a regulatory nucleic acid according to the invention will be used in combination with a polynucleotide of interest encoding the ABC1 protein.

As already mentioned, the polynucleotide of interest can also encode a nucleic acid, such as an antisense nucleic acid specific for a gene the inhibition of whose translation is desired.

According to another aspect, the polynucleotide of interest, whose transcription is regulated by the regulatory nucleic acid, is a reporter gene, such as any gene encoding a detectable protein.

Among the exemplified reporter genes, mention may be made for example, of the luciferase, the β-galactosidase (LacZ) or the chloramphenicol acetyl transferase (CAT) gene, or any gene encoding a protein which confers resistance to a specific compound, such as to an antibiotic.

Recombinant Vectors

For the purposes of the present invention, "vector" will be intended to mean a linear or circular RNA or DNA molecule which is indifferently in the single-stranded or double-stranded form.

According to a first embodiment, a recombinant vector according to the invention is used to amplify the regulatory nucleic acid according to the invention, which is inserted therein after transformation or transfection of the desired host cell.

According to a second embodiment, they are expression vectors comprising, besides a regulatory nucleic acid in accordance with the invention, sequences whose expression is sought in a host cell or in a given multicellular organism.

According to an advantageous embodiment, a recombinant vector according to the invention will, for example, comprise the following elements:

(1) a regulatory nucleic acid according to the invention;

(2) a polynucleotide of interest comprising a coding sequence included in the nucleic acid to be inserted into such a vector, said coding sequence being placed in frame with the regulatory signals described in (1); and (3) suitable transcription start and stop sequences.

In addition, the recombinant vectors according to the invention may include one or more origins of replication in the host cells in which their amplification or their expression is desired, markers or selection markers.

By way of examples, the bacterial promoters may be the promoters LacI or LacZ, the T3 or T7 bacteriophage RNA polymerase promoters, or the lambda phage PR or PL promoters.

The promoters for eukaryotic cells may comprise the thymidine kinase promoter of the virus HSV or the mouse metallothionine-L promoter.

In general, for the choice of a suitable promoter, persons skilled in the art may advantageously refer to the above-mentioned work by Sambrook et al. (1989) or to the techniques described by Fuller et al. (1996).

When the expression of the genomic sequence of the ABC1 gene is desired, vectors which are capable of including large insertion sequences will, for example, be used. In this specific embodiment, bacteriophage vectors, such as the P1 bacteriophage vectors like the vector p158 or the vector p158/neo8 described by Sternberg (1992, 1994), will, for example, be used.

Bacterial vectors according to the invention can be, for example, the vectors pBR322(ATCC37017) or vectors such as pAA2233 (Pharmacia, Uppsala, Sweden) and pGEMI (Promega Biotech, Madison, Wis., USA,).

Mention may also be made of other commercialized vectors, such as the vectors pQE70, pQE60, pQE9 (Qiagen), psiX174, pBluescript SA, pNH8A, pNH16A, pNH18A, pNH46A, pWLNEO, pSV2CAT, pOG44, pXTI, pSG(Stratagene).

It can also be the recombinant vector PXP1 described by Nordeen SK et al. (1988, Bio Techniques, 6: 454-457).

They can also be vectors of Baculovirus type, such as the vector pVL1392/1393 (Pharmingen) used for transfecting cells of the Sf9 line (ATCC No. CRL 1711) derived from *Spodoptera frugiperda*.

They can also be adenoviral vectors, such as the type 2 or 5 human adenovirus.

A recombinant vector according to the invention can also be a retroviral vector or an adeno-associated vector (AAV). Such adeno-associated vectors are described, for example, by Flotte et al. (1992), Samulski et al. (1989) or McLaughlin B A et al. (1996).

To enable the expression of a polynucleotide of interest under the control of a regulatory nucleic acid according to the invention, the polynucleotide construct comprising the regulatory sequence and the coding sequence may be introduced into a host cell. The introduction of such a polynucleotide construct according to the invention into a host cell can be carried out in vitro, according to the techniques well known to persons skilled in the art for transforming or transfecting cells, either in primary culture or in the form of cell lines. The introduction of the polynucleotides according to the invention can also be carried out in vivo or ex vivo, for preventing or treating diseases linked to a deficiency in the reverse transport of cholesterol.

To introduce the polynucleotides or the vectors into a host cell, persons skilled in the art may advantageously refer to various techniques, such as the calcium phosphate precipitation technique (Graham et al., 1973, Chen et al., 1987), DEAE Dextran (Gopal, 1985), electroporation (Tur-Kaspa, 1896; Potter et al., 1984), direct microinjection (Harland et al., 1985) or DNA-loaded liposomes (Nicolau et al., 1982, Fraley et al., 1979).

Once the polynucleotide has been introduced into the host cell, it can be stably integrated into the genome of the cell. The integration can be carried out at a specific place in the genome, by homologous recombination, or it can be randomly integrated. In some embodiments, the polynucleotide can be stably maintained in the host cell in the form of an episome fragment, the episome comprising sequences which allow the latter to be maintained and replicated, either independently or in synchrony with the cell cycle.

According to one embodiment, one method for introducing a polynucleotide according to the invention into a host cell, such as a host cell originating from a mammal, in vivo, comprises a preparation comprising a pharmaceutically compatible vector and a "naked" polynucleotide according to the invention, placed under the control of suitable regulatory sequences, are introduced by local injection into the chosen tissue for example, a smooth muscle tissue, the "naked" polynucleotide being absorbed by the cells of this tissue.

Compositions for use in vitro and in vivo comprising "naked" polynucleotides are described for example, in PCT Application No. WO 95/11307 (Pasteur Institute, Inserm, University of Ottawa) and in the articles by Tacson et al. (1996) and by Huygen et al. (1996).

According to one specific embodiment of the invention, a composition is provided for producing a protein of interest in vivo. This composition comprises a polynucleotide encoding the polypeptide of interest, placed under the control of a regulatory sequence according to the invention, in solution in a physiologically acceptable vector.

The amount of vector which is injected into the chosen host organism varies according to the site of injection. By way of indication, between approximately 0.1 and approximately 100 µg of the regulatory sequence/coding sequence polynucleotide construct can be injected into the body of an animal.

When the regulatory nucleic acid according to the invention is located, on the polynucleotide construct (or vector), so as to control the transcription of a sequence comprising an open reading frame encoding the ABC1 protein, the vector may be injected into the body of a patient likely to develop a disease linked to a deficiency in the reverse transport of cholesterol, or who has already developed this disease, for example, a patient with a predisposition for Tangier disease, or who has already developed the disease.

Consequently, the invention also concerns a pharmaceutical composition intended for preventing, or for treating individuals affected by, a dysfunction of the reverse transport of cholesterol, comprising a regulatory nucleic acid according to the invention and a polynucleotide of interest encoding the ABC1 protein, in combination with one or more physiologically compatible excipients.

Advantageously, such a composition will comprise the regulatory nucleic acid defined by either of the sequences SEQ ID No. 1 and SEQ ID No. 2, or a biologically active fragment of this regulatory nucleic acid.

A subject of the invention is also a pharmaceutical composition intended for preventing, or for treating individuals affected by, a dysfunction of the reverse transport of cholesterol, comprising a recombinant vector as defined above in association with one or more physiologically compatible excipients.

The invention also relates to the use of a polynucleotide construct in accordance with the invention which comprises a regulatory nucleic acid for the ABC1 gene, as well as a sequence encoding the ABC1 protein, for manufacturing a medicinal product intended for preventing atherosclerosis in various forms or, for example, for treating individuals affected by a dysfunction of the reverse transport of cholesterol.

The invention also relates to the use of a recombinant vector according to the invention, comprising, besides a regulatory nucleic acid of the invention, a nucleic acid encoding the ABC1 protein, for manufacturing a medicinal product intended for preventing atherosclerosis in various forms or, for example, for treating individuals affected by a dysfunction of the reverse transport of cholesterol.

Vectors which are Useful in Somatic Gene Therapy Methods and Compositions Containing such Vectors The present invention also concerns a novel therapeutic approach for treating pathologies linked to cholesterol transport. It proposes an advantageous solution to the drawbacks of the prior art, by demonstrating the possibility of treating pathologies, for example, pathologies linked to cholesterol transport, by gene therapy, by transferring and expressing, in vivo, a polynucleotide construct comprising, besides a regulatory nucleic acid according to the invention, a sequence encoding an ABC1 protein involved in cholesterol transport and metabolism. The invention also offers a simple means which allows specific and effective treatment of the associated pathologies such as for example, atherosclerosis.

Gene therapy consists in correcting a deficiency or an abnormality (mutation, aberrant expression, etc.) or in effecting the expression of a therapeutic protein of interest by introducing genetic information into the affected cell or organ. This genetic information can be introduced either ex vivo, into a cell extracted from the organ, the modified cell then being reintroduced into the body, or directly in vivo into the appropriate tissue. In this second case, various techniques exist, among which diverse techniques of transfection involving complexes of DNA and of DEAE-dextran (Pagano et al., J. Virol. 1 (1967) 891), of DNA and of nuclear proteins (Kaneda et al., Science 243 (1989) 375), and of DNA and of lipids (Felgner et al., PNAS 84 (1987) 7413), the use of liposomes (Fraley et al., J. Biol. Chem. 255 (1980) 10431), etc. More recently, the use of viruses as vectors for transferring genes has appeared as a promising alternative to these physical techniques of transfection. In this respect, various viruses have been tested for their capacity to infect certain cell populations. For example, retroviruses (RSV, HMS, MMS, etc.), the HSV virus, adeno-associated viruses and adenoviruses.

The present invention thus also relates to a novel therapeutic approach for treating pathologies linked to cholesterol transport, consisting in transferring and in expressing, in vivo, genes encoding ABC1 placed under the control of a regulatory acid according to the invention. The applicant has now advantageously shown that it is possible to construct recombinant viruses which contain a DNA sequence comprising a regulatory nucleic acid according to the invention and a sequence encoding an ABC1 protein involved in cholesterol metabolism, and to administer these recombinant viruses in vivo, and that this administration enables an expression of a biologically active ABC1 protein in vivo, which is stable and effective, and which is without cytopathological effect.

Adenoviruses constitute vectors which are efficient for transferring and expressing the ABC1 gene. For example, the use of recombinant adenoviruses as vectors makes it possible to obtain levels of expression of the gene of interest which are sufficiently high to produce the desired therapeutic effect. Other viral vectors, such as retroviruses or adeno-associated viruses (AAVs), which enable a stable expression of the gene, are also claimed.

The present invention thus offers a novel approach for treating and preventing cardiovascular and neurological pathologies linked to the abnormalities in cholesterol transport.

A subject of the invention is thus a defective recombinant virus comprising a regulatory nucleic acid according to the invention and a nucleic acid sequence encoding an ABC1 protein involved in cholesterol metabolism.

The invention also relates to the use of such a defective recombinant virus for preparing a pharmaceutical composition intended for treating and/or for preventing cardiovascular diseases.

The present invention also concerns the use of cells which are genetically modified ex vivo with a virus as described above, or of producer cells for such viruses, which are implanted in the body, enabling a protracted and effective in vivo expression of a biologically active ABC1 protein.

The present invention shows that it is possible to incorporate a DNA sequence encoding ABC1, under the control of a regulatory nucleic acid as defined above, into a viral vector, and that these vectors make it possible to effectively express a biologically active mature form. For example, the invention shows that the in vivo expression of ABC1 can be obtained by direct administration of an adenovirus or by implantation of a producer cell or a cell which is genetically modified with an adenovirus or with a retrovirus incorporating such a DNA.

The present invention is also advantageous because it makes it possible to induce an expression of ABC1 which is controlled and without harmful effects, in organs which the expression of this protein does not normally concern. For example, a significant release of the ABC1 protein is obtained by implantation of cells which produce vectors of the invention, or which are infected ex vivo with vectors of the invention.

The cholesterol transporter activity produced in the context of the present invention can be of human or animal ABC1 type. The nucleic acid sequence used in the context of the present invention can be a cDNA, a genomic DNA (gDNA) an RNA (in the case of retroviruses) or a hybrid construct consisting for example, of a cDNA into which one or more introns would be inserted. It can also be synthetic or semisynthetic sequences. For example, a cDNA or a gDNA is used. For example, the use of a gDNA allows better expression in human cells. To allow their incorporation in a viral vector according to the invention, these sequences are advantageously modified, for example, by site-directed mutagenesis, for example, for inserting suitable restriction sites. The sequences described in the prior art are not in fact constructed for a use according to the invention, and prior adjustments may prove to be necessary, so as to obtain substantial expressions. In the context of the present invention, use of a nucleic acid sequence encoding a human ABC1 protein is one example. Moreover, it is also possible to use a construct encoding a derivative of these ABC1 proteins. A derivative of these ABC1 proteins comprises, for example, any sequence which is obtained by mutation, deletion and/or addition, with respect to the native sequence, and which encodes a product which conserves cholesterol transporter activity. These modifications can be carried out by the techniques known to persons skilled in the art (see the general molecular biology techniques below). The biological activity of the derivatives thus obtained can then be easily determined, as indicated, for example, in the examples describing the measurement of the afflux of cholesterol from cells. For the purposes of the invention, the derivatives can also be obtained by hybridization using nucleic acid libraries, using the native sequence or a fragment of this sequence as probe.

These derivatives are, for example, molecules with greater affinity for their binding sites, molecules having greater resistance to protease, or molecules with a greater therapeutic efficacy or fewer side effects, or optionally, novel biological properties. The derivatives also include the modified DNA sequences which allow improved expression in vivo.

In a first embodiment, the present invention concerns a defective recombinant virus comprising a regulatory nucleic acid according to the invention and a cDNA sequence encoding an ABC1 protein involved in cholesterol transport and metabolism. In another embodiment of the invention, the DNA sequence is a gDNA sequence. The cDNA sequence which encodes the ABC1 protein, and which can be used in a vector according to the invention, is advantageously the sequence SEQ ID No. 10.

The vectors of the invention can be prepared from various types of virus. For example, vectors derived from adenoviruses, adeno-associated viruses (AAV), herpesviruses (HSV) or retroviruses are used. It is also advantageous to use an adenovirus for a direct administration or for modifying, ex vivo, cells intended for implanting, or a retrovirus for implanting producer cells.

The viruses according to the invention are defective, i.e. they are incapable of replicating autonomously in the target cell. Generally, the genome of the defective viruses used in the context of the present invention is thus lacking at least the sequences required for replication of said virus in the infected cell. These regions can be either removed (totally or partially), or rendered nonfunctional or substituted with other sequences, and, for example, with the nucleic acid sequence encoding the ABC1 protein. For example, however, the defective virus conserves the sequences in its genome which are required for encapsidation of viral particles.

In regards to adenoviruses, various serotypes, whose structure and properties vary somewhat, have been characterized. For example, among these serotypes, in the context of the present invention, type 2 or 5 human adenoviruses (Ad 2 or Ad 5) or adenoviruses of animal origin (see application WO 94/26914) may be used. Among the adenoviruses of animal origin which can be used in the context of the present invention, mention may be made of the adenoviruses of canine, bovine, murine (example: Mav1, Beard et al., Virology 75 (1990) 81), ovine, porcine, avian or simian (example: SAV) origin. For example, the adenovirus of animal origin may be a canine adenovirus, such as a CAV2 adenovirus [Manhattan or A26/61 strain (ATCC VR-800) for example]. For example, in the context of the invention, adenoviruses of human or canine or mixed origin may be used. In addition, the defective adenoviruses of the invention may also comprise ITRs, a sequence enabling the encapsidation and the sequence encoding the ABC1 protein placed under the control of a nucleic acid according to the invention. In one embodiment of the present invention, in the genome of the adenoviruses of the invention, the E1 region at least is rendered nonfunctional. In another embodiment, in the genome of the adenoviruses of the invention, the E1 gene and at least one of the genes E2, E4 and L1-L5 are nonfunctional. The viral gene under consideration can be rendered nonfunctional by any technique known to persons skilled in the art, and, for example, by total elimination, substitution, partial deletion, or addition of one or more bases in the gene(s) under consideration. Such modifications can be obtained in vitro (on isolated DNA) or in situ, for example, by means of the techniques of genetic engineering or by treatment with mutagenic agents. Other regions can also be modified, and, for example, the E3 region (WO 95/02697), E2 (WO 94/28938), E4 (WO 94/28152, WO 94/12649, WO 95/02697) and L5 (WO 95/02697). According to one embodiment, the adenovirus according to the invention comprises a deletion in the E1 and E4 regions, and the sequence encoding ABC1 is inserted into the inactivated E1 region. According to another embodiment, it comprises a deletion in the E1 region, into which are inserted the E4 region and the sequence encoding ABC1 (French Patent Application FR 94 13355).

The defective recombinant adenoviruses according to the invention can be prepared by any technique known to persons skilled in the art (Levrero et al., Gene 101 (1991) 195, EP 185 573; Graham, EMBO J. 3 (1984) 2917). For example, they can be prepared by homologous recombination between an adenovirus and a plasmid carrying, inter alia, the DNA sequence encoding the ABC1 protein. The homologous recombination takes place, for example, after cotransfection of said adenovirus and plasmid into a suitable cell line. The cell line used should, for example, (i) be transformable by said elements, and (ii) have the sequences which are capable of complementing the portion of the genome of the defective adenovirus, such as in an integrated form to avoid the risks of recombination. By way of example of a line, mention may be made of the 293 human embryonic kidney line (Graham et al., J. Gen. Virol. 36 (1977) 59), which comprises, for example, integrated into its genome, the left-hand portion of the genome of an adenovirus Ad5 (12%) or lines which are capable of complementing the E1 and E4 functions, as described, for example, in applications No. WO 94/26914 and WO 95/02697.

Next, the adenoviruses which have multiplied may be recovered and purified according to the conventional techniques of molecular biology, as illustrated in the examples.

As regards the adeno-associated viruses (AAVs), they are relatively small DNA viruses, which integrate into the genome of the cells that they infect, in a stable and site-specific way. They are capable of infecting a broad spectrum of cells, without inducing effects on cell growth, morphology or differentiation. Moreover, they do not seem to be involved in pathologies in humans. The AAV genome has been cloned, sequenced and characterized. It comprises approximately 4700 bases and contains, at each end, an inverted repeat region (ITR) of 145 bases approximately which serves as an origin of replication for the virus. The rest of the genome is divided into two essential regions carrying the encapsidation functions: the left-hand portion of the genome, which contains the rep gene which is involved in viral replication and expression of viral genes; the right-hand portion of the genome, which contains the cap gene which encodes the capsid proteins of the virus.

The use of AAV-derived vectors for transferring genes in vitro and in vivo has been described in the literature (see, for example, WO 91/18088; WO 93/09239; U.S. Pat. Nos. 4,797,368, 5,139,941, EP 488 528). These documents describe various AAV-derived constructs, in which the rep and/or cap genes are deleted and replaced with a gene of interest, and their use for transferring said gene of interest in vitro (on culture cells) or in vivo (directly in an organism). However, none of these documents describes or suggests using a recombinant AAV for transferring and expressing an ABC1 protein in vivo or ex vivo, or the advantages of such a transfer. The defective recombinant AAVs according to the invention can be prepared by cotransfecting, into a cell line which has been infected with a human helper virus (for example, an adenovirus), a plasmid containing the sequence encoding the ABC1 protein, bordered by two AAV inverted repeat regions (ITR), and a plasmid carrying the AAV encapsidation genes (rep and cap genes). The recombinant AAVs produced may then be purified by conventional techniques.

As regards herpes viruses and retroviruses, the construction of recombinant vectors has been widely described in the literature: see, for example, Breakfield et al., New Biologist 3 (1991) 203; EP 453242, EP 178220, Bernstein et al. Genet. Eng. 7 (1985) 235; McCormick, Bio Technology 3 (1985) 689, etc.

For example, retroviruses are integrating viruses which infect dividing cells. The retrovirus genome comprises two LTRs, an encapsidation sequence and three coding regions (gag, pol and env). In retrovirus-derived recombinant vectors, the gag, pol and env genes are generally totally or partially deleted and replaced with a heterologous nucleic acid sequence of interest. These vectors can be prepared from various types of retrovirus, such as, for example, MoMuLV ("murine moloney leukemia virus"; also referred to as MoMLV), MSV ("murine moloney sarcoma virus"), HaSV ("harvey sarcoma virus"), SNV ("spleen necrosis virus"), RSV ("rous sarcoma virus") or the Friend virus.

To construct recombinant retroviruses comprising a sequence encoding the ABC1 protein, placed under the control of a regulatory nucleic acid according to the invention, a plasmid comprising, for example, the LTRs, the encapsidation sequence and said coding sequence is generally constructed, and then used for transfecting a so-called encapsidation cell line which is capable of providing, in trans, the retroviral functions deficient in the plasmid. Generally, encapsidation lines are thus capable of expressing gag, pol and env genes. Such encapsidation lines have been described in the prior art, for example, the line PA317 (U.S. Pat. No. 4,861,719); the line PsiCRIP (WO 90/02806) and the line GP+envAm-12 (WO 89/07150). Moreover, the recombinant retroviruses can comprise modifications in the LTRs so as to eliminate transcriptional activity, as well as extended encapsidation sequences comprising a portion of the gag gene (Bender et al., J. Virol. 61 (1987) 1639). The recombinant retroviruses produced may then be purified by conventional techniques.

To implement the present invention, it is advantageous to use a defective recombinant adenovirus. The results given below indeed demonstrate the properties of adenoviruses which are advantageous for expressing, in vivo, a protein having cholesterol transport activity. The adenoviral vectors according to the invention are advantageous for direct administration in vivo of a purified substance or for transforming cells, for example, autologous cells, ex vivo, with a view to implanting them. In addition, the adenoviral vectors according to the invention also have advantages, such as, for example, their very high infection efficiency, which makes it possible to carry out infections using small volumes of viral suspension.

According to another embodiment of the invention, a producer line for retroviral vectors containing a regulatory nucleic acid according to the invention and the sequence encoding the ABC1 protein is used for an in vivo implantation. The lines which can be used to this end are, for example, the cells PA317 (U.S. Pat. No. 4,861,719), PsiCrip (WO 90/02806) and GP+envAm-12 (U.S. Pat. No. 5,278, 056), which are modified to allow production of a retrovirus containing a nucleic acid sequence encoding an ABC1 protein according to the invention. For example, totipotent stem cells, which are precursors of the blood cell lines, can be sampled and isolated from the individual. These cells, which are put into culture, can then be transfected with the retroviral vector containing the sequence encoding the ABC1 protein, under the control of its own promoter. These cells are then reintroduced into the individual. The differentiation of these cells will be the origin of blood cells which express the ABC1 protein, for example, the origin of monocytes which, when transformed into macrophages, participate in removing cholesterol from the arterial wall. These macrophages expressing the ABC1 protein will have an increased capacity for metabolizing excess cholesterol, and will make it available at the cell surface for its removal by the primary acceptors of membrane cholesterol.

In one embodiment of the present invention, in the vectors of the invention, the sequence encoding the ABC1 protein is placed under the control of a regulatory nucleic acid according to the invention, comprising the regulatory elements which allow its expression in the infected cells and, for example, the regulatory elements of type PPAR.

In another embodiment, the vectors of the invention comprise the sequence encoding the ABC1 protein which is placed under the control of a regulatory nucleic acid comprising a region ranging from the nucleotide at position +108 to the nucleotide at position −2228, with respect to the transcription start site as set forth in sequence SEQ ID No. 1.

Again, in another embodiment, the vectors of the invention comprise the sequence encoding the ABC1 protein which is placed under the control of a regulatory nucleic acid comprising the core promoter sequence and the proximal 200 bp of the ABC1 gene promoter.

As indicated above, the present invention also concerns any use of a virus as described above for preparing a pharmaceutical composition intended for treating and/or for preventing pathologies linked to cholesterol transport.

The present invention also concerns a pharmaceutical composition comprising one or more defective recombinant viruses as described above. These pharmaceutical compositions can be formulated with a view to topical, oral, parenteral, intranasal, intravenous, intramuscular, subcutaneous, intraocular, transdermal, etc. administration. In one embodiment of the present invention, the pharmaceutical compositions of the invention contain a pharmaceutically acceptable vehicle for an injectable formulation, for example, for an intravenous injection, such as for example, into the portal vein of the patient. They can be, for example, isotonic, sterile solutions or dry, for example, freeze-dried, compositions which, upon addition, depending on the case, of sterilized water or physiological saline, allow the constitution of injectable solutions. Direct injection into the portal vein of the patient is advantageous since it makes it possible to target the infection in the liver, and thus to concentrate the therapeutic effect on this organ.

The doses of defective recombinant viruses used for the injection can be adjusted as a function of various parameters, and, for example, as a function of the viral vector, the method of administration used, the pathology concerned or the desired duration of the treatment. In general, the recombinant adenoviruses according to the invention are formulated and administered in the form of doses between $10^4$ and $10^{14}$ pfu/ml, and for example, $10^6$ to $10^{10}$ pfu/ml. The term pfu ("plaque forming unit") corresponds to the infectious power of a viral solution, and is determined by infecting a suitable cell culture and measuring, generally after 48 hours, the number of plaques of infected cells. The techniques for determining the pfu titer of a viral solution are well documented in the literature.

As regards retroviruses, the compositions according to the invention can directly comprise the producer cells, with a view to implanting them.

In this respect, another embodiment of the invention concerns any mammalian cell infected with one or more defective recombinant viruses as described above. For example, the invention concerns any population of human cells infected by these viruses. They can be, for example, cells of blood origin (totipotent stem cells or precursors), fibroblasts, myoblasts, hepatocytes, keratinocytes, smooth muscle cells, endothelial cells, glial cells, etc.

The cells according to the invention can be derived from primary cultures. These primary cultures can be sampled by any technique known to persons skilled in the art, and then put into culture under conditions which allow their proliferation. As regards fibroblasts, they can easily be obtained from biopsies, for example, according to the technique described by Ham [Methods Cell. Biol. 21a (1980) 255]. These cells can be used directly for the infection with the viruses or stored, for example, by freezing, to establish autologous banks, with a view to later use. The cells according to the invention can also be secondary cultures, obtained for example, from pre-established banks (see for example, EP 228458, EP 289034, EP 400047, EP 456640).

The cultured cells are then infected with the recombinant viruses, to confer upon them the capacity of producing a biologically active ABC1 protein. The infection is carried out in vitro according to techniques known to persons skilled in the art. For example, according to the type of cell used and the virus copy number desired per cell, persons skilled in the art can adjust the multiplicity of infection, and optionally, the number of infection cycles carried out. It is clearly understood that the method should be performed under suitable sterile conditions when the cells are intended for an administration in vivo. The doses of recombinant virus used for the infection of the cells can be adjusted by persons skilled in the art according to the desired aim. The conditions described above for the administration in vivo can be applied to the infection in vitro. For the infection with retroviruses, it is also possible to coculture the cells whose infection is desired with producer cells for the recombinant retroviruses according to the invention. This makes it possible to dispense with purifying the retroviruses.

Another subject of the invention concerns an implant comprising mammalian cells infected with one or more defective recombinant viruses as described above or recombinant virus producer cells, and an extracellular matrix. In one embodiment of the present invention, the implants according to the invention comprise $10^5$ to $10^{10}$ cells. For example, they may comprise $10^6$ to $10^8$ cells.

In addition, in the implants of the invention, the extracellular matrix may comprise a gelling compound and optionally a support for anchoring the cells.

Various types of gelling agent can be used to prepare the implants according to the invention. The gelling agents may be used for embedding the cells in a matrix having the constitution of a gel, and to promote the anchoring of the cells onto the support, when needed. Various cell adhesion agents can thus be used as gelling agents, such as, for example, collagen, gelatin, glycosaminoglycans, fibronectin, lectins, etc. In one embodiment of the present invention, collagen is chosen as a gelling agent. It can be collagen of human, bovine or murine origin. For example, type I collagen is used.

As indicated above, the compositions according to the invention may advantageously comprise a support for anchoring the cells. The term "anchoring" refers to any form of biological and/or chemical and/or physical interaction which leads to the adhesion and/or binding of the cells onto the support. Moreover, the cells can either cover the support used, or penetrate inside this support, or both. In the context of the invention, a nontoxic and/or biocompatible solid support may be used. For example, polytetrafluoroethylene (PTFE) fibers or a support of biological origin can be used.

The present invention thus offers an effective means for treating or preventing the pathologies linked to cholesterol transport, such as obesity, hypertriglyceridemia or, in the field of cardiovascular disorders, myocardial infarction, angina, sudden death, heart failure and cerebrovascular accidents.

In addition, this treatment can concern both humans and any animal such as sheep, cattle, domestic animals (dogs, cats, etc.), horses, fish, etc.

Recombinant Host Cells

The invention also concerns a recombinant host cell comprising at least one of the nucleic acids of the invention chosen from sequence SEQ ID No. 1, SEQ ID No. 2, SEQ ID No. 3, SEQ ID No. 4, SEQ ID No. 5, SEQ ID No. 6, SEQ ID No. 7, and SEQ ID No. 8, for example, a nucleic acid of sequence chosen from SEQ ID No. 1, SEQ ID No. 2, SEQ ID No. 3, SEQ ID No. 4 and SEQ ID No. 5.

According to another aspect, the invention also relates to a recombinant host cell comprising a recombinant vector as described above.

Host cells according to the invention are, for example, as follows:

a) prokaryotic host cells: strains of *Escherichia coli* (strain DH5-α), of *Bacillus subtilis*, of *Salmonella typhimurium*, or strains from species such as *Pseudomonas, Streptomyces and Staphylococus;* b) eukaryotic host cells: HeLa cells (ATCC No. CCL2), Cv 1 cells (ATCC No. CCL70), COS cells (ATCC No. CRL 1650), Sf-9 cells (ATCC No. CRL 1711), CHO cells (ATCC No. CCL-61) or 3T3 cells (ATCC No. CRL-6361), or cells of the line Hepa1-6 referenced at the American Type Culture Collection (ATCC, Rockville, Md., United States of America).

c) cells in primary culture, originating from an individual in whom the expression of a nucleic acid of interest, placed under the control of a regulatory nucleic acid according to the invention, is desired.

d) indefinitely-multiplying cells (cell lines), obtained from the cells in primary culture in c) above, according to the techniques well known to persons skilled in the art.

Screening Methods

In vitro Screening Method

The invention provides methods for treating an individual affected by a pathology linked to the level of expression of the ABC1 protein. For example, such a treatment method consists in administering to the individual a compound which modifies the expression of the ABC1 gene, and which can be identified according to diverse in vitro screening methods as defined below.

A first method consists in identifying compounds which modify the expression of the ABC1 gene. According to such a method, cells expressing the ABC1 gene are incubated with a candidate substance or molecule to be tested, and the level of expression of the ABC1 messenger RNA, or the level of production of the ABC1 protein, is then determined.

The levels of ABC1 messenger RNA can be determined with Northern-type gel hybridization, which is well known to persons skilled in the art. The levels of ABC1 messenger RNA can also be determined by methods using PCR or the technique described by WEBB and HURSKAINEN (1996, Journal of Biomolecular Screening, vol. 1: 119).

The levels of production of the ABC1 protein can be determined by immunoprecipitation or immunochemistry, using an antibody which specifically recognizes the ABC1 protein.

According to another method for screening a candidate molecule or substance which modifies the activity of a regulatory nucleic acid according to the invention, a nucleotide construct as defined above, comprising a regulatory nucleic acid according to the invention and a reporter polynucleotide placed under the control of the regulatory nucleic acid, is used, said regulatory nucleic acid comprising at least one basic promoter and at least one regulatory element from one of the sequences SEQ ID No. 1 and SEQ ID No. 2, a regulatory nucleic acid comprising a region ranging from nucleotides −2228 to +108 of sequence SEQ ID NO: 1, or a regulatory nucleic acid comprising the core promoter and the 200 pb proximal of the ABC1 gene promoter The reporter polynucleotide can be a gene encoding a detectable protein, such as a gene encoding a luciferase.

According to such a screening method, the cells are stably or transiently transfected with the polynucleotide construct containing the regulatory nucleic acid according to the invention and the reporter polynucleotide.

The transformed cells are then incubated in the presence or absence of the candidate molecule or substance to be tested, for a sufficient time, and then the level of expression of the reporter gene is determined. The compounds which induce a statistically significant change in the expression of the reporter gene (either an increase or, on the contrary, a decrease in the expression of the reporter gene) are then identified and, where appropriate, selected.

Thus, a subject of the invention is also a method for screening, in vitro, a molecule or a substance which modifies the activity of a regulatory nucleic acid according to the invention, for example, which modifies the transcription of the reporter polynucleotide which is a constituent of a polynucleotide construct according to the invention, characterized in that it comprises:

a) culturing a recombinant host cell comprising a polynucleotide of interest placed under the control of a regulatory nucleic acid according to the invention;

b) incubating the recombinant host cell with the substance or molecule to be tested;

c) detecting the expression of the polynucleotide of interest;

d) comparing the results obtained in c) with the results obtained when the recombinant host cell is cultured in the absence of the candidate molecule or substance to be tested.

The invention also concerns a kit or pack for screening, in vitro, a candidate molecule or substance which is capable of modifying the activity of a regulatory nucleic acid according to the invention, comprising:

a) a host cell transformed with a polynucleotide construct as defined above, comprising a reporter polynucleotide of interest placed under the control of a regulatory nucleic acid according to the invention; and b) optionally, means for detecting the expression of the reporter polynucleotide of interest.

In one embodiment of the present invention, the reporter polynucleotide of interest is the sequence encoding a luciferase. In this embodiment, the regulatory nucleic acid according to the invention is inserted into a vector, upstream of the sequence encoding the luciferase. It can be for example, the vector pGL3-basic (pGL3-b) sold by the company PROMEGA (Madison, Wis., USA).

In this embodiment, the recombinant vector which comprises the sequence encoding the luciferase, placed under the control of a regulatory nucleic acid according to the invention, is transfected into hepatocellular carcinoma cells, such as the cells of the line HepG2, whose luciferase activity is then determined after culturing in the presence or absence of the candidate substance or molecule to be tested.

In this embodiment, pGL3-b vectors containing either the cytomegalovirus (CMV) promoter, the ApoAI promoter or no promoter can be used as controls. For the luciferase activity assay, the transfected cells are washed with a PBS buffer and lysed with 500 µl of lysis buffer (50 mM tris, 150 mM NaCl, 0.02% of sodium azide, 1% of NP-40, 100 µg/ml of AEBSF and 5 µg/ml of leupeptin).

50 µl of the cell lysate obtained are then added to 100 µl of the luciferase substrate (Promega) and the activity measurements are carried out on a spectrophotometric microplate reader, 5 minutes after adding the cell lysate.

The data are expressed in relative units of luciferase activity. The polynucleotide constructs which produce high levels of luciferase activity in the transfected cells are those which contain a regulatory nucleic acid according to the invention, included in the sequence SEQ ID No. 1 which is capable of stimulating transcription.

For the measurements of the levels of expression of messenger RNA in a screening method according to the invention, probes specific for the messenger RNA of the reporter polynucleotide of interest are first prepared, for example, using the kit multiprime labeling kit (sold by the company Amersham Life Sciences, Cleveland, Ohio, USA).

In vivo Screening Method

According to another aspect of the invention, the compositions which modify the activity of a regulatory nucleic acid according to the invention can be identified in vivo in non-human transgenic animals.

According to such a method, a non-human transgenic animal, for example, a mouse, is treated with a candidate molecule or substance to be tested, for example, a candidate substance or molecule which has been selected beforehand by an in vitro screening method as defined above.

After a given duration, the level of activity of the regulatory nucleic acid according to the invention is determined and compared to the activity of an identical nonhuman transgenic animal, for example, an identical transgenic mouse, which has not received the candidate molecule or substance.

The activity of the regulatory nucleic acid according to the invention, which is functional in the transgenic animal, can be determined by diverse methods, for example, measuring the levels of messenger RNA corresponding to the reporter polynucleotides of interest placed under the control of said regulatory nucleic acid, by Northern-type hybridization or by in situ hybridization.

According to one alternative, the activity of the regulatory nucleic acid according to the invention can be determined by measuring the levels of expression of protein encoded by the reporter polynucleotides of interest, for example, by immunohistochemistry, when the polynucleotide reporter of interest comprises an open reading frame encoding a protein which is detectable by such a technique.

For implementing a method for screening, in vivo, a candidate substance or molecule which modifies the activity of a regulatory nucleic acid according to the invention, nonhuman mammals may be used, such as mice, rats or guinea pigs or rabbits, whose genome is modified by inserting a polynucleotide construct comprising a reporter polynucleotide of interest placed under the control of a regulatory nucleic acid according to the invention.

The transgenic animals according to the invention comprise the transgene, i.e. the above-mentioned polynucleotide construct, in a plurality of their somatic and/or germ cells.

The construction of transgenic animals according to the invention can be carried out according to conventional techniques well known to persons skilled in the art. Persons skilled in the art may refer, for example, to the production of transgenic animals, such as to the production of transgenic mice, as described in U.S. Pat. No. 4,873,191 (granted on 10 Oct. 1989), U.S. Pat. No. 5,464,764 (granted on 7 Nov. 1995) and U.S. Pat. No. 5,789,215 (granted on 4 Aug. 1998), the contents of these documents being incorporated herein by way of reference.

Briefly, a polynucleotide construct comprising a regulatory nucleic acid according to the invention and a reporter polynucleotide of interest, placed under the control of the latter, is inserted into a line of stem cells of ES type. The insertion of the polynucleotide construct is carried out for example, by electroporation, as described by Thomas et al. (1987, Cell, Vol. 51:503-512).

The cells which have undergone the electroporation are then screened for the presence of the polynucleotide construct (for example, by selection with the aid of markers, or by PCR, or by Southern-type analysis of DNA on electrophoresis gels), in order to select the positive cells which have integrated the exogenous polynucleotide construct into their genome, when appropriate, following a homologous recombination event. Such a technique is described for example, by Mansour et al. (1988, Nature, Vol. 336:348-352).

Next, the positively selected cells are isolated, cloned and injected into 3.5-day old mouse blastocysts, as is described by Bradley (1987, Production and Analysis of Chimaeric mice. In: E. J. Robertson (Ed., Teratocarcinomas and embryonic stem cells: A practical approach. IRL Press, Oxford, page 113). Blastocysts are then introduced into a female host animal, and the development of the embryo is monitored until full term.

According to one alternative, positively selected cells of ES type are brought into contact with 2.5-day old embryos at an 8- to 16-cell stage (morulae), as described by Wood et al. (1993, Proc. Natl. Acad. Sci. USA, Vol. 90:4582-4585) or by Nagy et al. (1993, Proc. Natl. Acad. Sci. USA, Vol. 90:8424-8428), the ES cells being internalized so as to extensively colonize the blastocyst, including the cells which give rise to the germ line.

The descendants are then tested to determine those which have integrated the polynucleotide construct (the transgene).

A subject of the invention is thus also a non-human transgenic animal whose somatic and/or germ cells have been transformed with a nucleic acid or a polynucleotide construct according to the invention.

The invention also relates to recombinant host cells obtained from a transgenic animal as described above.

Recombinant cell lines originating from a transgenic animal according to the invention can be established in long term culture starting from any tissue from such a transgenic animal, for example, by transfecting primary cell cultures with vectors expressing oncogenes such as the large T antigen of SV40, as described for example, by Chou (1989, Mol. Endocrinol. Vol. 3:1511-1514) and Schay et al. (1991, Biochem. Biophys. Acta, Vol. 1072:1-7).

The invention also relates to a method for screening, in vivo, a candidate molecule or substance which modifies the activity of a regulatory nucleic acid according to the invention, comprising:

a) administering the candidate substance or molecule to a transgenic animal as described above;

b) detecting the level of expression of a reporter polynucleotide of interest placed under the control of the regulatory nucleic acid;

c) comparing the results obtained in b) with the results obtained in a transgenic animal which has not received the candidate substance or molecule.

The invention also relates to a kit or pack for screening, in vivo, a candidate molecule or substance which modifies the activity of a regulatory nucleic acid according to the invention, comprising:

a) a transgenic animal as defined above;
b) optionally, the means for detecting the level of expression of the reporter polynucleotide of interest.

Pharmaceutical Compositions and Compounds

The invention also concerns pharmaceutical compositions intended for preventing or for treating a deficiency in cholesterol metabolism, such as atherosclerosis, for example, in cholesterol transport, and in the reverse transport of cholesterol.

Firstly, a subject of the invention is also a candidate substance or molecule which modifies the activity of a regulatory nucleic acid according to the invention.

The invention also concerns a candidate substance or molecule characterized in that it increases the activity of a regulatory nucleic acid according to the invention, and for example, of a regulatory nucleic acid comprising the sequence SEQ ID No. 1 or SEQ ID No. 3, a region comprising the sequence ranging from nucleotides −2228 to +108 of sequence SEQ ID NO: 1, or a region comprising the core promoter and the 200 pb proximal of the ABC1 gene promoter.

For example, such a substance or molecule which is capable of modifying the activity of a regulatory nucleic acid according to the invention has been selected according to one of the in vitro or in vivo screening methods defined above.

Thus, an individual whose cholesterol metabolism is affected, for example, an individual affected by Tangier disease, is treated by administering to this individual an effective amount of a compound which modifies the activity of a regulatory nucleic acid according to the invention.

Thus, a patient with a weak activity of the ABC1 promoter can be treated with an abovementioned molecule or substance to increase the activity of the ABC1 promoter.

Alternatively, a patient with an abnormally high activity of the ABC1 promoter can be treated with a compound which is capable of decreasing or blocking the activity of the ABC1 promoter.

Such a compound can be a compound which modifies the interaction of at least one transcription factor with the ABC1 promoter or a regulatory element of a regulatory nucleic acid according to the invention.

For example, the compound can inhibit the interaction of one of the transcription factors listed in Table 1 with a regulatory nucleic acid according to the invention.

The compound can also be a compound which modifies the activity of a transcription factor which binds to the ABC1 promoter, or of a regulatory element present on this latter.

A compound of therapeutic interest according to the invention can also be a compound which modifies the interaction of a first transcription factor with a second transcription factor.

As detailed in the analysis of the various transcription factors which are capable of binding to the sequence SEQ ID No. 3, some transcription factors are active only if they are associated with another transcription factor.

A compound of therapeutic interest according to the invention is for example, chosen from nucleic acids, peptides and small molecules. For example, such a compound can be an antisense nucleic acid which binds specifically to a region of the ABC1 promoter or to a regulatory element of a regulatory nucleic acid of ABC1, and which inhibits or decreases the activity of the promoter.

This compound of therapeutic interest can also be an antisense nucleic acid which interacts specifically with a gene encoding a transcription factor which modifies the activity of the ABC1 promoter, such that the interaction of the antisense nucleic acid with the gene encoding the transcription factor which binds to the ABC1 promoter decreases the production of this transcription factor, resulting in an increase or a decrease in the activity of the ABC1 promoter, according to whether the transcription factor increases or, on the contrary, reduces the activity of the ABC1 promoter.

The toxicity and the therapeutic efficacy of the therapeutic compounds according to the invention can be determined according to the standard pharmaceutical protocols, in cells in culture or in experimental animals, for example, to determine the lethal dose $LD_{50}$ (i.e. the dose which is lethal for 50% of the population tested) and the effective dose $ED_{50}$ (i.e. the dose which is therapeutically effective in 50% of the population tested).

For all the compounds of therapeutic interest according to the invention, the effective therapeutic dose can be estimated initially from tests carried out in cell cultures in vitro.

A subject of the invention is also pharmaceutical compositions comprising a therapeutically effective amount of a substance or molecule of therapeutic interest according to the invention.

Such pharmaceutical compositions can be formulated conventionally, using one or more physiologically acceptable vectors or excipients.

Thus, the compounds of therapeutic interest according to the invention, as well as physiologically acceptable salts and solvates thereof, can be formulated for administration by injection or inhalation, or by oral, buccal, parenteral or rectal administration.

Techniques for preparing pharmaceutical compositions according to the invention can be easily found by persons skilled in the art, for example, in the work Remmington's Pharmaceutical Sciences, Mead Publishing Co., Easton, Pa., USA.

For a systemic administration, an injection, including intramuscular, intravenous, intraperitoneal and subcutaneous injections, may be used. In this case, the pharmaceutical compositions according to the invention can be formulated in the form of liquid solutions, for example, in physiologically compatible solutions or buffers.

Method for Detecting an Impairment of the Transcription of the Human ABC1 Gene

A subject of the invention is also methods for determining whether an individual presents a risk of developing a pathology linked to a deficiency in cholesterol metabolism, such as atherosclerosis, for example, in cholesterol transport, and in the reverse transport of cholesterol, such as a risk of developing Tangier disease.

Such methods comprise detecting, in cells from a biological sample originating from an individual to be tested, the presence or absence of a genetic alteration characterized by an impairment of the expression of a gene whose expression is regulated by the ABC1 promoter.

By way of illustration, such genetic alterations can be detected, in order to determine the existence of a deletion of one or more nucleotides in the sequence of a regulatory nucleic acid for ABC1 of sequence SEQ ID No. 1 or SEQ ID No. 2, of the addition of one or more nucleotides or of the substitution of one or more nucleotides in said sequence SEQ ID No. 1 or SEQ ID No. 2.

According to one embodiment of a method for detecting an impairment of the transcription of the ABC1 gene in an individual, the genetic alteration is identified according to a method comprising sequencing all or part of the sequence SEQ ID No. 1, or alternatively all or part of at least the sequence SEQ ID No. 2.

Sequencing primers can be constructed in order to hybridize with a given region of the sequence SEQ ID No. 1. Such sequencing primers are for example, constructed so as to amplify fragments of approximately 250 to approximately 300 nucleotides of the sequence SEQ ID No. 1 or of a complementary sequence.

The fragments amplified, for example, by the PCR method, are then sequenced, and the sequence obtained is compared with the reference sequence SEQ ID No. 1 in order to determine whether one or more deletions, additions or substitutions of nucleotides are found in the sequence amplified from the DNA contained in the biological sample originating from the individual tested.

The invention thus also concerns a method for detecting an impairment of the transcription of the ABC1 gene in an individual, comprising:

a) sequencing a nucleic acid fragment which can be amplified with the aid of at least one nucleotide primer which hybridizes with the sequence SEQ ID No. 1 or SEQ ID No. 2 according to the invention;

b) aligning the sequence obtained in a) with the sequence SEQ ID No. 1 or the SEQ ID No. 2;

c) determining the presence of one or more deletions, additions or substitutions of at least one nucleotide in the sequence of the nucleic acid fragment, with respect to the reference sequence SEQ ID No. 1 or SEQ ID NO. 2.

Oligonucleotide probes which hybridize with a region of the sequence SEQ ID No. 1 or the sequence SEQ ID No. 2 in which an alteration in the sequence has been determined during the implementation of the detection method described above also form part of the invention.

Alternatively, oligonucleotide probes which hybridize specifically with a corresponding region of the sequence SEQ ID No. 1 or of the sequence SEQ ID No. 2, for which one or more deletions, additions or substitutions of at least one nucleotide have been determined in an individual., also form part of the invention.

Such oligonucleotide probes constitute means for detecting alterations in the regulatory sequence for the ABC1 gene and thus also means for detecting a predisposition to developing a pathology linked to a deficiency in cholesterol metabolism, such as atherosclerosis or Tangier disease.

A subject of the invention is thus also a kit or pack for detecting an impairment of the transcription of the ABC1 gene in an individual, comprising:

a) one or more primers which hybridize with a region of the sequence SEQ ID No. 1 or of the sequence SEQ ID No. 2;

b) optionally, the means required for carrying out an amplification reaction.

A subject of the invention is also a kit or pack for detecting an impairment of the transcription of the ABC1 gene in an individual, comprising:

a) one or more oligonucleotide probes as defined above;

b) optionally, the reagents required for carrying out a hybridization reaction.

The nucleic acid fragments derived from any one of the nucleotide sequences SEQ ID No. 1 to 8 are thus useful for detecting the presence of at least one copy of a regulatory nucleotide sequence for the ABC1 gene or of a fragment or of a variant (containing a mutation or a polymorphism) of the latter in a sample.

The nucleotide probes or primers according to the invention comprise at least 8 consecutive nucleotides of a nucleic acid chosen from the group consisting of the sequences SEQ ID No. 1 to 8, or of a nucleic acid of complementary sequence.

For example, nucleotide probes or primers according to the invention will have a length chosen from 10, 12, 15, 18, 20 to 25, 35, 40, 50, 70, 80, 100, 200, 500, 1000, or 1500 consecutive nucleotides of a nucleic acid according to the invention, such as a nucleic acid of nucleotide sequence chosen from the sequences SEQ ID No. 1, SEQ ID No. 2, SEQ ID No. 3, SEQ ID No. 4, SEQ ID No. 5, SEQ ID No. 6, SEQ ID No. 7, and SEQ ID No. 8.

Alternatively, a nucleotide probe or primer according to the invention will consist of and/or will comprise the fragments with a length chosen from 12, 15, 18, 20, 25, 35, 40, 50, 100, 200, 500, 1000, and 1500 consecutive nucleotides of a nucleic acid according to the invention, or a nucleic acid chosen from the sequences SEQ ID No. 1, SEQ ID No. 2, SEQ ID No. 3, SEQ ID No. 4, SEQ ID No. 5, SEQ ID No. 6, SEQ ID No. 7, and SEQ ID No. 8, or of a nucleic acid of complementary sequence.

The definition of a nucleotide probe and primer according to the invention thus encompasses oligonucleotides which hybridize, under the high stringency hybridization conditions defined above, with a nucleic acid chosen from the sequences SEQ ID No. 1, SEQ ID No. 2, SEQ ID No. 3, SEQ ID No. 4, SEQ ID No. 5, SEQ ID No. 6, SEQ ID No. 7, and SEQ ID No. 8 or with a complementary sequence of these sequences.

Examples of primers and primer pairs for amplifying various regions of the ABC1 gene are represented below.

It is for example, the primer pair represented by the primer of sequence SEQ ID No. 12: 5'-TTG CCG TCG ACT GTT TTG GGT AGT TT-3' and the primer of sequence SEQ ID No. 13: 5'-GCC CTG TCG ACC GGC TCT GTT GGT G-3'.

A nucleotide primer or probe according to the invention can be prepared by any suitable method well known to persons skilled in the art, including by cloning and restriction enzyme action, or by direct chemical synthesis according to techniques such as the phosphodiester method of Narang et al. (1979) or of Brown et al. (1979), the diethylphosphoramidite method of Beaucage et al. (1980) or the technique on a solid support described in EU Patent No. EP 0 707 592.

Each of the nucleic acids according to the invention, including the oligonucleotide probes and primers described above, can be labeled, if desired, by incorporating a detectable label, by spectroscopic, photochemical, biochemical, immunochemical or chemical means.

For example, such labels can comprise radioactive isotopes ($32P$, $33P$, $3H$, $35S$), fluorescent molecules (5-bromodeoxyuridine, fluorescein, acetyl-aminofluorene, digoxigenin) or ligands such as biotin.

The labeling of the probes is for example, carried out by incorporation of labeled molecules into the polynucleotides by primer extension, or by addition onto the 5' or 3' ends.

Examples of nonradioactive labeling of nucleic acid fragments are described, for example, in French Patent No. FR 78 109 75 or in the articles by Urdea et al. (1988) or Sanchez-pescador et al. (1988).

Advantageously, the probes according to the invention can have structural properties of a type which enables an amplification of the signal, such as the probes described by Urdea et al. (1991), or in European Patent No. EP-0 225 807 (Chiron).

The oligonucleotide probes according to the invention can be used, for example, in Southern-type hybridizations to genomic DNA.

The probes according to the invention can also be used for detecting PCR amplification products or for detecting mismatches.

Nucleotide probes or primers according to the invention can be immobilized on a solid support. Such solid supports are well known to persons skilled in the art, and comprise surfaces of the wells of microtitration plates, polystyrene beds, magnetic beds, nitrocellulose bands or microparticles such as latex particles.

Consequently, the present invention also concerns a method for detecting the presence of a nucleic acid as described above in a sample, said method comprising:

1) bringing one or more nucleotide probes according to the invention into contact with the sample to be tested;

2) detecting the complex possibly formed between the probe(s) and the nucleic acid present in the sample.

According to one embodiment of the detection method according to the invention, the oligonucleotide probe(s) are immobilized on a support.

According to another aspect, the oligonucleotide probes comprise a detectable label.

The invention also concerns a pack or kit for detecting the presence of a nucleic acid according to the invention in a sample, said pack comprising:

a) one or more nucleotide probes as described above;

b) optionally, the reagents required for the hybridization reaction.

According to a first aspect, the detection pack or kit is characterized in that the probe(s) is (are) immobilized on a support.

According to a second aspect, the detection pack or kit is characterized in that the oligonucleotide probes comprise a detectable label.

According to one embodiment of the detection kit described above, such a kit will comprise a plurality of oligonucleotide probes in accordance with the invention, which may be used for detecting target sequences of interest, or alternatively detecting mutations in the coding regions or the noncoding regions of the nucleic acids according to the invention, for example, of the nucleic acids of sequences chosen from SEQ ID No. 1, SEQ ID No. 2, SEQ ID No. 3, SEQ ID No. 4, and SEQ ID No. 5 or the nucleic acids of complementary sequence.

Thus, the probes according to the invention which are immobilized on a support can be ordered in matrices such as "DNA chips". Such ordered matrices have been described, for example, in U.S. Pat. No. 5,143,854 and in PCT Applications No. WO 90/150 70 and 92/10092.

Support matrices onto which oligonucleotide probes have been immobilized at a high density are, for example, described in U.S. Pat. No. 5,412,087 and in PCT Application No. WO 95/11995.

The nucleotide primers according to the invention can be used to amplify any one of the nucleic acids according to the invention, and for example, all or part of a nucleic acid of sequences chosen from SEQ ID No. 1, SEQ ID No. 2, SEQ ID No. 3, SEQ ID No. 4, and SEQ ID No. 5, or a variant of this nucleic acid.

Another subject of the invention concerns a method for amplifying a nucleic acid according to the invention, and for example, a nucleic acid sequence chosen from SEQ ID No. 1, SEQ ID No. 2, SEQ ID No. 3, SEQ ID No. 4, and SEQ ID No. 5, or a fragment or a variant of this nucleic acid, contained in a sample, said method comprising:

a) bringing the sample, in which the presence of the target nucleic acid is suspected, into contact with a pair of nucleotide primers, of which the hybridization position is located respectively on the 5' side and on the 3' side of the region of the target nucleic acid whose amplification is sought, in the presence of the reagents required for the amplification reaction; and b) detecting the amplified nucleic acids.

To implement the amplification method as described above, any one of the nucleotide primers described above will advantageously be used.

A subject of the invention is also a pack or kit for amplifying a nucleic acid according to the invention, and for example, all or part of a nucleic acid sequence chosen from SEQ ID No. 1, SEQ ID No. 2, SEQ ID No. 3, SEQ ID No. 4, and SEQ ID No. 5, said pack or kit comprising:

a) a pair of nucleotide primers in accordance with the invention, the hybridization position of which is located respectively on the 5' side and on the 3' side of the target nucleic acid whose amplification is sought;

b) optionally, the reagents required for the amplification reaction.

Such an amplification pack or kit will advantageously comprise at least one pair of nucleotide primers as described above.

The following examples are intended to illustrate the invention without limiting the scope thereof.

EXAMPLES

Example 1

Tissue Distribution of the ABC1 Gene Transcripts According to the Invention

The expression profile of the polynucleotides according to the present invention was determined according to the reverse transcription-coupled PCR and Northern blot analysis protocols described, for example, by Sambrook et al. (ref. CSH Sambrook, J., Fritsch, E. F., and Maniatis, T. (1989). "Molecular Cloning: A Laboratory Manual", 2nd Ed., Cold Spring Harbor Laboratory Press, Cold Spring Harbor, N.Y.).

For example, in the case of an analysis by reverse transcription, a pair of primers which have been synthesized from the human ABC1 gene full-length cDNA of sequence SEQ ID No. 10 was used for detecting the corresponding cDNA.

The polymerase chain reaction (PCR) was carried out on matrices of cDNAs corresponding to reverse-transcribed polyA$^+$ mRNAs (Clontech). The reverse transcription into cDNA was carried out with the enzyme Superscript II (GibcoBRL, Life Technologies), according to the conditions described by the manufacturer.

The polymerase chain reaction was carried out according to standard conditions, in 20 µl of reaction mixture, with 25 ng of the cDNA preparation. The reaction mixture was composed of 400 µM of each of the dNTPs, of 2 units of Thermus aquaticus (Taq) DNA polymerase (Ampli Taq Gold; Perkin Elmer), of 0.5 µM of each primer, of 2.5 mM MgCl$_2$ and of PCR buffer. Thirtyfour cycles of PCR (denaturation for 30 s at 94° C., hybridization of 30 s, broken down as follows during 34 cycles: 64° C. 2 cycles, 61° C. 2 cycles, 58° C. 2 cycles and 55° C. 28 cycles, and an elongation of one minute per kilobase at 72° C.) were carried out after a first denaturation at 94° C. for 10 min, in a Perkin Elmer 9700 thermocycler machine. The PCR reactions were visualized on agarose gels by electrophoresis. The cDNA fragments obtained could be used as probes for a Northern blot analysis and could also be used for exactly determining the polynucleotide sequence.

In the case of an analysis by Northern blot, a cDNA probe produced as described above was labeled with $^{32}$P, using the High Prime DNA labeling system (Boehringer), according to the instructions indicated by the manufacturer. After labeling, the probe was purified on a Sephadex G50 microcolumn (Pharmacia), according to the instructions indicated by the manufacturer. The labeled and purified probe was then used for detecting the expression of the mRNAs in various tissues.

The Northern blot which contained samples of RNA from various human tissues ((Multiple Tissue Northern, MTN, Clontech) Blot 2, reference 77759-1) was hybridized with the labeled probe.

The protocol which was followed for the hybridizations and washes were either directly that described by the manufacturer (Instruction manual PT1200-1), or an adaptation of this protocol using the methods which are known to persons skilled in the art, and which are described for example, in F. Ausubel et al. (1999). For example, the temperatures of prehybridization and of hybridization in the presence of formamide may thus be varied.

For example, the following protocol was used:

1—Membrane Competition and Prehybridization:
Mixed: 40 µl salmon sperm DNA (10 mg/ml)
+40 µl human placental DNA (10 mg/ml)
Denatured for 5 min at 96° C., then immersed the mixture in ice.
Removed the 2×SSC buffer and poured 4 ml of formamide mix into the hybridization tube containing the membranes.
Added the mixture of the two denatured DNAs.
Incubation at 42° C. for 5 to 6 hours, with rotation.

2—Labeled Probe Competition:
Added 10 to 50 µl Cot I DNA to the labeled and purified probe, according to the amount of repeated sequences.
Denatured for 7 to 10 min at 95° C.
Incubated at 65° C. for 2 to 5 hours.

3—Hybridization:
Removed the prehybridization mix.
Mixed 40 µl salmon sperm DNA +40 µl human placental DNA; denatured 5 min at 96° C., then immersed in ice.
Added 4 ml of formamide mix, the mixture of the two DNAs and the denatured labeled probe/Cot I DNA to the hybridization tube.
Incubated for 15 to 20 hours at 42° C., with rotation.

4—Washes:
One wash at room temperature in 2×SSC to rinse.
Twice 5 minutes at room temperature, 2×SSC and 0.1% SDS, at 65° C.
Twice 15 minutes at 65° C., 1×SSC and 0.1% SDS, at 65° C.

After hybridization and washing, the blot was analyzed after overnight exposure in contact with a phosphor screen, which was revealed with the aid of Storm (Molecular Dynamics, Sunnyvale, Calif.).

Example 2

Analysis of the Profile of Gene Expression for Tangier Disease

Verification of the impairment in the expression level of the ABC1 gene, which leads to the Tangier cellular phenotype determined by hybridization of these sequences with probes corresponding to the mRNAs which originate from fibroblasts from individuals possibly suffering from the disease, according to the methods described below:

1. Preparation of Total RNAs, of Poly(A)+ mRNAs and of cDNA Probes

The total RNAs were obtained from cell cultures of the fibroblasts from individuals who were normal or suffering from Tangier disease, by the guanidine isothiocyanate method (Chomczynski & Sacchi, 1987). The poly(A)+ mRNAs were obtained by affinity chromatography on cellulose-oligo(dT) columns (Sambrook et al., 1989), and the cDNAs used as probes were obtained by RT-PCR (DeRisi et al., 1997) with oligonucleotides which were labeled with a fluorescent product (Amersham Pharmacia Biotech; CyDye™).

2. Hybridization and Detection of Expression Levels

The glass fiber membranes containing the sequences according to the present invention which correspond to the Tangier gene were hybridized with the cDNA probes, which were obtained from fibroblasts (Lyer et al., 1999). Using the Amersham/Molecular Dynamics system (Avalanche Microscanner™) allowed the quantification of the expressions of the sequence products in the healthy or affected cell type.

Example 3

Use of IL-1Beta-Expressing THP-1 Macrophages for Screening Molecules which Activate or Inhibit the Expression of the ABC-1 Gene The principle of this assay is that any substance which modifies the synthesis activity of the ABC1 protein has repercussions on the synthesis of IL-1beta.

a) The macrophage cells of the THP-1 lines, which are human monocytic leukemia cells, are a model of differentiated macrophages. These cells were cultured in an RPMI 1640 medium supplemented with 10% of fetal calf serum, in multiwell plates, at a density of 2 105 cells per wells.

b) For the assay per se, the cells were then washed and placed in an RPMI 1640 medium containing 1 mg/ml of purified human albumin fraction IV.

c) The products were added into the extracellular medium. Simultaneously, the cells were then activated by addition of lipopolysaccharides (LPS) for 3 hours, at 1 µg/ml, followed by an incubation of 30 minutes in the presence of ATP at 5 mmol/L.

d) The concentrations of IL-1beta and of control IL-1alpha, tumor necrosis factor alpha (TNFalpha) and IL-6 were determined with ELISA kits, according to the manufacturers' instructions (R&D System; human IL-1beta Chemiluminescent ELISA reference QLB00). The variations in IL-1beta mRNA, which was not supposed to be affected, were evaluated by the Northern blot technique, using the corresponding probe.

Example 4

Expression of a Gene of Interest Under the Control of a Regulatory Nucleic Acid for the Human ABC1 Gene According to the Invention 4.1 Materials and Methods 4.1.1 Construction of Expression Plasmids Containing a Regulatory Nucleic Acid for the Human ABC1 Gene.

The region of the regulatory acid for the human ABC1 gene which ranges from the nucleotide at position −-995 up to the nucleotide at position +120, with respect to the transcription start site, was amplified by the PCR technique, with the aid of the following pair of primers:
forward primer S995 (SEQ ID No. 12), of sequence 5'-TTG CCG TCG ACT GTT TTG GGT AGT TT-3'; and
reverse primer +220R (SEQ ID No. 13), of sequence 5'-GCC CTG TCG ACC GGC TCT GTT GGT-3',
From human genomic DNA present in a BAC vector from a collection of human BAC vectors.

The DNA fragment amplified was digested with the restriction endonuclease Sal 1, and then inserted into the vector PXP1 described by Nordeen et al. (1988, BioTechniques, 6: 454-457), at the Sal 1 restriction site of this vector.

The insert was then sequenced.

4.1.2. Cell Culture and Transfection

Cells of the Hepa1-6 line (ATCC, Rockville, Md., USA) were cultured in the medium E-MEM (Minimum Essential Medium with Earle's Salts), to which 10% (v/v) of fetal calf serum (BioWhittaker, Walkersville, Md.) was added.

Approximately $1.5 \times 10^5$ cells were distributed into each of the wells of a 12-well (2.5 cm) culture plate, and were cultured until approximately 50 to 70% confluence, and were then cotransformed with 1 μg of the plasmid Sal-Lucif and 0.5 μg of the control vector pBetagel (CloneTech Laboratories Inc., Palo Alto, Calif., USA) using the Superfectin Reagent Kit pack (QIAGEN Inc., Valencia, Calif., USA). Two hours after adding the DNA, the culture medium was removed, and replaced with complete AMEM (Minimum Essential Medium Eagle's Alpha Modification) medium.

After a duration of twenty hours, the cells were placed in fresh medium such as DMEM (Dulbecco's Minimum Essential Medium), to which 2 μg/ml of glutamine, 100 units/ml of streptomycin and 0.1% of bovine serum albumin (BSA, Fraction V) were added, in the presence or absence of 50 μg/ml of cholesterol (Sigma Chemical Co., St Louis, Missouri, Mo., USA).

The cells were recovered 16 hours after the final change of medium using a lysis solution from the Tropix Luciferase Assay Kit pack (Tropix Inc., Bedford, Mass., USA).

The cell lysate was divided into aliquot fractions which were stored at −70° C.

Freshly thawed aliquot fractions were used to quantify the proteins, using the MicroBCA Kit pack (Pierce, Rockford, Ill., USA), as well as to quantify the luciferase and beta-galactosidase production, using, respectively, the Tropix Luciferase Assay Kit and Galacto-Light Plus Kit packs. The assays were carried out according to the manufacturer's recommendations.

4.2 Results

The results are represented in Table 2 below:

TABLE 2

Luciferase production by the cells transfected with a vector containing the luciferase gene placed under the control of a regulatory nucleic acid for the human ABC1 gene according to the invention, in the presence or absence of cholesterol.

| Culture conditions | Luciferase activity | β-Galacto-sidase activity | Normalized activity | Increase in the activity |
|---|---|---|---|---|
| Without cholesterol | 215 523 +/− 20 018 | 29 548 +/− 1342 | 7.29 | — |
| In the presence of cholesterol | 500 126 +/− 100 069 | 37 741 +/− 2813 | 13.25 | 1.82 |

The results above show the capacity of a regulatory acid for the human ABC1 gene according to the invention to direct the expression of a coding sequence placed under its control.

In addition, the regulatory nucleic acid used, which stretches from the nucleotide at position −995 to the nucleotide at position +120, with respect to the transcription start site, and which contains all the PPAR sites identified, was regulated by cholesterol.

Example 5

Characterization of the Transcription Factor Binding Motifs in the Proximal Human ABC1 Gene Promoter 5.1 Materials and Methods 5.1.1 Construction of Reporter Plasmids for Luciferase Assay Plasmids containing mutant SP1, AP1, E-box, LXR and deleted E-box fragments were constructed by site-directed mutagenesis using the overlap PCR method and the PXP1 −995 to +120 bp construct (Previato et al., JBC, 1991, 266:18958-63) as template. The primers listed below were used to amplify −200 to +44 bp of the human ABC1 promoter. Upper-case letters represent wild-type sequence whereas lower-case letters represent mutant sequence.

```
MDistal SP1F   5'TCGCCCGTTTAgGcttgGGcgCCCGGCTC3'      (SEQ ID NO: 14)
MDistal SP1R:  5'GAGCCGGGCgCCcaagCcTAAACGGGCGA3'      (SEQ ID NO: 22)

MProximal SP1F: 5'CAGAGGCCGGGAgGcttgGGcgGGAGGGA3'    (SEQ ID NO: 15)
MProximal SP1R: 5'TCCCTCCcgCCcaagCcTCCCGGCCTCTG3'    (SEQ ID NO: 23)

MAP1F:         5'CGTGCTTTCTGCTGAGgatgcGAACTAC3'       (SEQ ID NO: 16)
MAP1R:         5'GTAGTTCgcatcCTCAGCAGAAAGCACG3'       (SEQ ID NO: 24)

MEBoxF:        5'CGGCTCCtcacggCTTTCTGCTGAGT3'         (SEQ ID NO: 17)
MEBoxR:        5'ACTCAGCAGAAAGccgtgaGGAGCCG3'         (SEQ ID NO: 25)

DEboxF:        5'GCCTCCTTTCTGCTGAGTGACTGA3'           (SEQ ID NO: 18)
DEboxR:        5'GAAAGGAGCCGGGGCCCGCCCCA3'            (SEQ ID NO: 26)

MLXRF:         5'CTTTGtgtGATAGTAAActaCTGCGCTCGGTGCA   (SEQ ID NO: 19)
MLXRR          5'TGCACCGAGCGCAGtagTTACTATCacaCAAAG   (SEQ ID NO: 27)
```

```
                                -continued
S224-HindIII:    5'ACTCCCAAGCTTTGTCGTGG3'              (SEQ ID NO: 20)
44-HindIII:      5'GAGAAGCTTCGGCTCGGCTCTG3'            (SEQ ID NO: 28)
```

S224-HindIII and 44-HindIII were the upstream and downstream primers used for overlap PCR. The Hind III sites are underlined. The resulting fragments which spanned −200 to +44 of the human ABC1 gene were ligated into the HindIII site of the PXP1 luciferase reporter plasmid (Nordeen et al., *Biotechniques*, 1988, 6:454-457). All constructs were confirmed by sequencing.

5.1.2. Cell Culture and Transfection

Murine macrophage RAW 264.7 cells and human embryonic kidney 293 cells (American Type Culture Collection, Rockville, Md.) were grown in Dulbecco's modified Eagle's medium (DMEM) with 10% fetal calf serum (FCS). Approximately $1.5 \times 10^5$ cells were plated in 12-well plates (Costar, Corning, N.Y.), grown to 50-70% confluency and cotransfected with 1.5 µg of the ABC1 promoter-luciferase plasmid and 0.5 µg of the β-galactosidase vector (pCMVβ; Clontech, Palo Alto, Calif.) by using the Superfectin Reagent Kit (Qiagen, Valencia, Calif.). Three hours after addition of DNA, the cells were refed with fresh media containing 10% FCS. Sixteen hours later, cells were washed with phosphate-buffered saline (PBS) and refed with DMEM containing 0.1% bovine serum albumin (BSA) and either 50 µg/ml cholesterol, 2 µg/ml 22-(R)-hydroxycholesterol (22(R)-Hch), 10 µM 9-cis-retinoic acid (9CRA), 10-100 nM estradiol (Sigma, St. Louis, Mo.), 10-100 nM regular insulin (Sigma) or 0.1% ethanol for 24 hours. After harvesting, 10 µl of cell extracts were used for luciferase and β-galactosidase assays by using the Promega dual luciferase assay system (Promega, Madison, Wis.) or the Tropix Galacto-Light Plus Kits, respectively (Tropix, Bedford Mass.). The ratio of luciferase activity in relative light units was divided by the β-galactosidase activity to give a normalized luciferase value.

5.1.3. Gel Mobility Shift Assay

Three double-stranded human ABC1 promoter fragments (Fragment A spanning −171 to −71 bp; Fragment EB spanning −156 to −130 bp and Fragment EB spanning −156 to −130 bp) were end-labeled with $\alpha^{32}$P-dATP using T4 polynucleotide kinase (Lofstrand, Gaithersburg Md.). Nuclear extracts were isolated from unstimulated RAW 264.7 cell and HepG2 cell as well as RAW 264.7 cells after stimulation with the same concentrations of cholesterol and 22(R)-Hch shown above (Paragon Bioservices Inc. Baltimore, Md.). One ng (10,000 cpm) of radiolabelled probe was added to 2.5 µg nuclear extract in 20 ul of a 20 mM TRIS gel shift buffer (pH 7.9) containing 60 mM KCl, 0.2 mM EDTA, 0.5 mM DTT, 0.25 mM PMS, 1.3 mM MgCl, 10% glycerol, 3% Ficoll and 3 µg of double-stranded poly (dIdC) as described (Previato et al., J Biol Chem, 1991, 266:18958-18963) and incubated for 10 minutes on ice followed by 10 minutes at room temperature. The incubated mixture was loaded on a 6% polyacrylamide gel in 0.25×TBE buffer and electrophoresed at 100 V for 90 min followed by autoradiography. For competition assays, nuclear extracts were preincubated for 10 minutes on ice in a 20 µl reaction mixture in the presence or absence of a 100-200-fold excess of double-stranded DNA competitors for Sp1 (−173 to −155 bp), AP1 (−135 to −155 bp), LXR (−54 to −69 bp) and E-box (−158 to −136 bp) before addition of probe. For supershift assays, nuclear extracts were preincubated with antibodies against different E-box binding proteins including Mad1, Mad2, Mad3, Max, c-Myc, MyoD, USF1 and USF2 as well as Sp1, c-Fos, c-Jun, JunB and JunD (Santa Cruz Biotechnology, Santa Cruz, Calif.) on ice for 30 minutes before addition of probe.

5.1.4. DNAse I Protection Assay

End-labelled fragment A was digested with AspHI. The 94 bp fragment was gel-purified from a 10% acrylamide TBE gel (Novex) and added to 14 µl of RAW cell nuclear extract (5.2 µg/µl protein) in gel shift buffer (Example 5.1.3) and incubated on ice for 10 min. One µl of probe (10,000 cpm was added and the mixture was incubated on ice for another 10 min. After 10 min at RT, 20 µl DNaseI digestion buffer (10 mM Tris-HCl pH 8.0, 5 mM $CaCl_2$, 5.0 mM $MgCl_2$) was added, then 15 seconds later DNase I was added and incubated for 1 min 45 sec. DNaseI stop buffer (10 mM Tris-HCl pH 8.0, 0.6M sodium acetate pH 7.0, 0.5% SDS, 100 mM EDTA) was then added. 2.0 µl of protease K at 20 mg/ml were added and the samples were incubated at 37° C. for 30 min. 10 µl of 3M NaOAc and 4.0 µl tRNA (10 mg/ml) were added. Samples were phenol/chloroform extracted and the aqueous phase was precipitated with 2.5 volumes of 100% ethanol. After a 70% ethanol wash, pellets were dissolved in sequencing gel loading buffer, heated and run on an 8% sequencing gel. Naked DNA was digested with DNaseI as described above except that nuclear extract addition and Protease K treatment were omitted. Maxam-Gilbert sequencing was performed as described in Current Protocols in Molecular Biology (Aubusel et al., *Current Protocols in Molecular Biology*, 1994, 2: 12.1-12.11).

5.1.5 Western Analysis

RAW cell nuclear extracts (35 µg protein per lane) from cells stimulated with cholesterol or 22-R-hydroxycholesterol were loaded onto NuPage Bis-Tris 4-12% gradient gels (Invitrogen, Carlsbad, Calif.) and run according to manufacturer's specifications. Proteins were transferred to Immobilon-P PVDF membranes (Millipore Corp, Bedford, Mass.). Antibodies (2 mg/ml stock) were from Santa Cruz Biotechnology, Inc. (Santa Cruz, Calif.) and were used according to manufacturer's specifications. Anti-USF1 C20X (catalog number sc-229X) antibody was used at a dilution of 1/600 and anti-USF2 antibodies C20X (catalog number sc862X) and N18X (catalog number sc861X) were used at a dilution of 1/1000.

5.2.1 Analysis of Binding Motifs in the Proximal Human ABC1 Gene Promoter

To investigate the role of some of the above described transcription factor binding motifs in this region of the human ABC1 gene promoter, i.e., Sp1 (−100 and −166 bp), AP1 (−131 bp), LXR (−69 bp) and E-box (−147 bp), luciferase reporter constructs under the control of the −200 bp human ABC1 promoter, either wild-type (p200-L) or mutated have been generated according to Example 5.1.1. FIG. 2A shows the locations of point mutations introduced into the −200 bp promoter region of the human ABC1 gene.

Figure 2B:
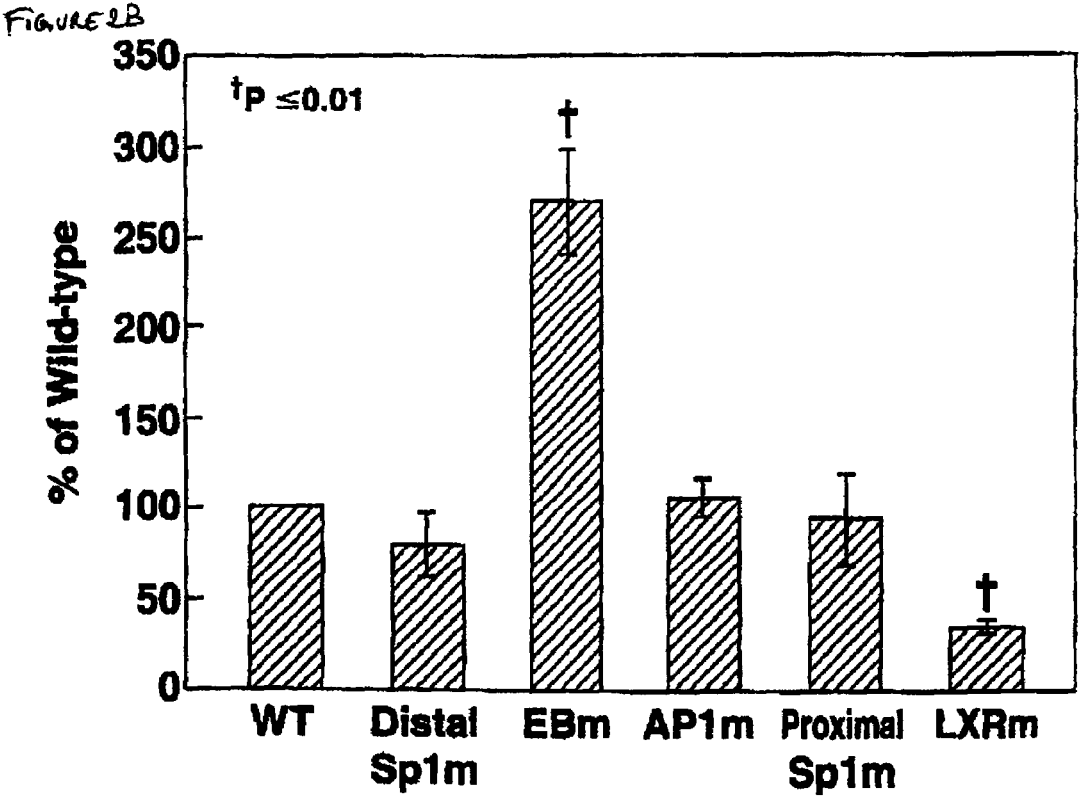
FIG. 2B: displays the luciferase activity in RAW cells after transfection with wildtype and mutant constructs. The data shown represents the mean of 3 independent transfection studies. Values are expressed relative to the wildtype construct.

The effect of these point mutations on the transcriptional activity of the human ABC1 gene in unstimulated RAW cells is illustrated in FIG. 2B. Mutating the distal Sp1 site, the AP1 site and the proximal Sp1 sites had only a minor effect on promoter activity. In contrast, mutation of the E-box caused a strong and significant increase in promoter activity and mutation of the LXR element caused a strong and significant decrease in promoter activity. These results are consistent with binding of a transcriptional repressor to the human ABC1 E-box and binding of a transcriptional activator to the LXR element.

5.2.2 Mutation of the LXR Element Reduces Transcription of the hABC1 Gene

FIG. 3 shows that the LXR element is implicated as the human ABC1 promoter motif responsive to oxysterols. Mutation of the LXR element at −69 bp caused a significant decrease in transcription for unstimulated cells as well as for cells stimulated by cis-retinoic acid (CRA) and 22(R)-hydroxycholesterol (22OH). Mutation of the LXR element also caused a significant decrease in transcription for cholesterol-stimulated cells, presumably due to the intracellular conversion of cholesterol to oxysterols. Thus, the LXR element mediates responsiveness to cholesterol as well as to cis-retinoic acid and to hydroxysterols.

5.2.3 Mutation of the E-box Increases Transcription of the Human ABC1 Gene

Figure 4:
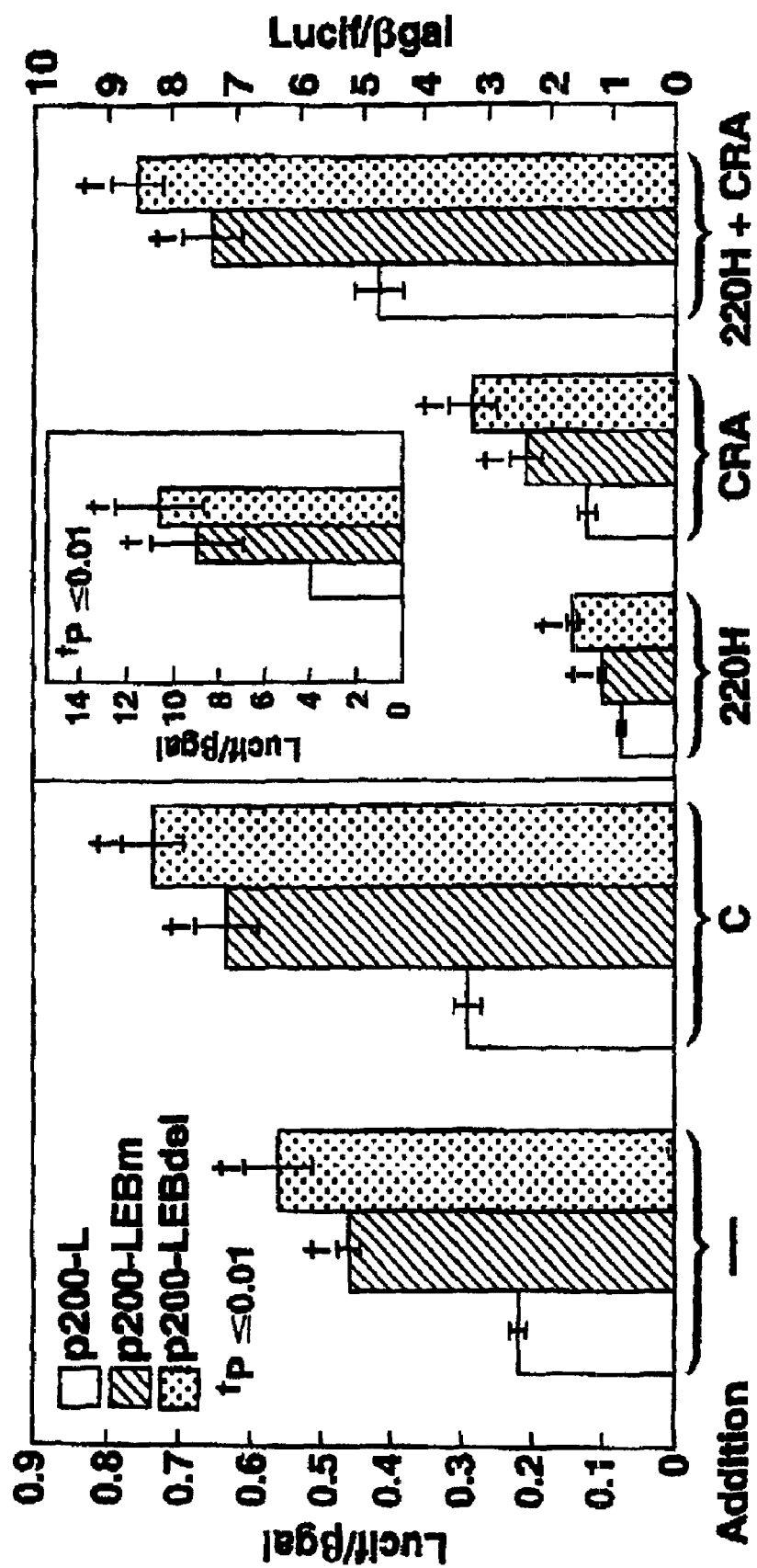
FIG. 4: RAW 264.7 cells were transfected with wild type construct (p200-L), mutant E-box construct (p200-EBm) or the deleted E-box construct (p200-EBd) along with a β-galactosidase expression plasmid. Addition of 50 µg/ml cholesterol, 2 µg/ml 22(R)-HOch, 10 µM 9CRA or, 2 µg/ml 22(R)-HOch plus 10 µM 9CRA were performed. Cell lysates were analyzed for luciferase and β-galactosidase activity. Luciferase values were normalized to β-galactosidase activity and expressed as mean±SEM.

FIG. 4 demonstrates that mutation or deletion of the E-box motif increases transcription of the human ABC1 gene in unstimulated RAW cells by approximately 3-fold and also in RAW cells stimulated with cholesterol (c), cis-retinoic acid (CRA) and oxysterol (22OH) by up to 40-fold. Furthermore, mutation or deletion of the E-box in the proximal human ABC1 promoter had no effect on the stimulatory effect of either CRA or oxysterols. Similar findings were demonstrated for unstimulated and stimulated human embryonal kidney 293 cells. These results indicate that the LXR-mediated activation of ABC1 gene transcription by CRA and oxysterols does not require an intact E-box motif and are consistent with binding of a transcriptional repressor to the E-box in the human ABC1 gene.

Figure 5:
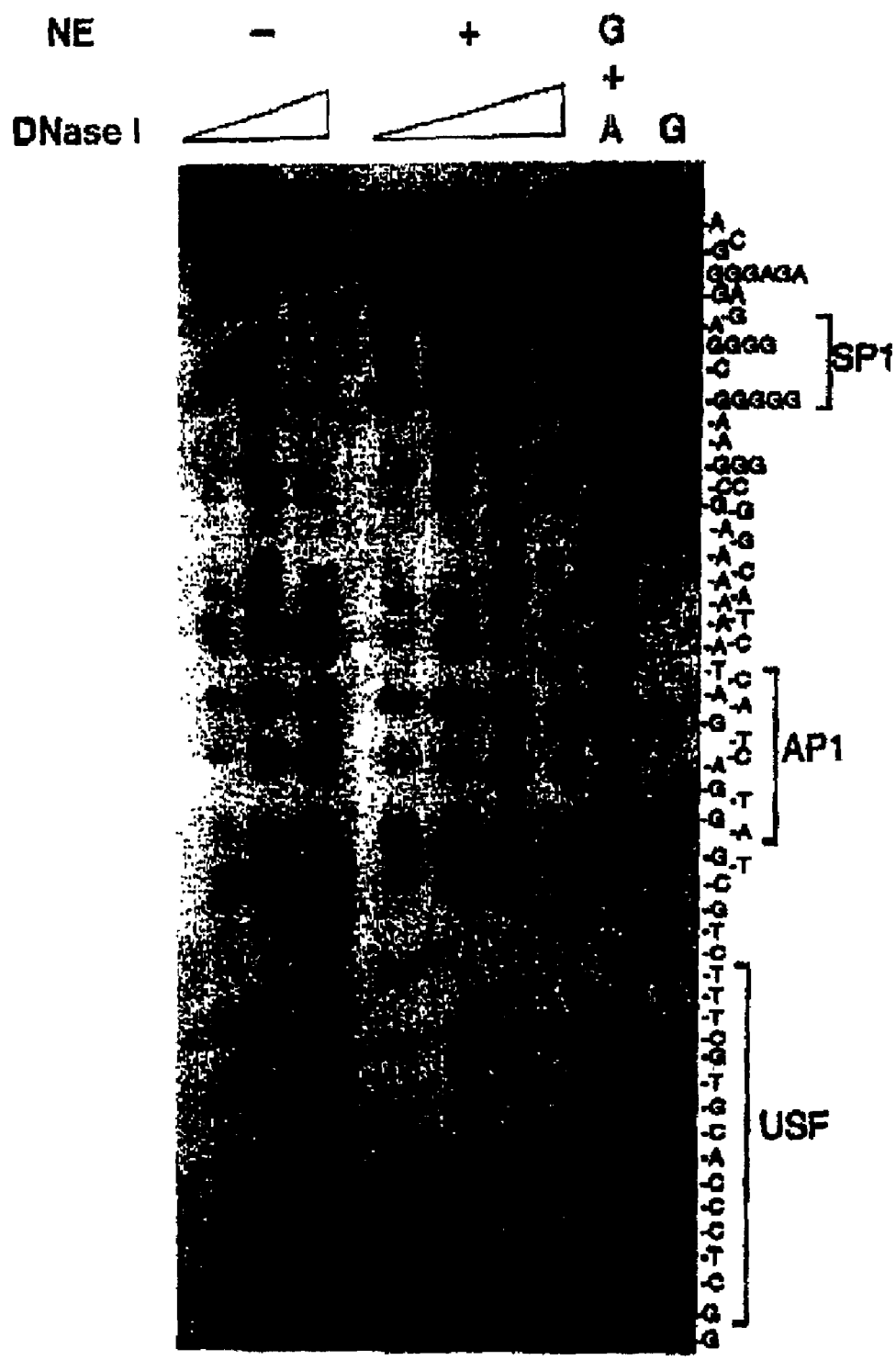
FIG. 5: A radiolabelled fragment (−171 to −77 bp) of the human ABC1 promoter was digested with different concentrations of DNaseI in the presence (+) or absence (−) of RAW cell nuclear extract (NE). The G and G+A ladders from Maxam and Gilbert sequence of the radiolabelled fragment are shown. The nucleotide position relative to the transcriptional start site and location of the Sp1, AP1 and EB motifs in the hABC1 promoter are indicated on the right.

5.2.4 Nuclear Transcription Factors Bind the E-Box in the Human ABC1 Gene Promoter DNaseI footprint analysis of the ABC1 proximal promoter revealed protection of the E-box in the presence of RAW nuclear extracts (FIG. 5) indicative of a protein binding to this region. Consistent with the lack of transcriptional effects observed by independently mutating the AP1 and Sp1 motifs (FIG. 2B), no protection of these potential binding sites in the human ABC1 promoter was evident by footprint analysis (FIG. 5).

To further demonstrate binding of nuclear transcription factors to the E-box motif we performed gel-shift analysis of the human ABC1 promoter (FIG. 6). The probe utilized in FIG. 6B (left) was a 100 bp double-stranded fragment spanning −171 through −71 of the ABC1 promoter (designated Fragment A). Incubation of the radiolabelled probe with nuclear extract isolated from unstimulated RAW cells resulted in a gel shift (FIG. 6B). The shift was abolished when either unlabelled Fragment A (A) or a double-stranded oligonucleotide spanning the E-box (EB) were used as competitors. Competition with the 27 bp fragment encoding a scrambled E-box (EBm) did not abolish the gel shift band. Competition by double-stranded DNA fragments spanning either the proximal or distal Sp1 motifs or the AP1 binding sites did not abolish the gel shift band. Similar results were observed when nuclear extracts from unstimulated 293 cells were utilized.

Gel-shift analysis of the human ABC1 promoter was also performed using either a 27 bp double-stranded probe spanning the E-box (FIG. 6A; Fragment EB; right panel) or an alternative probe containing a scrambled mutant E-box sequence as described above (Fragment EBm). Incubation of the wild-type E-box probe with unstimulated RAW cell nuclear extract resulted in a gel shift, indicating binding of a protein to this probe (FIG. 6B; middle panel). Addition of unlabelled wild-type competitor (EB) eliminated binding. In contrast, competition with the mutant E-box fragment (EBm) did not significantly affect binding to the wild-type E-box. Moreover, using the mutant E-box as a target probe for the binding of cellular nuclear extracts did not result the formation of a gel shift band (FIG. 6B; right panel). This clearly demonstrates specific binding of a protein to the wild-type E-box motif of the human ABC1 gene.

5.2.5 USF Binds the E-Box in the hABC1 Gene Promoter

In the human ABC1 promoter, the E-box is flanked by two C's, leading to a sequence of CCACGTGC. This is a perfect match to the consensus motif for the transcription factor USF. To establish that USF is, in fact the transcription factor that that binds to the E-box in the hABC1 gene promoter, a gel shift analysis utilizing USF-specific antibodies was performed (FIG. 6C). Using the 100-bp fragment as a probe (FIG. 6C, left panel), it was demonstrated that the E-box gel-shifts some protein in the RAW cell nuclear extract. Addition of anti-USF antibodies against either the amino (N) or carboxy (C) terminus of USF1 or USF2 caused a supershift of the gel-shifted probe, confirming the identity of the E-box binding proteins as USF1 and USF2. Antibodies against other E-box binding proteins including Mad1, Mad2, Mad3, Max, c-Myc, and MyoD as well as Sp1, c-Jun, JunB and JunD did not compete or supershift the DNA-protein gel shift band.

Similar results were obtained by preincubating the 27 bp double-stranded fragment spanning the E-box (EB) with anti-USF antibodies (FIG. 6C; right panel). As with the 100 bp gel shift fragment, antibodies specific to other members of the helix-loop-helix family of transcription factors known to also bind the E-box motif did not alter the gel shift band obtained with the 27 bp EB probe. No differences have been shown in the gel shift banding patterns obtained when nuclear extracts isolated from unstimulated RAW cells and RAW cells stimulated with cholesterol or oxysterols were incubated with the EB probe.

This combined data identify USF1 and USF2 as the transcriptional factors that bind to the E-box in the proximal ABC1 promoter and indicate that their binding is not modulated by known activators of ABC1 gene expression.

5.2.6 USF1 and USF2 are Expressed in RAW Cells

The presence of USF in RAW cell nuclear extracts was establish by performing Western blot hybridization analyses utilizing antibodies specific to USF1 (N- and C-terminus) and USF2 (N- and C-terminus). Two major immunoreactive bands of approximately 43 and 44 KDa in size were identified whose expression in RAW cells were not altered by stimulation with cholesterol or oxysterols. Importantly, expression of the 18 kDa mini-USF isoform which lacks the carboxy-terminus transcriptional activating domain (Liu et al., JBC, 1999, 274: 35037-35045; Sirito et al., Nucl Acids Res, 1994, 22:427-433) was not detected in either unstimulated RAW cells or RAW cells incubated for 24 hours with cholesterol or oxysterols.

All articles, patents, and patent applications mentioned in this specification are herein incorporated by reference.

REFERENCES

Altschul S. F. et al., J. Mol. Biol. 1990 215: 403-410.
Altschul S. F. et al., Nucleic Acids Res. 1997 2/5: 3389-3402.
Apfel et al., 1994, Moll. Cell. Biol. 14: 7025-7035.
Ausubel et al., 1999, Current Protocols in Molecular Biology, Green Publishing Associates and Wiley Interscience, N.Y.
Beard et al., Virology 75 (1990) 81.
Beaucage et al., *Tetrahedron Lett* 1981, 22: 1859-1862.
Bender et al., J. Virol. 61 (1987) 1639.
Bernstein et al., Genet. Eng. 7 (1985) 235.
Bodzioch M. et al., Nat Genet. 1999, 22: 347-351.
Bradley, 1987, Production and analysis of Chimaeric Mice. In: E. J. Robertson Ed., Teratocarcinomas and embryonic stem cells; A practical approach. IRL Press, Oxford, page 113.
Breakfield et al., New Biologist 3 (1991) 203.
Brooks-Wilson et al., Nat Genet, 1999, 22: 336-345.
Brown E L. Belagaje R, Ryan M J, Khorana H G, *Methods Enzymol* 1979; 68: 109-151.
Catala et al., 1989, Nucleic Acids Research, Vol. 17: 3811-3827.
Chen et al., 1987, Mol. Cell. Biol., 7: 2745-2752.
Chomczynski, P. and Sacchi, 1987, Anal. Biochem., 162, 156-159.
Chou, 1989, Mol. Endocrinol., Vol. 3: 1511-1514.
DeRisi J. et al., 1997, Science, 278, 680-686.
Felgner et al., PNAS 84 (1987) 7413.
Fikes et al., 1990, Nature, Vol. 346: 291-294.
Flotte et al., 1992, *Am. J. Respir. Cell Mol. Biol.*, 7: 349-356.
Fraley et al., 1979, Proc. Natl. Acad. Sci. USA, 76: 3348-3352.
Fraley et al., J. Biol. Chem. 255 (1980) 10431.
Fuller S. A. et al., 1996, *Immunology in Current Protocols in Molecular Biology*, Ausubel et al.
Gill et al., 1991, Cell, Vol. 65: 333-340.
Gopal, 1985, Mol. Cell. Biol., 5:1188-1190.
Graham et al., 1973, Virology, 52: 456-457.
Graham et al., J. Gen. Virol. 36 (1977) 59.
Graham, 1984, EMBO J., Vol. 3: 2917.
Grange et al., 1991, Nucleic Acids Research, Vol. 19: 131-139 Ham, Methods Cell. Biol. 21a (1980) 255.
Hames B D and Higgins S J, 1985, "Nucleic acid hybridization: a practical approach", Hames and Higgins Ed., IRL Press, Oxford.
Harland et al., 1985, J. Cell. Biol., 101: 1094-1095.
Hoffmann et al., 1990, Gene Dev., Vol. 4: 1141-1148.
Huygen et al., 1996, Nature Medicine, 2(8): 893-898.
Janowski et al., 1999, Proc. Natl. Acad. Sci. USA, Vol. 96: 266-271.
Kaneda et al., Science 243 (1989) 375.
Kim et al., 1990, Mol Cell Biol, Vol. 10: 5958-5966
Langmann T. et al., 1999, Biochem. Biophys. Res. Comm., 257: 29-33.
Levrero et al., Gene 101 (1991
Lim et al., 1992, J. Biol. Chem., Vol. 268: 18008-18017.
Luciani M. F. et al., 1994, Genomics, 21: 150-159.
Lum et al., 1990, Mol Cell Biol, Vol. 10: 6709-6717.
Lyer V. et al., 1999, Science, 283: 83-87.
Mansour et al., 1988, Nature, Vol. 336: 348-352.
Mantovani et al., 1988, Nucleic Acids Research, Vol. 16: 4299-4313.
Marcil M. et al., 1999, The Lancet, Vol. 354:1341-1346
McCormick, BioTechnology 3 (1985) 689.
McLaughlin B A et al., 1996, *Am. J. Hum. Genet.,* 59: 561-569.
Nagy et al., 1993, Proc. Natl. Acad. Sci. USA, Vol. 90: 8424-8428.
Narang S A, Hsiung H M, Brousseau R, *Methods Enzymol* 1979; 68: 90-98.
Nicolau C. et al., 1987, Methods Enzymol., 14: 157-76.
Overdier et al., 1994, Mol Cell Biol, Vol. 14: 2755-2766.
Pagano et al., J. Virol. 1 (1967) 891.
Remaley A. et al., Proc Nat Acad Sci USA, 1999, 96: 12685-12690.
Remmington's Pharmaceutical Sciences, Mead Publishing Co., Easton, Pa.
Rosenthal et al., 1990, Nucleic Acids Research, Vol. 18: 6239.
Rust S. et al., Nature Genetics, Vol. 20, September 1998, pages 96-98.
Rust S. et al., Nature Genetics, Vol. 22, August 1999, pages 352-355.
Sambrook, J. Fritsch, E. F., and T. Maniatis, 1989. Molecular cloning: a laboratory manual. 2ed. Cold Spring Harbor Laboratory, Cold Spring Harbor, N.Y.
Samulski et al., 1989, *J. Virol.,* 63: 3822-3828.
Sanchez-Pescador R., 1988, *J. Clin. Microbiol.,* 26 (10): 1934-1938.
Schay et al., 1991, Biochem Biophys Acta, Vol. 1072: 1-7.
Song et al., 1994, Proc. Natl. Acad. Sci. USA, Vol. 91: 10809-10813.
Sternberg N. L., 1992, Trends Genet., 8: 1-16.
Sternberg N. L., 1994, Mamm. Genome, 5: 397-404.
Tacson et al., 1996, Nature Medicine, 2 (8): 888-892.
Thomas et al., 1987, Cell, Vol. 51: 503-512.
Tur-Kaspa et al., 1986, Mol. Cell. Biol., 6: 716-718.
Urdea M. S., 1988, *Nucleic Acids Research,* 11: 4937-4957.
Urdea M. S. et al., 1991, *Nucleic Acids Symp Ser.,* 24: 197-200.
Wagner et al., 1990, EMBO J., Vol. 9: 4477-4784.
Wang et al., 1993, Mol. Cell Biol. Vol. 13: 5691-5701.
Webb and Hurskainen, 1996, Journal of Biomolecular Screening, Vol. 1: 119.
Willy et al., 1995, Genes Dev. 9: 1033-1045.
Wood et al., 1993, Proc. Natl. Acad. Sci. USA, Vol. 90: 4582-4585.

What is claimed is:

1. An isolated nucleic acid comprising a polynucleotide having the nucleotide sequence from nucleotide 666 to nucleotide 3001 of the nucleotide sequence SEQ ID NO: 1, or the complement of the nucleotide sequence from nucleotide 666 to nucleotide 3001 of SEQ ID NO: 1.

2. An isolated nucleic acid, comprising a polynucleotide comprising nucleotides 1576 to 2893 of SEQ ID No. 3.

3. An isolated nucleic acid, wherein said isolated nucleic acid is a polynucleotide comprising nucleotide 2694 to nucleotide 2893 of the nucleotide sequence SEQ ID NO: 1.

4. The isolated nucleic acid according to claim 3, wherein said isolated nucleic acid is a polynucleotide comprising the nucleotide sequence from nucleotide 2594 to nucleotide 2893 of the nucleotide sequence SEQ ID NO: 1.

5. The isolated nucleic acid according to claim 3, wherein said isolated nucleic acid is a polynucleotide comprising the nucleotide sequence from nucleotide 2294 to nucleotide 2893 of the nucleotide sequence SEQ ID NO: 1.

6. The isolated nucleic acid according to claim 3, wherein said isolated nucleic acid is a polynucleotide comprising the nucleotide sequence from nucleotide 1 to the nucleotide 2893 of the nucleotide sequence SEQ ID NO: 1.

7. An isolated nucleic acid, wherein said isolated nucleic acid is a polynucleotide comprising the nucleotide sequence from nucleotide 1899 to nucleotide 3013 of the nucleotide sequence SEQ ID NO: 1.

8. The isolated nucleic acid according to claim 1, wherein said isolated nucleic acid is a polynucleotide comprising the nucleotide seciuence from nucleotide 654 to nucleotide 3001 of the nucleotide sequence SEQ ID NO: 1 or the complete complement thereof.

9. A recombinant vector comprising at least one isolated nucleic acid according to claim 1.

10. The recombinant vector according to claim 9, wherein said vector is chosen from a recombinant cloning vector and a recombinant expression vector.

11. An isolated host cell transformed with a recombinant vector according to claim 9.

* * * * *